(12) United States Patent
Hook et al.

(10) Patent No.: US 9,067,883 B2
(45) Date of Patent: Jun. 30, 2015

(54) INTERMEDIATES OF NEUTRAL ENDOPEPTIDASE INHIBITORS AND PREPARATION METHOD THEREOF

(75) Inventors: David Hook, Rheinfelden (CH); Jianguang Zhou, Suzhou (CN); Yunzhong Li, Suzhou (CN); Jie Ku, Suzhou (CN)

(73) Assignee: Novartis AG, Basel (CH)

( * ) Notice: Subject to any disclaimer, the term of this patent is extended or adjusted under 35 U.S.C. 154(b) by 249 days.

(21) Appl. No.: 13/522,995

(22) PCT Filed: Jan. 21, 2011

(86) PCT No.: PCT/CN2011/070458
§ 371 (c)(1),
(2), (4) Date: Jul. 19, 2012

(87) PCT Pub. No.: WO2011/088797
PCT Pub. Date: Jul. 28, 2011

(65) Prior Publication Data
US 2012/0289710 A1     Nov. 15, 2012

(30) Foreign Application Priority Data

Jan. 22, 2010  (WO) ................ PCT/CN2010/070322

(51) Int. Cl.
*C07D 207/277* (2006.01)
*C07D 207/38* (2006.01)
*C07D 207/26* (2006.01)
*C07D 207/267* (2006.01)
*C07D 207/263* (2006.01)

(52) U.S. Cl.
CPC .......... *C07D 207/267* (2013.01); *C07D 207/26* (2013.01); *C07D 207/38* (2013.01); *C07D 207/263* (2013.01); *C07D 207/277* (2013.01)

(58) Field of Classification Search
CPC . C07D 207/277; C07D 207/38; C07D 207/26

USPC .................. 548/543, 536, 539, 540
See application file for complete search history.

(56) References Cited

U.S. PATENT DOCUMENTS

| 5,217,996 A | 6/1993 | Ksander |
| 2003/0171578 A1 | 9/2003 | Iizuka et al. |

FOREIGN PATENT DOCUMENTS

| EP | 0916656 A2 | 5/1999 |
| WO | WO 2008/083967 A2 | 7/2008 |
| WO | WO 2008083967 A2 * | 7/2008 |
| WO | 2009090251 | 7/2009 |
| WO | WO 2009/090251 A2 | 7/2009 |

OTHER PUBLICATIONS

Riofiski, et al., 2011, "Exploiting the Facile Release of Trifluoroacetate for the alpha-Methylenation of the Sterically Hindered Carbonyl Groups on (+)-Sclareolide and (−)-Eburnamonine", Jorurnal of Organic Chemistry, 76:3676-3683.
Ueno et al., 1978, "Deacylative Condensation I. A New Facile Method for the Direct alpha-Methylenation of Ester or Lactone Starting From Monosubstituted Active Methylene Compounds", Tetrahedron Letters, 39:3753-3756.
Toshiyuki Kan et al. Organic Letters 2004, vol. 6, No. 16, pp. 2729-2731.

* cited by examiner

*Primary Examiner* — Joseph Kosack
*Assistant Examiner* — Matthew Coughlin
(74) *Attorney, Agent, or Firm* — Matthew Mulkeen; David R. Kurlandsky

(57) ABSTRACT

The invention relates to a new process for producing useful intermediates for the manufacture of NEP inhibitors or prodrugs thereof, in particular NEP inhibitors comprising a g-amino-d-biphenyl-a-methylalkanoic acid, or acid ester, backbone, such as N-(3-carboxyl-1-oxopropyl)-(4S)-(p-phenylphenylmethyl)-4-amino-(2R)-methyl butanoic acid ethyl ester or salt thereof.

17 Claims, No Drawings

INTERMEDIATES OF NEUTRAL ENDOPEPTIDASE INHIBITORS AND PREPARATION METHOD THEREOF

This application is a National Phase application of PCT/CN2011/070458, filed Jan. 21, 2011, which claims benefit of China application PCT/CN2010/070322, filed Jan. 22, 2010.

The invention relates to a new process for producing useful intermediates for the manufacture of NEP inhibitors or pro-drugs thereof, in particular NEP inhibitors comprising a γ-amino-δ-biphenyl-α-methylalkanoic acid, or acid ester, backbone.

Endogenous atrial natriuretic peptides (ANP), also called atrial natriuretic factors (ANF) have diuretic, natriuretic and vasorelaxant functions in mammals. The natural ANF peptides are metabolically inactivated, in particular by a degrading enzyme which has been recognized to correspond to the enzyme neutral endopeptidase (NEP, EC 3.4.24.11), also responsible for e.g. the metabolic inactivation of enkephalins.

In the art biaryl substituted phosphonic acid derivatives are known which are useful as neutral endopeptidase (NEP) inhibitors, e.g. as inhibitors of the ANF-degrading enzyme in mammals, so as to prolong and potentiate the diuretic, natriuretic and vasodilator properties of ANF in mammals by inhibiting the degradation thereof to less active metabolites. NEP inhibitors are thus particularly useful for the treatment of conditions and disorders responsive to the inhibition of neutral endopeptidase (EC 3.4.24.11), particularly cardiovascular disorders such as hypertension, renal insufficiency including edema and salt retention, pulmonary edema and congestive heart failure.

Processes for preparing NEP-inhibitors are known. U.S. Pat. No. 5,217,996 describes biaryl substituted 4-amino-butyric acid amide derivatives which are useful as neutral endopeptidase (NEP) inhibitors, e.g. as inhibitors of the ANF-degrading enzyme in mammals. U.S. Pat. No. 5,217,996 discloses the preparation of N-(3-carboxyl-1-oxopropyl)-(4S)-(p-phenylphenylmethyl)-4-amino-(2R)-methyl butanoic acid ethyl ester. In the preparation of said compound N-t-butoxycarbonyl-(4R)-(p-phenylphenylmethyl)-4-amino-2-methyl-2-butenoic acid ethyl ester is hydrogenated in the presence of palladium on charcoal. WO2009/090251 relates to a reaction route for preparing compound N-t-butoxycarbonyl(4S)-(p-phenylphenylmethyl)-4-amino-2-methylbutanoic acid ethyl ester, or salt thereof, wherein an alternative hydrogenation step provides improved diastereoselectivity compared to that obtained in U.S. Pat. No. 5,217,996. A key intermediate of the route described in WO2009/090251 is a compound of formula (1),

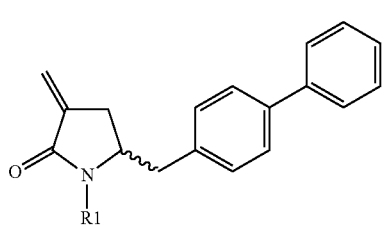

(1)

or salt thereof,
wherein R1 is hydrogen or a nitrogen protecting group. Section B in WO2009/090251 discloses different methods for preparing a compound of formula (1). All such methods use as starting material a compound of formula (2), or salt thereof,

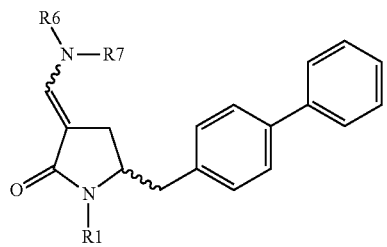

(2)

wherein R1 is hydrogen or a nitrogen protecting group and R6 and R7 are, independently, an alkyl group, an aryl group, an arylalkyl group, a cycloalkyl group or together R6 and R7 form a cycle, together with the nitrogen to which they are attached, which cycle may be saturated or unsaturated and may optionally contain one or more heteroatoms, such as a nitrogen, oxygen or sulphur, whereby the cycle contains 3 to 8, such as 4 to 7 ring atoms. As described in Section A in WO2009/090251, the preparation of a compound of formula (2), or salt thereof, comprises reacting a compound of formula (3), or salt thereof,

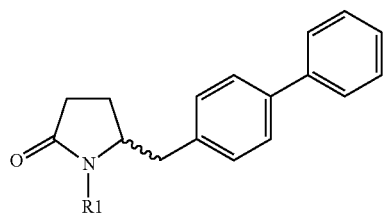

(3)

wherein R1 is hydrogen or a nitrogen protecting group, with an amine of formula (13), (14) or (15), or mixtures thereof,

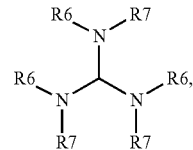

(13)

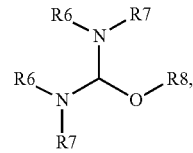

(14)

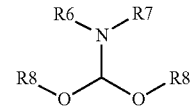

(15)

wherein each R6 and each R7 are, independently, an alkyl group, an aryl group, an arylalkyl group, a cycloalkyl group or together R6 and R7 form a cycle, together with the nitrogen to which they are attached, which cycle may be saturated or unsaturated and may optionally contain one or more heteroatoms, such as a nitrogen, oxygen or sulphur, whereby the cycle contains 3 to 8, such as 4 to 7 ring atoms, and each R8 is, independently, an alkyl group, an aryl group or an arylalkyl group to obtain the compound of formula (2).

The large scale preparation of an amine of formula (13), (14) or (15) is a difficult process, which leads to mixtures thereof wherein the ratio of each amine may change from one batch to another. The reactivity of amines of formula (13), (14) or (15) is different. Accordingly, in view of the fact that the preparation of an amine of formula (13), (14) or (15) results in variable mixtures thereof with different reactivity profiles, the commercial scale manufacture of a compound of formula (1) via a compound of formula (2) is troublesome. Therefore, there is a need for the development of an alternative synthesis of compounds of formula (1), as described above, which can be used for the commercial scale manufacture thereof and avoids the above-mentioned drawbacks of the prior art process. Thus the object of the present invention is to provide a new process for preparing the compound of formula (1), which can be suitable for its commercial scale manufacture. The new process, according to the present invention, for producing a compound according to formula (1), or salt thereof, as defined herein, is summarized in Scheme 1.

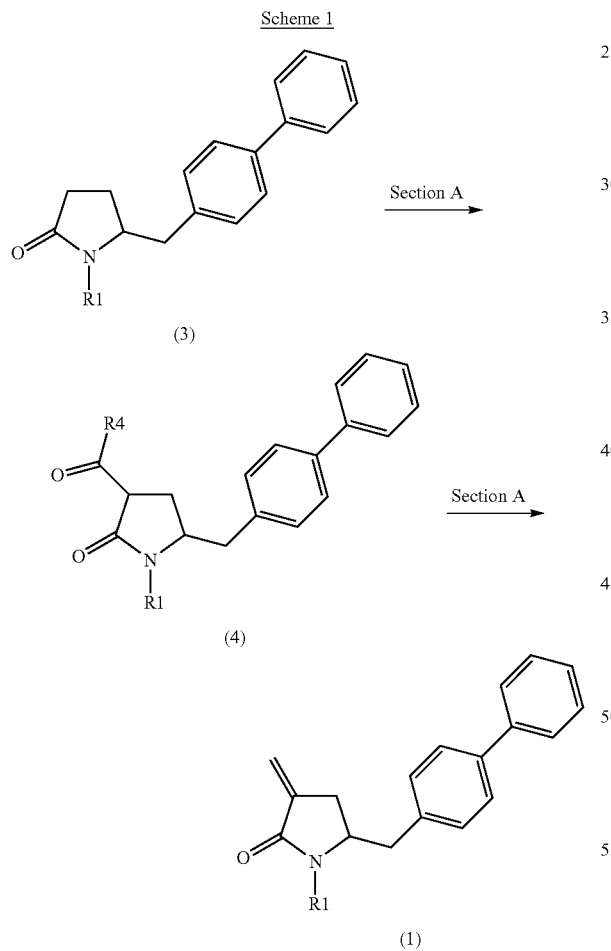

Namely, a compound of formula (3), as described herein, is converted into a compound of formula (1), or salt thereof, wherein R1 is hydrogen or a nitrogen protecting group, according to a method described in Section A.

The preparation of a compound of formula (3), as described herein, is described for example, in Method 1 of Subsection C-1 in WO2008/083967.

WO2008/083967 describes a process for converting a compound of formula (1), as described herein, into a NEP inhibitor or prodrug thereof. Therefore, a compound of formula (1) can be used as an intermediates in the preparation of NEP inhibitors, or prodrugs thereof, in particular NEP inhibitors comprising a γ-amino-6-biphenyl-α-methylalkanoic acid, or acid ester, backbone, preferably N-(3-carboxyl-1-oxopropyl)-(4S)-(p-phenylphenylmethyl)-4-amino-(2R)-methyl butanoic acid alkyl ester, such as N-(3-carboxyl-1-oxopropyl)-(4S)-(p-phenylphenylmethyl)-4-amino-(2R)-methyl butanoic acid ethyl ester.

The invention as a whole comprises the following sections:

Section A: Preparation methods for the compound of formula (1)

Section B: Novel and inventive compounds

Section C: Examples

It is noted that in the present application usually explanations made in one section are also applicable for other sections, unless otherwise stated. For example, the explanations for the residue R4 in formula (4) given in section A also apply if formula (4) occurs in section B unless otherwise stated. When referring to compounds described in the present invention, it is understood that reference is also being made to salts thereof. Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms.

In a further embodiment, the present invention also relates to a process for preparing N-(3-carboxyl-1-oxopropyl)-(4S)-(p-phenylphenylmethyl)-4-amino-(2R)-methyl butanoic acid ethyl ester, or a salt thereof, comprising the manufacture of compound of formula (4), or salt thereof, as defined above.

Section A: Preparation of a Compound of Formula (1)

Section A.1: Synthesis of a Compound of Formula (4)

This section relates to a process for the manufacture of a compound of formula (1), as defined herein, wherein the conversion of a compound of formula (3), as defined herein, into said compound of formula (1) takes place step-wise, i.e. in two separate steps with isolation of the intermediate species of formula (4), as defined herein.

In one embodiment, the present invention relates to a process for preparing a compound of formula (4), or salt thereof,

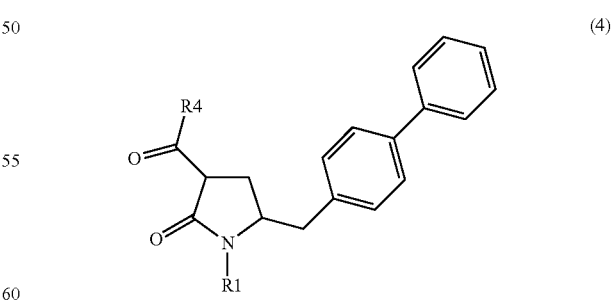

(4)

wherein

R1 is hydrogen or a nitrogen protecting group; and

R4 is selected from hydroxyl, alkyl, aryl and arylalkyl; preferably wherein the compound of formula (4) is of the formula (4a)

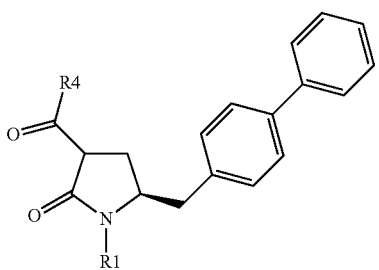

(4a)

wherein R1 and R4 are as defined for the compound of formula (4); said process comprising
reacting a compound of formula (3), or salt thereof,

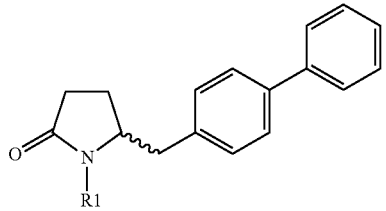

(3)

wherein R1 is hydrogen or a nitrogen protecting group;
preferably wherein the compound of formula (3) is of the formula (3a)

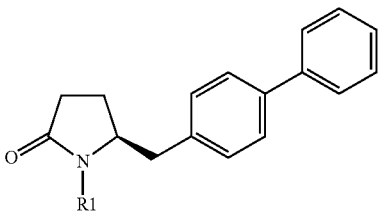

(3a)

wherein R1 is as defined for the compound of formula (3);
first with a base and then with a compound of the formula $CO_2$ or R4COY, wherein Y is halogen or —OR' and wherein R4 and R' are independently selected from alkyl, aryl and arylalkyl, to obtain the compound of formula (4), or salt thereof.

In another embodiment, the present invention relates to a process for preparing a compound of formula (4), or salt thereof,

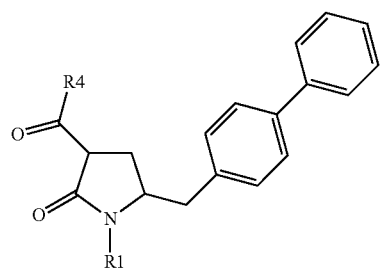

(4)

wherein
R1 is hydrogen or a nitrogen protecting group; and
R4 is hydroxyl;
preferably wherein the compound of formula (4) is of the formula (4a)

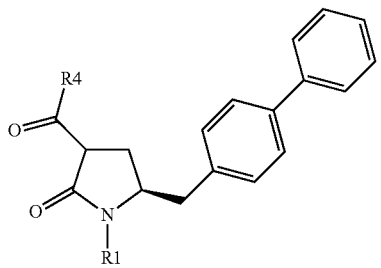

(4a)

wherein R1 and R4 are as defined for the compound of formula (4);
said process comprising
reacting a compound of formula (3), or salt thereof,

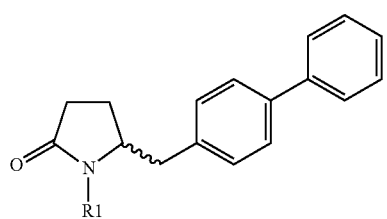

(3)

wherein R1 is hydrogen or a nitrogen protecting group;
preferably wherein the compound of formula (3) is of the formula (3a)

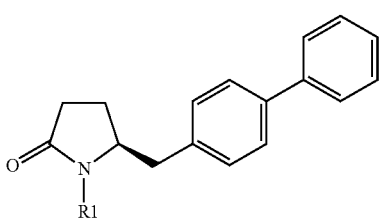

(3a)

wherein R1 is as defined for the compound of formula (3);
first with a base and then with a compound of the formula $CO_2$ to obtain the compound of formula (4), or salt thereof.

Suitable bases for the conversion of a compound of formula (3), preferably of formula (3a), as described herein, into a compound of formula (4), preferably of formula (4a), as described herein, include:
  metal hydrides, such as alkali metal hydrides (eg sodium or potassium hydride);
  alkali metal alkoxides (eg sodium methoxide, potassium tert-butoxide);
  amines, such as 1,3-dimethyl-3,4,5,6-tetrahydro-2(1H)-pyrimidinone (DMPU);
  a base of the formula MRa, wherein M is an alkali metal (eg lithium, sodium, potassium) and Ra is alkyl or aryl, for example MRa is methyl lithium, n-butyllithium, sec-butyllithium, tert-butyllithium or phenyllithium;
  a base of the formula RcRdNM, wherein Rc and Rd are independently selected from alkyl, cycloalkyl, heterocyclyl or silyl and M is an alkali metal (eg lithium, sodium, potassium), for example RcRdNM is lithium bis(trimethylsilyl)amide (LHMDS), sodium bis(trimethylsilyl)amide (NaHMDS), potassium bis(trimethylsilyl)amide (KHMDS), lithium diisopropylamide (LDA) or potassium diisopropylamide; or mixtures thereof.

In one embodiment the base is an amine, such as triethylamine, diisopropylethyl amine, optionally in the presence of an additive selected from an alkaline earth metal halide, such as magnesium chloride, magnesium bromide and magnesium iodide.

Preferably, the base is LHMDS, lithium diisopropylamide or sodium hydride, most preferably LHMDS.

Section A.2: Synthesis of a Compound of Formula (1) from a Compound of Formula (4)

In another aspect, the present invention relates to a process for preparing a compound of formula (1), or salt thereof,

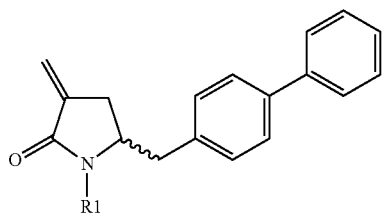
(1)

wherein R1 is hydrogen or a nitrogen protecting group; preferably wherein the compound of formula (1) is of the formula (1a)

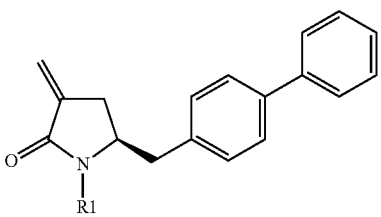
(1a)

wherein R1 is as defined for the compound of formula (1); said process comprising reacting a compound of formula (4), or salt thereof,

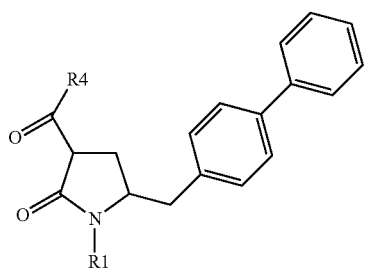
(4)

wherein
R1 is hydrogen or a nitrogen protecting group; and
R4 is selected from hydroxyl, alkyl, aryl and arylalkyl;
preferably wherein the compound of formula (4) is of the formula (4a)

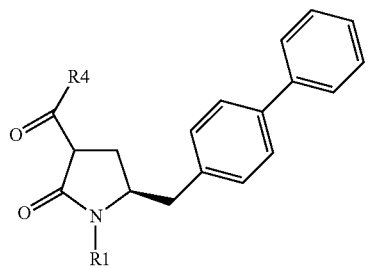
(4a)

wherein R1 and R4 are as defined for the compound of formula (4);
with a base and formaldehyde, optionally in the presence of a phase transfer catalyst, to obtain the compound of formula (1), or salt thereof.

Suitable bases for the conversion of a compound of formula (4), preferably of formula (4a), as described herein, into a compound of formula (1), preferably of formula (1a), as described herein, include metal hydrides, such as alkali metal hydrides (eg sodium or potassium hydride), alkali metal alkoxides (eg sodium methoxide, potassium tert-butoxide), an amine, such as diisopropylethylamine, triethylamine, morpholine or 1,8-diazabicyclo[5.4.0]undec-7-ene, an inorganic base, such an alkali metal carbonate, such as potassium carbonate, a base of the formula MRa, wherein M is an alkali metal (eg lithium sodium, potassium) and Ra is alkyl or aryl, for example MRa is methyl lithium, n-butyllithium, sec-butyllithium, tert-butyllithium or phenyllithium, a base of the formula RcRdNM, wherein Rc and Rd are independently selected from alkyl, cycloalkyl, heterocyclyl or silyl and M is an alkali metal (eg lithium sodium, potassium), for example RcRdNM is lithium bis(trimethylsilyl)amide (LHMDS), sodium bis(trimethylsilyl)amide (NaHMDS), potassium bis(trimethylsilyl)amide (KHMDS), lithium diisopropylamide (LDA) or potassium diisopropylamide; or mixtures thereof.

In a preferred embodiment, the conversion of a compound of formula (4), preferably wherein the compound of formula (4) is of the formula (4a), into a compound of formula (1), as described above, takes place in the presence of a base and an alkali metal salt, such as LiCl. More preferably, this conversion takes place in the presence of a base, an alkali metal salt, such as LiCl, and a drying agent, such as molecular sieves, an alkali metal sulphate (eg sodium sulphate) or an alkaline earth metal sulphate (eg magnesium sulphate).

Section A.2: Synthesis of a Compound of Formula (1) from a Compound of Formula (3)

In another embodiment, the present invention relates to a process for preparing a compound of formula (1), or salt thereof,

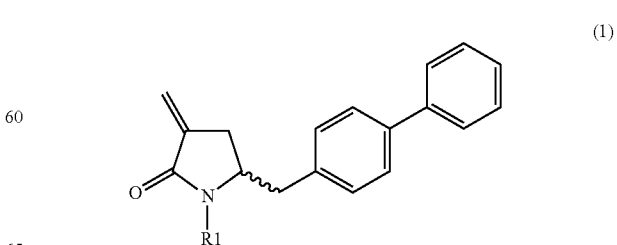
(1)

wherein R1 is hydrogen or a nitrogen protecting group;

preferably wherein the compound of formula (1) is of the formula (1a)

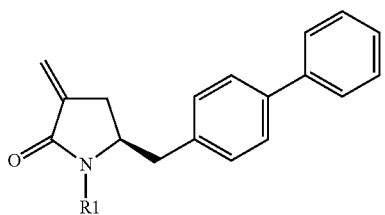

(1a)

wherein R1 is as defined for the compound of formula (1);
said process comprising the steps of
(i) preparing a compound of formula (4), or salt thereof,

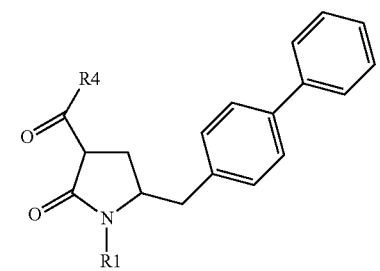

(4)

wherein
R1 is hydrogen or a nitrogen protecting group; and
R4 is selected from hydroxyl, alkyl, aryl and arylalkyl;
preferably wherein the compound of formula (4) is of the formula (4a)

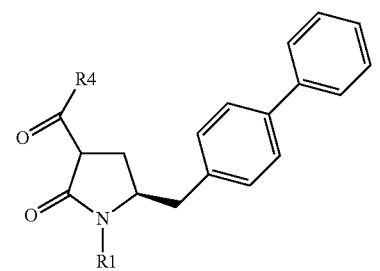

(4a)

wherein R1 and R4 are as defined for the compound of formula (4);
by reacting a compound of formula (3), or salt thereof,

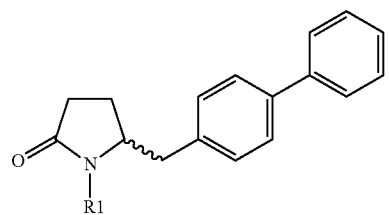

(3)

wherein R1 is hydrogen or a nitrogen protecting group;

preferably wherein the compound of formula (3) is of the formula (3a)

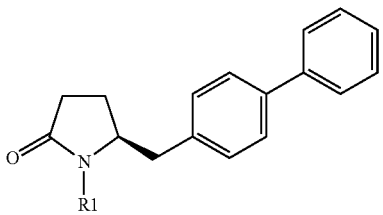

(3a)

wherein R1 is as defined for the compound of formula (3); first with a base and then with a compound of the formula $CO_2$ or R4COY, wherein Y is halogen or —OR' and wherein R4 and R' are independently selected from alkyl, aryl and arylalkyl, to obtain the compound of formula (4), or salt thereof; and
(ii) reacting the compound of formula (4), or salt thereof, (4)

[structure]

wherein
R1 is hydrogen or a nitrogen protecting group; and
R4 is selected from hydroxyl, alkyl, aryl and arylalkyl;
preferably wherein the compound of formula (4) is of the formula (4a)

(4a)

[structure]

wherein R1 and R4 are as defined for the compound of formula (4);
with a base and formaldehyde, optionally in the presence of a phase transfer catalyst, to obtain the compound of formula (1), or salt thereof.

In another aspect, the present invention relates to the above process, to convert the compound of formula (3) into the compound of formula (1), wherein steps i) and ii) take place via one-pot process, thus without isolation and/or purification of the compound of formula (4).

In a further embodiment, the present invention relates to a process for preparing a compound of formula (1), or salt thereof, (1)

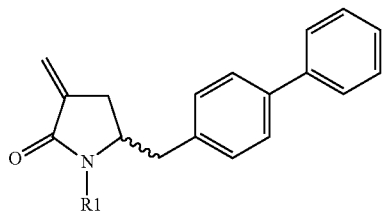

wherein R1 is hydrogen or a nitrogen protecting group; preferably wherein the compound of formula (1) is of the formula (1a)

(1a)

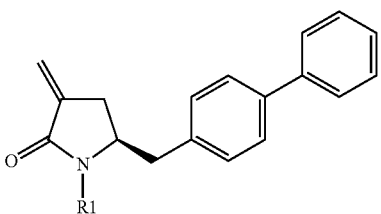

wherein R1 is as defined for the compound of formula (1);
said process comprising the steps of
(i) preparing a compound of formula (4), or salt thereof, (4)

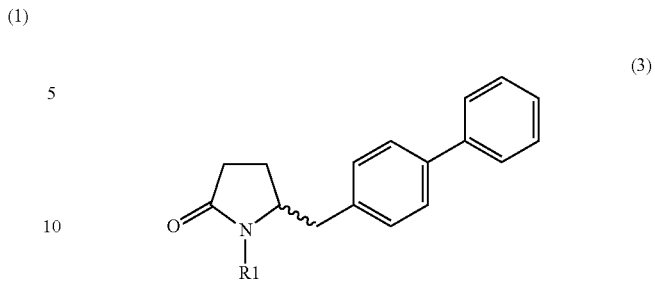

wherein
R1 is hydrogen or a nitrogen protecting group; and
R4 is hydroxyl;
preferably wherein the compound of formula (4) is of the formula (4a)

(4a)

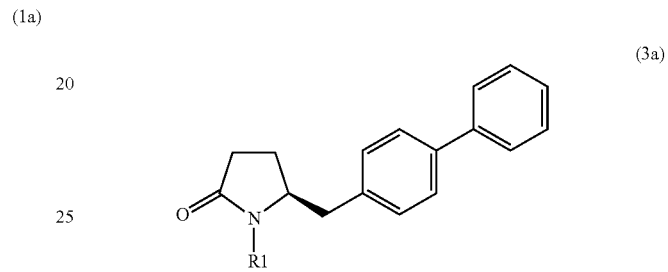

wherein R1 and R4 are as defined for the compound of formula (4);

by reacting a compound of formula (3), or salt thereof, (3)

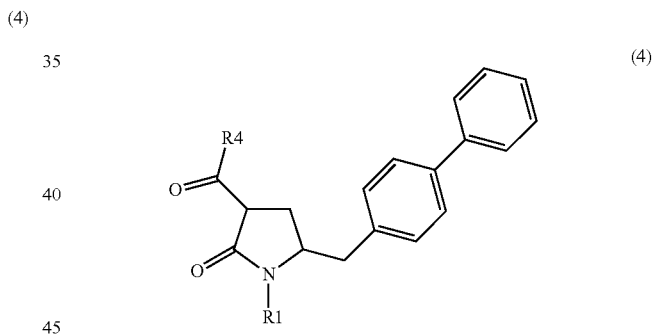

wherein R1 is hydrogen or a nitrogen protecting group;
preferably wherein the compound of formula (3) is of the formula (3a)

(3a)

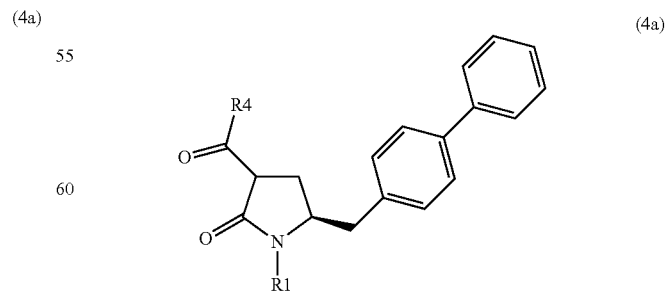

wherein R1 is as defined for the compound of formula (3);
first with a base and then with a compound of the formula $CO_2$ to obtain the compound of formula (4), or salt thereof; and
(ii) reacting the compound of formula (4), or salt thereof, (4)

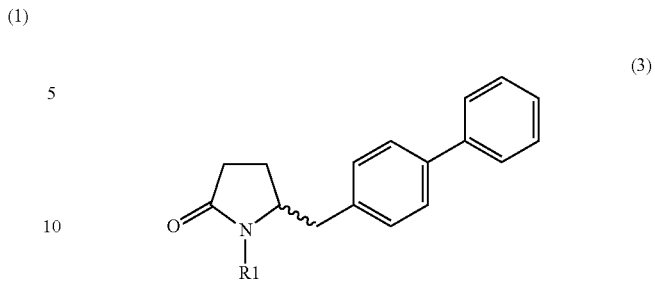

wherein
R1 is hydrogen or a nitrogen protecting group; and
R4 is hydroxyl;
preferably wherein the compound of formula (4) is of the formula (4a)

(4a)

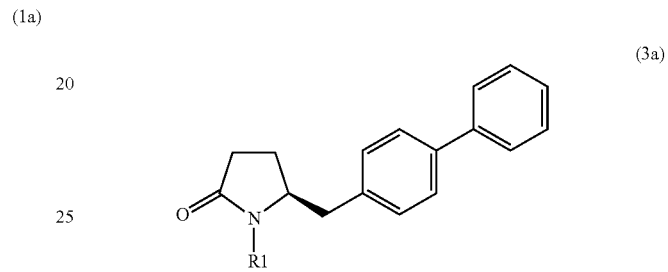

wherein R1 and R4 are as defined for the compound of formula (4);

with a base and formaldehyde, optionally in the presence of a phase transfer catalyst, to obtain the compound of formula (1), or salt thereof.

In yet another aspect, the present invention relates to the above process, to convert the compound of formula (3) into the compound of formula (1), wherein steps i) and ii) take place via one-pot process, thus without isolation and/or purification of the compound of formula (4).

Suitable bases for step (i), in the above embodiments, are as those described in Section A.1.

Suitable bases for step (ii), in the above embodiments, are as those described in Section A. 2. Preferably, step (ii), in the above embodiments, takes place in the presence of a base and an alkali metal salt, such as LiCl. More preferably, this conversion takes place in the presence of a base, an alkali metal salt, such as LiCl, and a drying agent, such as molecular sieves, an alkali metal sulphate (eg sodium sulphate) or an alkaline earth metal sulphate (eg magnesium sulphate).

Section B:
A compound of formula (4), or salt thereof,

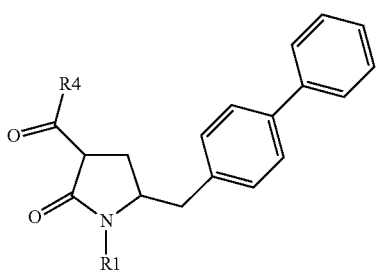

(4)

wherein
R1 is hydrogen or a nitrogen protecting group; and
R4 is selected from hydroxyl, alkyl, aryl and arylalkyl;
preferably wherein the compound of formula (4) is of the formula (4a)

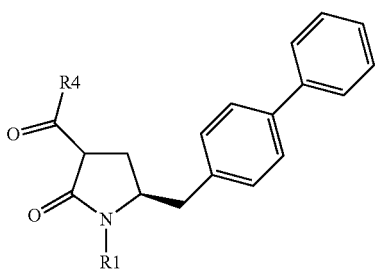

(4a)

wherein R1 and R4 are as defined for the compound of formula (4).

General Terms:
The general definitions used above and below, unless defined differently, have the following meanings:

The term "nitrogen protecting group" comprises any group which is capable of reversibly protecting a nitrogen functionality, preferably an amine and/or amide functionality. Preferably the nitrogen protecting group is an amine protecting group and/or an amide protecting group. Suitable nitrogen protecting groups are conventionally used in peptide chemistry and are described e.g. in the relevant chapters of standard reference works such as J. F. W. McOmie, "Protective Groups in Organic Chemistry", Plenum Press, London and New York 1973, in P. G. M. Wuts and T. W. Greene, "Greene's Protective Groups in Organic Synthesis", Fourth Edition, Wiley, New Jersey, 2007, in "The Peptides"; Volume 3 (editors: E. Gross and J. Meienhofer), Academic Press, London and New York 1981, and in "Methoden der organischen Chemie" (Methods of Organic Chemistry), Houben Weyl, 4th edition, Volume 15/I, Georg Thieme Verlag, Stuttgart 1974.

Preferred Nitrogen Protecting Groups Generally Comprise:

Unsubstituted or substituted $C_1$-$C_6$-alkyl, preferably $C_1$-$C_4$-alkyl, more preferably $C_1$-$C_2$-alkyl, most preferably $C_1$alkyl, unsubstituted or substituted $C_{2-4}$alkenyl, wherein $C_1$-$C_6$-alkyl and $C_{2-4}$alkenyl is optionally mono-, di- or tri-substituted by trialkylsilyl$C_1$-$C_7$-alkoxy (eg. trimethylsilylethoxy), aryl, preferably phenyl, or an heterocyclic group, preferably pyrrolidinyl, wherein the aryl ring or the heterocyclic group is unsubstituted or substituted by one or more, e.g. two or three, residues, e.g. selected from the group consisting of $C_1$-$C_7$-alkyl, hydroxy, $C_1$-$C_7$-alkoxy, $C_2$-$C_8$-alkanoyl-oxy, halogen, nitro, cyano, and $CF_3$; aryl-$C_1$-$C_2$-alkoxycarbonyl (preferably phenyl-$C_1$-$C_2$-alkoxycarbonyl eg. benzyloxycarbonyl); $C_{1-10}$alkenyloxycarbonyl; $C_{1-6}$alkylcarbonyl (eg. acetyl or pivaloyl); $C_{6-10}$arylcarbonyl; $C_{1-6}$alkoxycarbonyl (eg. t-butoxycarbonyl); $C_{6-10}$aryl$C_{1-6}$ alkoxycarbonyl; allyl or cinnamyl; sulfonyl or sulfenyl; succinimidyl group, silyl, e.g. triarylsilyl or trialkylsilyl (eg. triethylsilyl).

Examples of preferred nitrogen protecting groups are acetyl, benzyl, cumyl, benzhydryl, trityl, benzyloxycarbonyl (Cbz), 9-fluorenylmethyloxycarbony (Fmoc), benzyloxymethyl (BOM), pivaloyl-oxy-methyl (POM), trichloroethoxycarbonyl (Troc), 1-adamantyloxycarbonyl (Adoc), allyl, allyloxycarbonyl, trimethylsilyl, tert.-butyl-dimethylsilyl, triethylsilyl (TES), triisopropylsilyl, trimethylsilylethoxymethyl (SEM), t-butoxycarbonyl (BOC), t-butyl, 1-methyl-1, 1-dimethylbenzyl, (phenyl)methylbenzene, pyrrodinyl and pivaloyl. Most preferred nitrogen protecting groups are acetyl, benzyl, benzyloxycarbonyl (Cbz), triethylsilyl (TES), trimethylsilylethoxymethyl (SEM), t-butoxycarbonyl (BOC), pyrrolidinylmethyl and pivaloyl.

Examples of more preferred nitrogen protecting groups are t-butoxycarbonyl (BOC), benzoyl, styryl, 1-butenyl, benzyl, p-methoxybenzyl (PMB) and pyrrolidinylmethyl.

Silyl, as used herein, refers to a group according to the formula —SiR11R12R13, wherein R11, R12 and R13 are, independently of each other, alkyl or aryl. Preferred examples for R11, R12 and R13 are methyl, ethyl, isopropyl, t-butyl, phenyl or phenyl-$C_{1-4}$alkyl.

Alkyl is defined as a radical or part of a radical is a straight or branch (one or, if desired and possible, more times) carbon chain, and is especially $C_1$-$C_7$-alkyl, preferably $C_1$-$C_4$-alkyl.

The term "$C_1$-$C_7$-" defines a moiety with up to and including maximally 7, especially up to and including maximally 4, carbon atoms, said moiety being branched (one or more times) or straight-chained and bound via a terminal or a non-terminal carbon Cycloalkyl is, for example, $C_3$-$C_7$-cycloalkyl and is, for example, cyclopropyl, cyclobutyl, cyclopentyl, cyclohexyl and cycloheptyl. Cyclopentyl and cyclohexyl are preferred.

Alkoxy is, for example, $C_1$-$C_7$-alkoxy and is, for example, methoxy, ethoxy, n-propyloxy, isopropyloxy, n-butyloxy, isobutyloxy, sec-butyloxy, tert-butyloxy and also includes corresponding pentyloxy, hexyloxy and heptyloxy radicals. $C_1$-$C_4$alkoxy is preferred.

Alkanoyl is, for example, $C_2$-$C_8$-alkanoyl and is, for example, acetyl [—C(=O)Me], propionyl, butyryl, isobutyryl or pivaloyl. $C_2$-$C_5$-Alkanoyl is preferred, especially acetyl.

Halo or halogen is preferably fluoro, chloro, bromo or iodo, most preferably, chloro, bromo, or iodo.

Halo-alkyl is, for example, halo-$C_1$-$C_7$alkyl and is in particular halo-$C_1$-$C_4$alkyl, such as trifluoromethyl, 1,1,2-trifluoro-2-chloroethyl or chloromethyl. Preferred halo-$C_1$-$C_7$alkyl is trifluoromethyl.

Alkenyl may be linear or branched alkyl containing a double bond and comprising preferably 2 to 12 C atoms, 2 to 10 C atoms being especially preferred. Particularly preferred is a linear $C_{2-4}$alkenyl. Some examples of alkyl groups are ethyl and the isomers of propyl, butyl, pentyl, hexyl, heptyl, octyl, nonyl, decyl, undecyl, dodecyl, tetradecyl, hexadecyl, octacyl and eicosyl, each of which containing a double bond. Especially preferred is allyl.

Alkylene is a bivalent radical derived from $C_{1-7}$alkyl and is especially $C_2$-$C_7$-alkylene or $C_2$-$C_7$alkylene and, optionally, can be interrupted by one or more, e.g. up to three, O, NR14 or S, wherein R14 is alkyl, each of which can be unsubstituted or substituted, by one or more substituents independently selected from for example, $C_1$-$C_7$-alkyl, $C_1$-$C_7$-alkoxy-$C_1$-$C_7$-alkyl or $C_1$-$C_7$-alkoxy.

Alkenylene is a bivalent radical derived from $C_{2-7}$alkenyl and can be interrupted by, one or more, e.g. up to three, O, NR14 or S, wherein R14 is alkyl, and is unsubstituted or substituted by one or more, e.g. up to three, substitutents preferably independently selected from the substitutents mentioned above for alkylene.

Aryl being a radical or part of a radical is, for example $C_{6-10}$aryl, and is, preferably a mono- or polycyclic, especially monocyclic, bicyclic or tricyclic aryl moiety with 6 to 10 carbon atoms, preferably phenyl, and which can be unsubstituted or substituted, by one or more substituents independently selected from for example, $C_1$-$C_7$-alkyl, $C_1$-$C_7$-alkoxy-$C_1$-$C_7$-alkyl or $C_1$-$C_7$-alkoxy.

The term arylalkyl refers to aryl-$C_1$-$C_7$-alkyl, wherein aryl is as defined herein and is for example benzyl.

The term carboxyl refers to —$CO_2H$.

Aryloxy refers to a Aryl-O— wherein aryl is as defined above.

Unsubstituted or substituted heterocyclyl is a mono- or polycyclic, preferably a mono-, bi- or tricyclic-, most preferably mono-, unsaturated, partially saturated, saturated or aromatic ring system with preferably 3 to 14 (more preferably 5 to 14) ring atoms and with one or more, preferably one to four, heteroatoms independently selected from nitrogen, oxygen, sulfur, S(=O)— or S—(=O)$_2$, and is unsubstituted or substituted by one or more, e.g. up to three, substitutents preferably independently selected from the Preferred substitutents are selected from the group consisting of halo, $C_1$-$C_7$-alkyl, halo-$C_1$-$C_7$-alkyl, $C_1$-$C_7$-alkoxy, halo-$C_1$-$C_7$-alkoxy, such as trifluoromethoxy and $C_1$-$C_7$-alkoxy-$C_1$-$C_7$-alkoxy. When the heterocyclyl is an aromatic ring system, it is also referred to as heteroaryl.

Acetyl is —C(=O)$C_1$-$C_7$alkyl, preferably —C(=O)Me.

Sulfonyl is (unsubstituted or substituted) $C_1$-$C_7$-alkylsulfonyl, such as methylsulfonyl, (unsubstituted or substituted) phenyl- or naphthyl-$C_1$-$C_7$alkylsulfonyl, such as phenylmethanesulfonyl, or (unsubstituted or substituted) phenyl- or naphthyl-sulfonyl; wherein if more than one substituent is present, e.g. one to three substitutents, the substituents are selected independently from cyano, halo, halo-$C_1$-$C_7$alkyl, halo-$C_1$-$C_7$-alkyloxy- and $C_1$-$C_7$-alkyloxy. Especially preferred is $C_1$-$C_7$-alkylsulfonyl, such as methylsulfonyl, and (phenyl- or naphthyl)-$C_1$-$C_7$-alkylsulfonyl, such as phenylmethanesulfonyl.

Sulfenyl is (unsubstituted or substituted) $C_{6-10}$aryl-$C_1$-$C_7$-alkylsulfenyl or (unsubstituted or substituted) $C_{6-10}$arylsulfenyl, wherein if more than one substituent is present, e.g. one to four substitutents, the substituents are selected independently from nitro, halo, halo-$C_1$-$C_7$alkyl and $C_1$-$C_7$-alkyloxy.

The term "chiral" refers to molecules which have the property of non-superimposability on their mirror image partner, while the term "achiral" refers to molecules which are superimposable on their mirror image partner.

The term "tautomer" refers in particular to the enol tautomer of the pyrrolidin-2-one moiety of the compounds of the present invention. Additionally, the term "tautomer" also refers in particular to the aldehyde tautomer of compounds of the present invention, e.g. compounds of the formula (6), where such compounds can exists in either an enol or aldehyde form, or mixtures thereof.

In the formulae of the present application the term "∿∿∿" on a C-sp$^3$ represents a covalent bond, wherein the stereochemistry of the bond is not defined. This means that the term "∿∿∿" on a C-sp$^3$ comprises an (S) configuration as well as an (R) configuration of the respective chiral centre. Furthermore, mixtures are also encompassed, e.g., mixtures of enantiomers, such as racemates, are encompassed by the present invention.

In the formulae of the present application the term "∿∿∿" on a C-sp$^2$ represents a covalent bond, wherein the stereochemistry or the geometry of the bond is not defined. This means that the term "∿∿∿" on a C-sp$^2$ comprises a cis (Z) configuration as well as a trans (E) configuration of the respective double bond. Furthermore, mixtures are also encompassed, e.g., mixtures of double bond isomers are encompassed by the present invention.

The compounds of the present invention can possess one or more asymmetric centers. The preferred absolute configurations are as indicated herein specifically.

In the formulae of the present application the term "╱" on a C-sp$^3$ indicates the absolute stereochemistry, either (R) or (S).

In the formulae of the present application the term "╱" on a C-sp$^3$ indicates the absolute stereochemistry, either (R) or (S).

In the formulae of the present application, the term "- - - - - -" indicates a Csp$^3$-Csp$^3$ bond or a Csp$^2$-Csp$^2$ bond.

Salts are especially pharmaceutically acceptable salts or generally salts of any of the intermediates mentioned herein, where salts are not excluded for chemical reasons the skilled person will readily understand. They can be formed where salt forming groups, such as basic or acidic groups, are present that can exist in dissociated form at least partially, e.g. in a pH range from 4 to 10 in aqueous solutions, or can be isolated especially in solid, especially crystalline, form.

Such salts are formed, for example, as acid addition salts, preferably with organic or inorganic acids, from compounds or any of the intermediates mentioned herein with a basic nitrogen atom (e.g. imino or amino), especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, lactic acid, fumaric acid, succinic acid, citric acid, amino acids, such as glutamic acid or aspartic acid, maleic acid, hydroxymaleic acid, methylmaleic acid, benzoic acid, methane- or ethane-sulfonic acid, ethane-1,2-disulfonic acid, benzenesulfonic acid, 2-naphthalenesulfonic acid, 1,5-naphthalene-disulfonic acid, N-cyclohexylsulfamic acid, N-methyl-, N-ethyl- or N-propyl-sulfamic acid, or other organic protonic acids, such as ascorbic acid.

In the presence of negatively charged radicals, such as carboxy or sulfo, salts may also be formed with bases, e.g. metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri(2-hydroxyethyl)amine, or heterocyclic bases, for example N-ethyl-piperidine or N,N'-dimethylpiperazine.

When a basic group and an acid group are present in the same molecule, any of the intermediates mentioned herein may also form internal salts.

For isolation or purification purposes of any of the intermediates mentioned herein it is also possible to use pharmaceutically unacceptable salts, for example picrates or perchlorates.

In view of the close relationship between the compounds and intermediates in free form and in the form of their salts, including those salts that can be used as intermediates, for example in the purification or identification of the compounds or salts thereof, any reference to "compounds", "starting materials" and "intermediates" hereinbefore and hereinafter is to be understood as referring also to one or more salts thereof or a mixture of a corresponding free compound, intermediate or starting material and one or more salts thereof, each of which is intended to include also any solvate or salt of any one or more of these, as appropriate and expedient and if not explicitly mentioned otherwise. Different crystal forms may be obtainable and then are also included.

Where the plural form is used for compounds, starting materials, intermediates, salts, pharmaceutical preparations, diseases, disorders and the like, this intended to mean one (preferred) or more single compound(s), salt(s), pharmaceutical preparation(s), disease(s), disorder(s) or the like, where the singular or the indefinite article ("a", "an") is used, this not intended to exclude the plural, but only preferably means "one".

Any of the lactams according to the present invention, or salts thereof, wherein R1 is hydrogen can be converted into a corresponding protected lactam, or salt thereof, wherein R1 is a nitrogen protecting group, as defined above, according to standard methods of organic chemistry known in the art, in particular reference is made to conventional nitrogen protecting group methods described in J. F. W. McOmie, "Protective Groups in Organic Chemistry", Plenum Press, London and New York 1973, in P. G. M. Wuts and T. W. Greene, "Greene's Protective Groups in Organic Synthesis", Fourth Edition, Wiley, New Jersey, 2007 and in Richard C. Larock, "Comprehensive Organic Transformations: A Guide to Functional Group Preparations", Second Edition, Wiley-VCH Verlag GmbH, 2000, in particular, in the relevant chapters thereof.

Analogously, any of the lactams according to the present invention, or salt thereof, wherein R1 is a nitrogen protecting group, can be converted into the corresponding lactam, or salt thereof, wherein R1 is a hydrogen, according to standard methods of organic chemistry known in the art, in particular reference is made to conventional nitrogen protecting group methods described in the books mentioned above, in particular, in the relevant sections.

The term "one-pot" "or "one-pot process" means that in a series of reactions, each reaction product is provided for the next reaction without isolation and/or purification. The term "purification" as used herein wherein, in particular, relates to crystallization, column chromatography or distillation. The one-pot processes defined herein encompass not only a series of reactions conducted in a single reaction vessel, but also a series of reactions conducted in a plurality of reaction vessels (e.g., by transferring the reaction mixture from one vessel to other) without isolation and/or purification. Preferably, the one-pot process is conducted in a single reaction vessel.

The term "formaldehyde", as used herein, is intended to include monomeric formaldehyde and any formaldehyde source that is readily converted to formaldehyde. For example, "formaldehyde", as used herein, includes formaldehyde in its monomeric form as well as its various acetals, hemiacetals, and low molecular weight oligomers such as, for example, paraformaldehyde.

The term "phase transfer catalyst" as used herein refers to a catalytic amount of a chemical agent that enhances the rate of a reaction between chemical species located in different phases (eg. immiscible liquids or solid and liquid) by extracting one of the reactants, most commonly an anion, across the interface into the other phase. These catalysts include quaternary ammonium or phosphonium salts (e.g. tetraalkylammonium salts, wherein alkyl can be same or different), or agents that complex inorganic cations (e.g. crown ethers or other cryptands). The catalyst cation is not consumed in the reaction although an anion exchange does occur. In particular, suitable phase transfer catalysts to be used according to the present invention are quaternary ammonium salts, for example of the formula $R_m R_n R_j R_k NX$, wherein $R_m R_n R_j R_k$ are, either the same or different, alkyl, and X is halo (eg. chloride, bromide, iodide) or hydroxide, for example, tetra-n-butylammonium hydroxide.

The term "prodrug," as used herein, represents in particular compounds which are transformed in vivo to the parent compound, for example, by hydrolysis in blood, for example as described in T. Higuchi and V. Stella, Pro-drugs as Novel Delivery Systems, Vol. 14 of the A.C.S. Symposium Series, Edward B. Roche, ed., Bioreversible Carriers in Drug Design, American Pharmaceutical Association and Pergamon Press, 1987; H Bundgaard, ed, Design of Prodrugs, Elsevier, 1985; and Judkins, et al. Synthetic Communications, 26(23), 4351-4367 (1996), and "The Organic Chemistry of Drug Design and Drug Action", $2^{nd}$ Edition, R B Silverman (particularly Chapter 8, pages 497 to 557), Elsevier Academic Press, 2004.

Prodrugs therefore include drugs having a functional group which has been transformed into a reversible derivative thereof. Typically, such prodrugs are transformed to the active drug by hydrolysis. As examples may be mentioned the following:

| Functional Group | Reversible derivative |
| --- | --- |
| Carboxylic acid | Esters, including e.g. alkyl esters |
| Alcohol | Esters, including e.g. sulfates and phosphates as well as carboxylic acid esters |
| Amine | Amides, carbamates, imines, enamines, |
| Carbonyl (aldehyde, ketone) | Imines, oximes, acetals/ketals, enol esters, oxazolidines and thiazoxolidines |

Prodrugs also include compounds convertible to the active drug by an oxidative or reductive reaction. As examples may be mentioned:
Oxidative activation
N- and O-dealkylation
Oxidative deamination
N-oxidation
Epoxidation Reductive activation
Azo reduction
Sulfoxide reduction
Disulfide reduction
Bioreductive alkylation
Nitro reduction.

Each of the above described reactions and/or reaction steps can be used individually or in combination in a method to prepare a NEP-inhibitor or a prodrug thereof, such as a NEP inhibitor or prodrug thereof comprising a γ-amino-δ-biphenyl-α-methylalkanoic acid, or acid ester, such as alkyl ester, backbone. In particular the NEP-inhibitor is N-(3-carboxy-1-oxopropyl)-(4S)-p-phenylphenylmethyl)-4-amino-(2R)-methylbutanoic acid or a salt thereof or a prodrug thereof. As described above, WO2008/083967 describes a process for converting a compound of formula (1), as described herein, into a NEP inhibitor or prodrug thereof.

Section C: Examples

The following Examples serve to illustrate the invention without limiting the scope thereof, while they on the other hand represent preferred embodiments of the reaction steps, intermediates and/or the process of the present invention.

Abbreviations:
δ chemical shift
μl microliter
Ac acetyl
AcOH acetic acid
Bn benzyl
Boc tert-butoxycarbonyl
$BF_3 \cdot Et_2O$ boron trifluoride diethyl etherate
$Bu_4NOH$ tetra-n-butylammonium hydroxide
t-BuOK potassium tert-butoxide
$BOC_2O$ di-tert-butyl carbonate
$CO_2$ carbon dioxide
$CH_2O$ formaldehyde
DBU 1,8-diazabicyclo[5,4,0]undec-7-ene
DME 1,2-dimethoxyethane
DMPU 1,3-dimethyl-3,4,56-tetrahedrao-2(1H)-pyrimidinone
de diastereomeric excess
dr diasteremomeric ratio
DMF=dmf N,N-dimethylformamide
DMSO dimethylsulfoxide
ee enantiomeric excess
ES electrospray
ESI electrospray ionisation
Et ethyl
EtOAc ethyl acetate
EtOH ethanol
h hour(s)
HNMR proton nuclear magnetic resonance
$HCl_{(aq)}$ hydrogen chloride aqueous solution
HMDS 1,1,1,3,3,3-hexamethyldisilazane
HPLC high performance liquid chromatography
iPr isopropyl
$iPr_2NEt$ N-ethyldiidopropylamine
iPrOAc isopropyl acetate
iPrOH isopropanol
IR infra red
$K_2CO_3$ potassium carbonate
L liter
LC-MS liquid chromatography-mass spectrometry
LiCl lithium chloride
LDA lithium diisopropylamide
LHMDS lithium bis(trimethylsilyl)amide
M molarity
MeONa sodium methoxide
$MgSO_4$ magnesium sulfate
m/e mass-to-charge ratio
Me methyl
MeOH methanol
mg milligram
min minute(s)
ml milliliter
mmol(s) millimole(s)
mol(s) mole(s)
MS mass spectrometry
$N_2$ nitrogen
$Na_2CO_3$ sodium carbonate
$Na_2SO_3$ sodium sulfite
$Na_2SO_4$ sodium sulfate
$NH_4Cl$ ammonium chloride
nm nanometer
NMR nuclear magnetic resonance
Ph phenyl
Piv pivaloyl
Piv-Cl pivaloyl chloride
ppm parts per million
PPTS pyridinium p-toluenesulfonate
pyr pyridine
RT=rt=r.t. room temperature
TBAH tetra-n-butylammonium hydroxide
tBu tertiary-butyl
TFA trifluoroacetic acid
THF tetrahydrofuran
TLC thin layer chromatography
Tol toluene
$t_R$ retention time
Xyl xylene In quoting NMR data, the following abbreviations may be used: s, singlet; d, doublet; t, triplet; q, quartet; quint., quintet; m, multiplet.

EXAMPLE 1

S)-5-Biphenyl-4-ylmethyl-1-(4-methoxy-benzyl)-pyrrolidin-2-one (3a, R1=p-methoxybenzyl

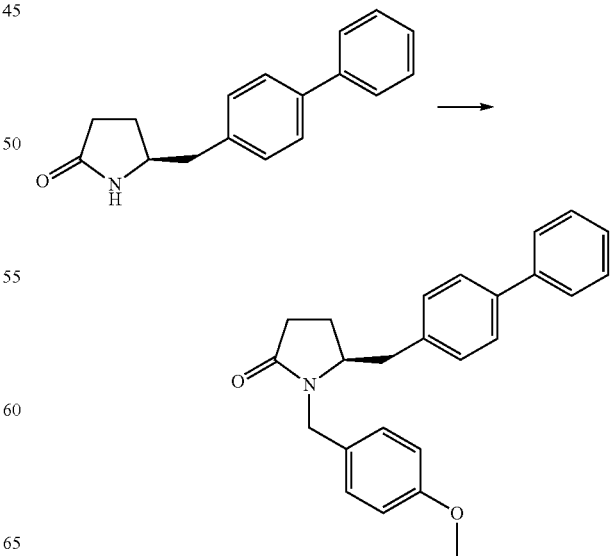

Under N₂, sodium hydride (55%, 6.9 g, 158 mmol) is added to the mixture of (S)-5-biphenyl-4-ylmethylpyrrolidin-2-one (3a, R1=H) (36 g, 143 mmol) in 400 mL dry dimethylformamide at r.t., then 4-methoxybenzyl chloride (24.7 g, 158 mmol) is added. The reaction mixture is heated to 55° C. and stirred for 3 h. Cooled to r.t., 5 mL AcOH is added, and stirred for another 15 min, then dimethylformamide is removed, the residue is redissolved in 400 mL ethyl acetate, washed with water, dried with sodium sulfate. The solvent is removed, the residue is redissolved in 100 mL tert-butylmethylether, cooled to 0° C. and stirred for 5 h, filtered, and dried to afford (S)-5-biphenyl-4-ylmethyl-1-(4-methoxy-benzyl)-pyrrolidin-2-one (3a, R1=p-methoxybenzyl). ¹HNMR (400 MHz, CDCl₃): 1.78 (m, 1H, 3-CHH), 1.90 (m, 1H, 3-CHH), 2.28 (m, 2H, 2-CH₂), 2.59 (dd, 1H, 5-CHH), 3.05 (dd, 1H, 5-CHH), 3.80 (s, 3H, OCH₃), 3.98 (d, 1H, CHH), 5.05 (d, 1H, CHH), 6.80~7.40 (13H, m, aromatic).

HPLC Method

Column: Eclipse XDB-C18; 150×4.6 mm; 5 μm. Mobile Phase A (0.1% H₃PO₄) in water; Mobile Phase B (Acetonitrile). Gradient: 0 min (90% B); 10 min (95% B); 15 min (95% B). Flow rate: 0.7 ml min⁻¹. Wavelength: 210 nm. Temperature: 30° C.

Retention time: 12.5 min (3a, R1=p-methoxybenzyl)

EXAMPLE 2

S)-1-Benzoyl-5-biphenyl-4-ylmethyl-pyrrolidin-2-one (3a, R1=benzoyl

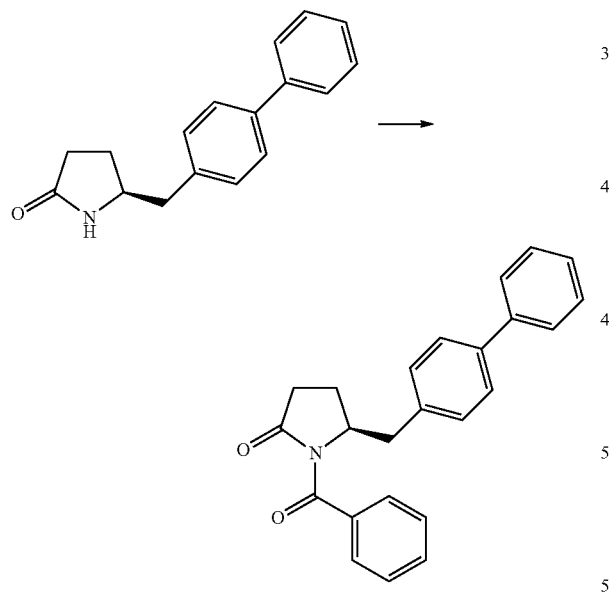

A mixture of (S)-5-Biphenyl-4-ylmethyl-pyrrolidin-2-one (3a, R1=H) (10 g, 40 mmol) and triethylamine (16.6 mL, 120 mmol) is heated to 60° C., benzoyl chloride (8.5 g, 60 mmol) is added over 1 hour, after a further 4 hours, citric acid solution (23.7 g in 100 mL water) is added and the aqueous layer is wash with toluene, the organic portions are combined, washed with water, the mixture is concentrated in vacuo, and redissolved in tert-butylmethylether, and cooled in ice water batch, stirred for 4 hours, and filtered to afford (S)-1-Benzoyl-5-biphenyl-4-ylmethyl-pyrrolidin-2-one (3a, R1=benzoyl). 1HNMR (400 MHz, CDCl₃): 1.94 (m, 1H, 3-CHH), 2.13 (m, 1H, 3-CHH), 2.20 (m, 1H, 2-CHH), 2.23 (m, 1H, 2-CHH), 2.71 (d, 1H, 5-CHH), 2.96 (d, 1H, 5-CHH), 4.38 (m, 1H, 4-CH), 7.20~8.10 (14H, m, aromatic).

HPLC Method

Column: Eclipse XDB-C18; 150×4.6 mm; 5 μm. Mobile Phase A (0.1% H₃PO₄) in water; Mobile Phase B (Acetonitrile). Gradient: 0 min (90% B); 10 min (95% B); 15 min (95% B). Flow rate: 0.7 ml min⁻¹. Wavelength: 210 nm. Temperature: 30° C.

Retention time: 13.0 min (3a, R1=benzoyl)

EXAMPLE 3

S)-5-Biphenyl-4-ylmethyl-1-((E)-styryl)-pyrrolidin-2-one (3a, R1=styryl

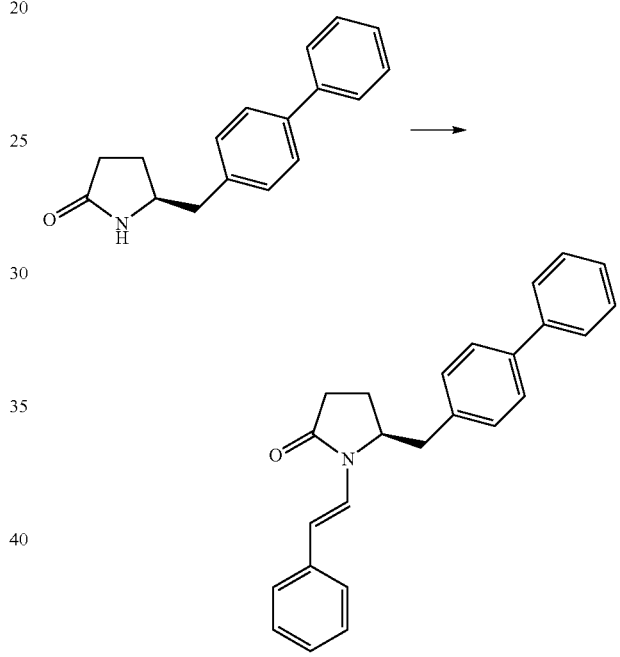

Method 1

(S)-5-Biphenyl-4-ylmethyl-pyrrolidin-2-one (3a, R1=H) (10.0 g, 39.8 mmol) is dissolved in 100 mL of anhydrous tetrahydrofuran, phenylacetaldehyde (5.3 g, 39.8 mmol) and P₂O₅ (6.2 g, 43.8 mmol) are added sequentially, the reaction mixture is refluxed for 12 h. The reaction mixture is cooled to room temperature, filtered, and the cake is washed with ethyl acetate, the filtrate is washed with 10% sodium bicarbonate aqueous solution and brine, dried over anhydrous Na₂SO₄ and concentrate under vacuum, the residue is recrystallized from tert-butylmethylether to obtain (S)-5-Biphenyl-4-ylmethyl-1-((E)-styryl)-pyrrolidin-2-one (3a, R1=styryl). ¹HNMR (400 MHz, CDCl₃): 2.11 (m, 1H, 3-CHH), 2.16 (m, 2H, 5-CH₂), 2.29 (m, 1H, 3CHH), 2.95 (d, 1H, 5-CH₂), 3.10 (d, 1H, 5-CH₂), 4.37 (m, 1H, 4-CH), 6.10 (d, 1H, C=CHH), 7.21~7.65 (15H, m, aromatic+C=CHH), Method 2

(S)-5-Biphenyl-4-ylmethyl-pyrrolidin-2-one (3a, R1=H) (10.0 g, 39.8 mmol) is dissolved in 40 mL of anhydrous toluene, phenylacetaldehyde (5.3 g, 39.8 mmol) and TsOH*H₂O (0.2 g, 1 mmol) are added. The reaction flask is fitted with a Dean-stark trap and condenser, the reaction mixture is refluxed under nitrogen atmosphere for 12 h. The reaction mixture is cooled to room temperature, 100 mL of ethyl acetate is added, the organic layer is washed with saturated sodium hydrogen carbonate aqueous solution, followed by Na₂SO₃ solution and brine, the organic layer is then dried over anhydrous Na₂SO₄ and concentrate under vacuum, the residue is purified by flash chromatography to obtain (S)-5-Biphenyl-4-ylmethyl-1-((E)-styryl)-pyrrolidin-2-one (3a, R1=styryl). Spectroscopic data as Example 2, Method 1.

Method 3

(S)-5-Biphenyl-4-ylmethyl-pyrrolidin-2-one (3a, R1=H) (50.2 g, 200 mmol) is dissolved in 150 mL of p-xylene, add phenylacetaldehyde (26.4 g, 220 mmol) and TsOH*H₂O (0.4 g, 2 mmol). The reaction flask is fitted with a Dean-stark trap and condenser, reflux under nitrogen atmosphere overnight. The reaction mixture is cooled to room temperature, stir at 0° C. for 1 h, then filter, the cake is washed with cooled tert-butylmethylether three time (3×20 mL), dry under high vacuum to obtain (S)-5-Biphenyl-4-ylmethyl-1-((E)-styryl)-pyrrolidin-2-one (3a, R1=styryl) as white solid. Spectroscopic data as Example 2, Method 1.

Method 4

(S)-5-Biphenyl-4-ylmethyl-pyrrolidin-2-one (3a, R1=H) (5.02 g, 20 mmol) is dissolved in 50 mL of toluene, add phenylacetaldehyde dimethylacetal (3.77 g, 22 mmol) and TsOH*H₂O (0.1 g, 0.5 mmol). The reaction flask is fitted with a Dean-stark trap and condenser, reflux under nitrogen atmosphere overnight. The reaction mixture is cooled to room temperature, add 50 mL of ethyl acetate, stir for 10 min to obtain a clear solution, wash with saturated sodium hydrogen carbonate aqueous solution, saturated Na₂SO₃ aqueous and brine, the organic extracts are dried over anhydrous Na₂SO₄ and the solvent is evaporated under vacuum, the residue is purified by flash chromatography to obtain (S)-5-Biphenyl-4-ylmethyl-1-((E)-styryl)-pyrrolidin-2-one (3a, R1=styryl) as white solid. Spectroscopic data as Example 2, Method 1.

Method 5

(S)-5-Biphenyl-4-ylmethyl-pyrrolidin-2-one (3a, R1=H) (5.02 g, 20 mmol) is dissolved in 50 mL of toluene, and phenylacetaldehyde dimethylacetal (3.77 g, 22 mmol) and PPTS (0.13 g, 0.5 mmol) are added. The reaction flask is fitted with a Dean-stark trap and condenser, reflux under nitrogen atmosphere overnight. The reaction mixture is cooled to room temperature, add 50 mL of ethyl acetate, stir for 10 min to obtain a clear solution, wash with saturated sodium hydrogen carbonate aqueous solution, saturated Na₂SO₃ aqueous and brine, the organic phase is dry over anhydrous NaSO₄ and evaporate the solvent under vacuum, the residue is purified by flash chromatography to give (S)-5-Biphenyl-4-ylmethyl-1-((E)-styryl)-pyrrolidin-2-one (3a, R1=styryl) as white solid. Spectroscopic data as Example 2, Method 1.

HPLC Method (Methods 1-6)

Column: Eclipse XDB-C18; 150×4.6 mm; 5 μm. Mobile Phase A (0.1% H₃PO₄) in water; Mobile Phase B (Acetonitrile). Gradient: 0 min (30% B); 8 min (95% B); 15 min (95% B). Flow rate: 1.0 ml min⁻¹. Wavelength: 210 nm. Temperature: 30° C.

Retention time: 12.3 min (3a, R1=styryl)

EXAMPLE 4

S)-5-Biphenyl-4-ylmethyl-1-((E)-but-1-enyl)-pyrrolidin-2-one (3a, R1=1-butenyl

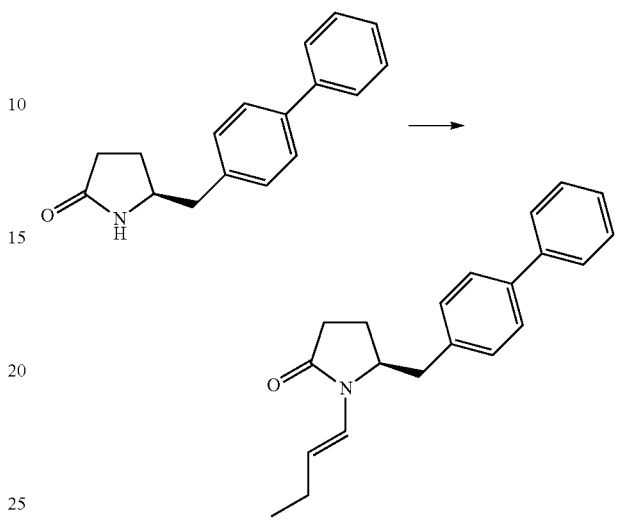

Method 1

(S)-5-biphenyl-4-ylmethyl-pyrrolidin-2-one (3a, R1=H) (10.0 g, 39.8 mmol) is dissolved in 100 mL of anhydrous tetrahydrofuran, butylaldehyde (2.9 g, 39.8 mmol) and phosphorus pentoxide (6.2 g, 43.2 mmol) are added sequentially, the reaction mixture is refluxed under for 12 h. The reaction mixture is cooled to room temperature, filtered and washed with ethyl acetate, the filtrate is washed with 10% sodium hydrogen carbonate aqueous solution followed by brine. The organic layer is dried over anhydrous Na₂SO₄ and concentrated under vacuum, the residue is purified by flash column chromatography heptane/ethyl acetate=10:1 to afford (S)-5-Biphenyl-4-ylmethyl-1-((E)-styryl)-pyrrolidin-2-one (3a, R1=1-butenyl). ¹HNMR (400 MHz, CDCl₃): 1.07 (t, 3H, CH₃H), 2.12 (m, 2H, CH₂H), 2.20 (m, 2H, 3-CH₂), 2.35 (m, 2H, 2-CH₂), 2.95 (m, 1H, 5-CH₂), 3.13 (m, 1H, 5-CH₂), 4.14 (m, 1H, 4-CH), 5.27 (m, 1H, CH=CH), 6.85 (d, 1H, HC=CH—N), 7.14~7.51 (9H, m, aromatic).

Method 2

(S)-5-biphenyl-4-ylmethyl-pyrrolidin-2-one (3a, R1=H) (5.02 g, 20 mmol) is dissolved in 50 mL of toluene, add butylaldehyde (1.44 g, 20 mmol) and TsOH*H₂O (50 mg, 0.3 mmol). The reaction flask is fitted with a Dean-stark trap and condenser, reflux under nitrogen atmosphere overnight. The reaction mixture is cooled to room temperature, add 50 mL of toluene, stir for 10 mins to obtain a clear solution, washed with saturated sodium hydrogen carbonate aqueous solution, saturated Na₂SO₃ aqueous and brine, the organic phase is dried over anhydrous Na₂SO₄ and evaporate the solvent under vacuum, the residue is purified by flash chromatography to obtain (S)-5-Biphenyl-4-ylmethyl-1-((E)-but-1-enyl)-pyrrolidin-2-one (3a, R1=1-butenyl). Spectroscopic data as Example 4, Method 1.

Method 3

(S)-5-Biphenyl-4-ylmethyl-pyrrolidin-2-one (3a, R1=H) (5.02 g, 20 mmol) is dissolved in 50 mL of toluene, add butylaldehyde (1.44 g, 20 mmol) and BF₃-Et₂O (0.5 mL). The reaction flask is fitted with a Dean-stark trap and condenser, reflux under nitrogen atmosphere overnight. The reaction mixture is cooled to room temperature, add 50 mL of toluene, stir for 10 min to obtain a clear solution, wash with saturated sodium hydrogen carbonate aqueous solution, saturated Na$_2$SO$_3$ aqueous and brine, the organic phase is dry over anhydrous Na$_2$SO$_4$ and evaporate the solvent under vacuum, the residue is purified by flash chromatography to obtain (S)-5-Biphenyl-4-ylmethyl-1-((E)-but-1-enyl)-pyrrolidin-2-one (3a, R1=1-butenyl). Spectroscopic data as Example 4, Method 1.

Method 4

(S)-5-Biphenyl-4-ylmethyl-pyrrolidin-2-one (3a, R1=H) (5.0 g, 20 mmol) is dissolved in 50 mL of tetrahydrofuran, add butylaldehyde diethylacetal (3.2 g, 22 mmol) and PPTS (215 mg, 1 mmol). The reaction flask is fitted with distillation equipment and condenser to remove the ethanol produce in the reaction, reflux under nitrogen atmosphere overnight. The reaction mixture is cooled to room temperature, add 50 mL of toluene, wash with saturated sodium hydrogen carbonate aqueous solution, saturated Na$_2$SO$_3$ aqueous and brine, the organic phase is dried over anhydrous Na$_2$SO$_4$ and evaporate the solvent under vacuum, the residue is purified by flash chromatography to obtain (S)-5-Biphenyl-4-ylmethyl-1-((E)-but-1-enyl)-pyrrolidin-2-one (3a, R1=1-butenyl). Spectroscopic data as Example 4, Method 1.

Method 5

(S)-5-Biphenyl-4-ylmethyl-pyrrolidin-2-one (3a, R1=H) (5.0 g, 20 mmol) is dissolved in 50 mL of toluene, add butylaldehyde diethylacetal (3.2 g, 22 mmol) and PPTS (215 mg, 1 mmol). The reaction flask is fitted with distillation equipment and condenser to remove the ethanol produced in the reaction, heat to reflux under nitrogen atmosphere overnight. The reaction mixture is cooled to room temperature, add 50 mL of toluene, washed with saturated sodium hydrogen carbonate aqueous solution, saturated Na$_2$SO$_3$ aqueous and brine, the organic phase is dry over anhydrous Na$_2$SO$_4$ and evaporate the solvent under vacuum, the residue is purified by flash chromatography to give (S)-5-Biphenyl-4-ylmethyl-1-((E)-but-1-enyl)-pyrrolidin-2-one (3a, R1=1-butenyl). Spectroscopic data as Example 4, Method 1.

HPLC Method (Methods 1-5)

Column: Eclipse XDB-C18; 150×4.6 mm; 5 μm. Mobile Phase A (0.1% H$_3$PO$_4$) in water; Mobile Phase B (Acetonitrile). Gradient: 0 min (30% B); 8 min (95% B); 15 min (95% B). Flow rate: 1.0 ml min$^{-1}$. Wavelength: 210 nm. Temperature: 30° C.

Retention time: 9.5 min (3a, R1=1-butenyl)

EXAMPLE 5

3R/S)-Benzoyl-(5S)-biphenyl-4-ylmethyl-2-oxo-pyrrolidine-1-carboxylic acid tert-butyl ester (4a, R1=t-butoxycarbonyl, R4=phenyl

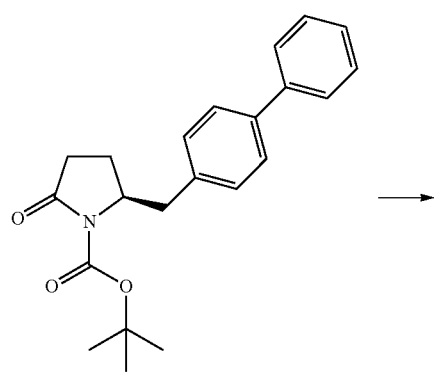

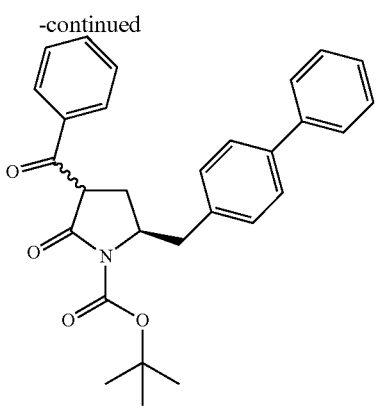

Method 1

Under N$_2$, n-butyllithium (56 mL, 2.5 M in hexane, 0.14 mol) is added to the mixture of HMDS (24.2 g, 0.15 mol) in 300 mL dry tetrahydrofuran at −10° C., the resulting mixture is then stirred for 30 min at −10° C. A mixture of (S)-2-Biphenyl-4-ylmethyl-5-oxo-pyrrolidine-1-carboxylic acid tert-butyl ester (3a, R1=t-butoxycarbonyl) (35.1 g, 0.1 mol) in 50 mL dry tetrahydrofuran is added to the reaction mixture at −10° C., after about 30 min, n-butyllithium (40 mL, 2.5 M in hexane, 0.1 mol) is added to the reaction mixture at −10° C., the resulting mixture is then stirred for 30 min at −10° C. Benzoyl chloride (15.5 g, 0.11 mol) is added to the reaction mixture at −10° C., after about 1 hour at −10° C., the reaction mixture is diluted with 100 mL saturated aqueous ammonium chloride solution and stirred for 15 min, stop stirring, and remove the lower aqueous layer, the organic phase is then concentrated in vacuo. Ethyl acetate (200 mL) is added, filtered and the filtrate concentrated to give (R/S)-3-Benzoyl-(S)-5-biphenyl-4-ylmethyl-2-oxo-pyrrolidine-1-carboxylic acid tert-butyl ester (4a, R1=t-butoxycarbonyl, R4=phenyl), the ratio of (3S,5R):(3R,5R) is 70:30 as determined by HPLC. $^1$HNMR (400 MHz, DMSO): 1.52 (s, 9H, (CH$_3$)$_3$), 2.05 (m, 1H, 3-CHH), 2.60 (m, 1H, 3CHH), 2.96 (m, 1H, 5-CHH), 3.13 (m, 1H, 5-CHH), 4.21 (m, 1H, 2-CH), 4.53 (m, 1H, 4-CH), 7.10~8.10 (14H, m, aromatic).

Method 2

Under N$_2$, n-butyllithium (2.4 mL, 2.5 M in hexane, 6 mmol) is added to the mixture of Diisopropylamine (0.71 g, 7 mmol) in 20 mL dry tetrahydrofuran at −10° C., the resulting mixture is then stirred for 30 min at −10° C. A mixture of (S)-2-Biphenyl-4-ylmethyl-5-oxo-pyrrolidine-1-carboxylic acid tert-butyl ester (3a, R1=t-butoxycarbonyl) (1.76 g, 5 mmol) in 5 mL dry tetrahydrofuran is added to the reaction mixture at −10° C., after about 30 min, n-butyllithium (2 mL, 2.5 M in hexane, 5 mmol) is added to the reaction mixture at −10° C., the resulting mixture is then stirred for 30 min at −10° C. Benzoyl chloride (0.77 g, 5.5 mmol) is added to the reaction mixture at −10° C., after about 1 hour at −10° C., the reaction mixture is diluted with 100 mL saturated aqueous ammonium chloride solution and stirred for 15 min, stop stirring, and remove the lower aqueous layer. the organic phase is then concentrated in vacuo. ethyl acetate 20 mL is added, filtered and the filtrate concentrated to give (R/S)-3-Benzoyl-(S)-5-biphenyl-4-ylmethyl-2-oxo-pyrrolidine-1-carboxylic acid tert-butyl ester (4a, R1=t-butoxycarbonyl, R4=phenyl). the ratio of (3S,5R):(3R,5R) is 70:30 as determined by HPLC. Spectroscopic data as Example 5, Method 1.

Method 3

Under N$_2$, LHMDS (132 mL, 1.0 M in tetrahydrofuran, 132 mmol) is added to the mixture of (S)-2-Biphenyl-4-ylmethyl-5-oxo-pyrrolidine-1-carboxylic acid tert-butyl ester (3a, R1=t-butoxycarbonyl) (21.06 g, 60 mmol) in 150 mL dry tetrahydrofuran is added to the reaction mixture at −10° C., the resulting mixture is then stirred for 30 min at −10° C. Benzoyl chloride (9.28 g, 66 mmol) is added to the reaction mixture at −10° C., after about 1 hour at −10° C., the reaction mixture is diluted with 50 mL saturated aqueous ammonium chloride solution and stirred for 15 min, stop stirring, and remove the lower aqueous layer. the organic phase is then concentrated in vacuo. ethyl acetate 100 mL is added, filtered and the filtrate concentrated to give (R/S)-3-Benzoyl-(S)-5-biphenyl-4-ylmethyl-2-oxo-pyrrolidine-1-carboxylic acid tert-butyl ester (4a, R1=t-butoxycarbonyl, R4=phenyl). the ratio of (3S,5R):(3R,5R) is 70:30 as determined by HPLC. Spectroscopic data as Example 5, Method 1.

Method 4

Under $N_2$, (S)-2-Biphenyl-4-ylmethyl-5-oxo-pyrrolidine-1-carboxylic acid tert-butyl ester (3a, R1=t-butoxycarbonyl) (1.4 g, 4 mmol) is dissolved in 4 mL toluene, and heated to reflux, sodium hydride (55% in mineral oil, 0.23 g, 5.2 mmol) was added, and stirred for 2 hours at reflux, then benzoyl chloride (0.62 g, 4.4 mmol) is added to the reaction mixture, the resulting mixture is then stirred for 2 hours at reflux. the reaction mixture is diluted with 5 mL saturated aqueous ammonium chloride solution and stirred for 15 min, stop stirring, and remove the lower aqueous layer. the organic phase is concentrated to dryness, the residue is purified by column chromatography (ethyl acetate/heptane=1/2) to give (R/S)-3-Benzoyl-(S)-5-biphenyl-4-ylmethyl-2-oxo-pyrrolidine-1-carboxylic acid tert-butyl ester (4a, R1=t-butoxycarbonyl, R4=phenyl). the ratio of (3S,5R):(3R,5R) is 70:30 as determined by HPLC. Spectroscopic data as Example 5, Method 1.

Method 5

Under $N_2$, to a solution of (S)-2-Biphenyl-4-ylmethyl-5-oxo-pyrrolidine-1-carboxylic acid tert-butyl ester (3a, R1=t-butoxycarbonyl) (10 g, 28.49 mmol) in THF (56 mL) is added $MgCl_2$ (2.56 g, 28.49 mmol) and triethylamine (8.63 g, 85.47 mmol). The mixture is cooled to 5° C., stirred for 10 min, then benzoyl chloride (6.40 g, 45.58 mmol) is added dropwise. The reaction mixture is stirred at 5° C. for 1 h, then the temperature is warmed up to 10° C. After stirring for 15 h, 20 mL of water are added, followed by a solution of $H_3PO_4$ (12.0 g) in water (20 mL). The aqueous phase is then removed, the organic phase is washed with brine (40 mL) twice, the organic extracts are concentrated under vacuum to give (R/S)-3-Benzoyl-(S)-5-biphenyl-4-ylmethyl-2-oxo-pyrrolidine-1-carboxylic acid tert-butyl ester (4a, R1=t-butoxycarbonyl, R4=phenyl). The ratio of (3S,5R):(3R,5R) is 70:30 as determined by HPLC. Spectroscopic data as Example 5, Method 1.

HPLC Method (Methods 1-5)

Column: Eclipse XDB-C18; 150×4.6 mm; 5 μm. Mobile Phase A (0.1% $H_3PO_4$) in water; Mobile Phase B (Acetonitrile). Gradient: 0 min (30% B); 8 min (95% B); 15 min (95% B). Flow rate: 1.0 ml min$^{-1}$. Wavelength: 210 nm. Temperature: 30° C.

Retention time:

10.3 min (3S,5R-4, R1=t-butoxycarbonyl, R4=phenyl)

10.5 min (3R,5R-4, R1=t-butoxycarbonyl, R4=phenyl)

9.2 min (3a, R1=t-butoxycarbonyl)

EXAMPLE 6

R/S)-3-Benzoyl-(S)-5-biphenyl-4-ylmethyl-1-pyrrolidin-1-ylmethyl-pyrrolidin-2-one (4a, R1=pyrrolidinylmethyl, R4=phenyl

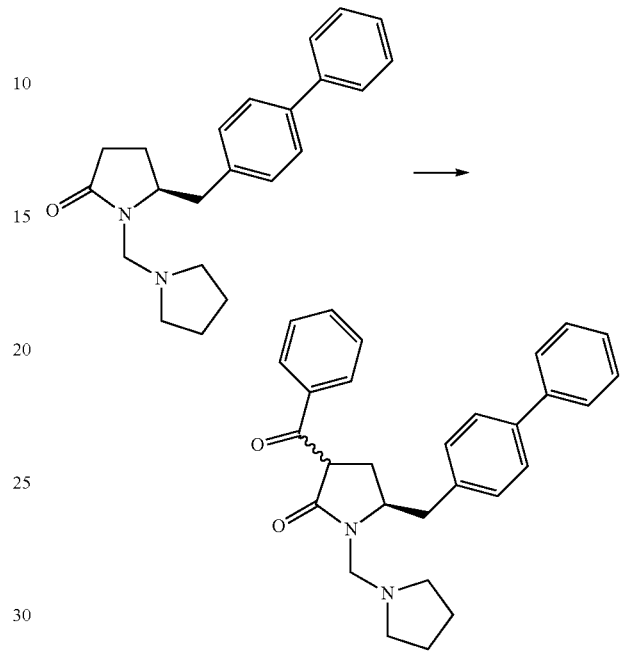

Method 1

Under $N_2$, the mixture of (S)-5-biphenyl-4-ylmethyl-1-pyrrolidin-1-ylmethylpyrrolidin-2-one (3a, R1=pyrrolidinylmethyl) (6.68 g, 20 mmol) and benzoic acid methyl ester (3.0 g, 22 mmol) in 20 mL toluene is heated to reflux, sodium hydride (55% in mineral oil, 1.14 g, 26 mmol) is added, and stirred overnight at reflux. The reaction mixture is diluted with 20 mL saturated aqueous ammonium chloride solution and stirred for 15 min, stop stirring, and remove the lower aqueous layer. the organic phase is concentrated to dryness, the residue was purified by column chromatography (ethyl acetate/heptane=1/1) to give (R/S)-3-Benzoyl-(R)-5-biphenyl-4-ylmethyl-1-pyrrolidin-1-ylmethyl-pyrrolidin-2-one (4a, R1=pyrrolidinylmethyl, R4=phenyl), the ratio of (3S,5R) and (3R,5R) is 60:40 as determined by HPLC. $^1$HNMR (400 MHz, $CDCl_3$): 1.68 (m, 4H, 2×$CH_2CH_2$), 1.98 (m, 1H, 3-CHH), 2.23 (m, 1H, 3-CHH), 2.51 (m, 4H, 2×$NCH_2$), 2.65 (dd, 1H, N—CHH), 3.15 (dd, 1H, N—CHH), 2.67 (d, 1H, 5-CHH), 2.92 (d, 1H, 5-CHH), 3.73 (m, 1H, 2-CH), 3.78 (m, 1H, 4-CH), 7.20-8.00 (14H, m, aromatic).

Method 2

Under $N_2$, the mixture of (S)-5-biphenyl-4-ylmethyl-1-pyrrolidin-1-ylmethylpyrrolidin-2-one (3a, R1=pyrrolidinylmethyl) (1.34 g, 4 mmol) and Benzoic acid methyl ester (0.6 g, 4.4 mmol) in 4 mL dimethylformamide is stirring at 20° C., sodium hydride (55% in mineral oil, 0.23 g, 5.2 mmol) was added, and stirred overnight at 110° C. the reaction mixture is diluted with 5 mL saturated aqueous ammonium chloride solution and 10 mL ethyl acetate, stirred for 15 min, stop stirring, and remove the lower aqueous layer. the organic phase is concentrated to dryness, the residue was purified by column chromatography (ethyl acetate/heptane=1/1) to give (R/S)-3-Benzoyl-(R)-5-biphenyl-4-ylmethyl-1-pyrrolidin-1-ylmethyl-pyrrolidin-2-one (4a, R1=pyrrolidinylmethyl, R4=phenyl), the ratio of (3S,5R) and (3R,5R) is 60:40 as determined by HPLC. Spectroscopic data as Example 6, Method 1.

Method 3

Under $N_2$, the mixture of (S)-5-biphenyl-4-ylmethyl-1-pyrrolidin-1-ylmethylpyrrolidin-2-one (3a, R1=pyrrolidinylmethyl) (1.34 g, 4 mmol), DMPU (0.56 g, 4.4 mmol) and benzoic acid methyl ester (0.6 g, 4.4 mmol) in 4 mL dimethylformamide is stirring at 20° C., sodium hydride (55% in mineral oil, 0.23 g, 5.2 mmol) is added, and stirred for 3 hours at 110° C. the reaction mixture is diluted with 5 mL saturated aqueous ammonium chloride solution and 10 mL ethyl acetate, stirred for 15 min, stop stirring, and remove the lower aqueous layer. the organic phase is concentrated to dryness, the residue was purified by column chromatography (ethyl acetate/heptane=1/1) to give (R/S)-3-Benzoyl-(R)-5-biphenyl-4-ylmethyl-1-pyrrolidin-1-ylmethyl-pyrrolidin-2-one (4a, R1=pyrrolidinylmethyl, R4=phenyl), the ratio of (3S,5R) and (3R,5R) is 60:40 as determined by HPLC. Spectroscopic data as Example 6, Method 1.

Method 4

Under $N_2$, the mixture of (S)-5-biphenyl-4-ylmethyl-1-pyrrolidin-1-ylmethylpyrrolidin-2-one (3a, R1=pyrrolidinylmethyl) (1.34 g, 4 mmol), DMPU (0.56 g, 4.4 mmol) and benzoic acid methyl ester (0.6 g, 4.4 mmol) in 4 mL Toluene is stirring at 20° C., sodium hydride (55% in mineral oil, 0.23 g, 5.2 mmol) is added, and stirred for 3 hours at 60° C. the reaction mixture is diluted with 5 mL saturated aqueous ammonium chloride solution and 10 mL ethyl acetate, stirred for 15 min, stop stirring, and remove the lower aqueous layer. The organic phase is concentrated to dryness, the residue was purified by column chromatography (ethyl acetate/heptane=1/1) to give (R/S)-3-Benzoyl-(R)-5-biphenyl-4-ylmethyl-1-pyrrolidin-1-ylmethyl-pyrrolidin-2-one (4a, R1=pyrrolidinylmethyl, R4=phenyl), the ratio of (3S,5R) and (3R,5R) is 60:40 as determined by HPLC. Spectroscopic data as Example 6, Method 1.

HPLC Method (Method 1-4)

Column: Eclipse XDB-C18; 150×4.6 mm; 5 μm. Mobile Phase A (0.1% $H_3PO_4$) in water; Mobile Phase B (Acetonitrile). Gradient: 0 min (90% B); 10 min (95% B); 15 min (95% B). Flow rate: 0.7 ml min$^{-1}$. Wavelength: 210 nm. Temperature: 30° C.

Retention time:
8.6 min (3S,5R-4, R1=pyrrolidinylmethyl, R4=phenyl)
8.8 min (3R,5R-4, R1=pyrrolidinylmethyl, R4=phenyl).
7.5 min (3a, R1=pyrrolidinylmethyl)

EXAMPLE 7

3R/S)-Benzoyl-(5S)-biphenyl-4-ylmethyl-1-(4-methoxy-benzyl)-pyrrolidin-2-one (4a, R1=p-methoxybenzyl, R4=phenyl

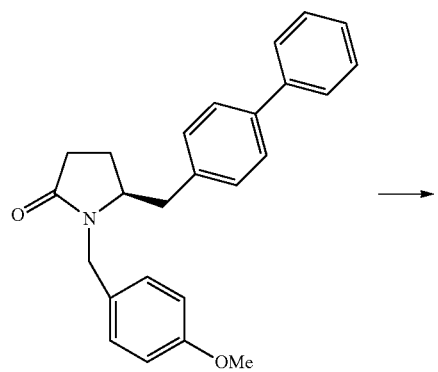

-continued

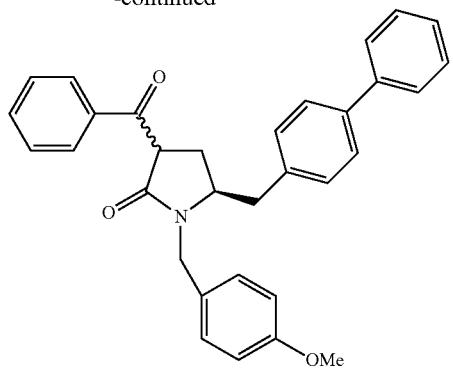

To a suspension of sodium hydride (150 mg, 55% in mineral oil, 3.75 mmol) in toluene (1 mL) is added (5S)-biphenyl-4-ylmethyl-1-(4-methoxybenzyl)pyrrolidin-2-one (3a, R1=p-methoxybenzyl) (694 mg, 1.86 mmol) followed by addition of benzoic acid methyl ester (253 mg, 1.86 mmol), the resulting mixture is then heated at 130° C. for 9 h. After cooling to room temperature, $NH_4Cl$ (sat. aq, 5 mL) is added followed by ethyl acetate (3 mL). The organic layer is separated, washed with brine and concentrated to give (3R/S)-benzoyl-(5S)-biphenyl-4-ylmethyl-1-(4-methoxybenzyl) pyrrolidin-2-one (4a, R1=p-methoxybenzyl, R4=phenyl) as a mixture of (3S,5R) and (3R,5R) diastereomers (50:40 as determined by HPLC). $^1$HNMR (400 MHz, DMSO): 1.82-2.08 (m, 2H), 2.25-2.70 (m, 2H), 3.00-3.26 (m, 2H), 3.73 (s, 3H), 4.00-4.10 (m, 1H), 4.20-4.52 (m, 1H), 4.94-5.09 (m, 1H), 6.86~8.10 (18H, m, aromatic). MS (ESI, m/e) 476 (MH$^+$).

HPLC Method

Column: Eclipse XDB-C18; 150×4.6 mm; 5 μm. Mobile Phase A (0.1% $H_3PO_4$) in water; Mobile Phase B (Acetonitrile). Gradient: 0 min (30% B); 8 min (95% B); 15 min (95% B). Flow rate: 1.0 ml min$^{-1}$. Wavelength: 210 nm. Temperature: 30° C.

Retention time:
10.0 min (3S,5S-4, R1=p-methoxybenzyl, R4=phenyl)
10.1 min (3R,5S-4-a, R1=p-methoxybenzyl, R4=phenyl)
8.8 min (3a, R1=p-methoxybenzyl)

EXAMPLE 8

S)-3-Benzoyl-5-biphenyl-4-ylmethyl-1-((E)-styryl)-pyrrolidin-2-one (4a, R1=styryl, R4=benzyl

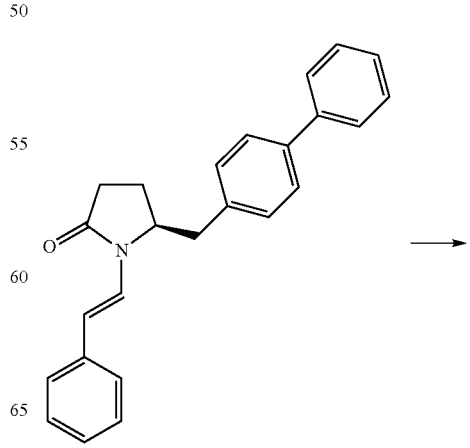

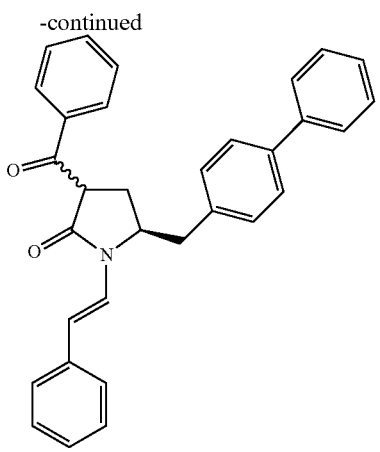

Method 1

(S)-5-Biphenyl-4-ylmethyl-1-((E)-styryl)-pyrrolidin-2-one (3a, R1=styryl) (50.0 g, 141.7 mmol) is heated to dissolve in 140 mL of anhydrous toluene under $N_2$, add sodium hydride (8.04 g, 184.2 mmol) in portions, stir at this temperature for 10 min, then add methyl benzoate dropwise, reflux for 6 h, cool to room temperature, quench with saturated $NH_4Cl$ aqueous solution, separate the organic phase, extract with toluene (100 mL*3), the combined organic extracts are washed with saturated $Na_2CO_3$ aqueous solution and brine, dry over anhydrous $Na_2SO_4$ and concentrate under vacuum to obtain (S)-3-Benzoyl-5-biphenyl-4-ylmethyl-1-((E)-styryl)-pyrrolidin-2-one (4a, R1=styryl, R4=phenyl), the ratio of (3S,5S) to (3R,5S) is 70:30 as determine by HPLC. 1HNMR (400 MHz, $CDCl_3$): 2.35 (m, 1H, 3-CHH), 3.26 (m, 3H, 5-$CH_2$+3-CHH), 3.74 (m, 1H, 2-CH), 4.32 (m, 1H, 4-CH), 6.21 (m, 1H, C=CHH), 7.21~7.80 (m, 20H, aromatic+C=CHH).

Method 2

(S)-5-Biphenyl-4-ylmethyl-1-((E)-styryl)-pyrrolidin-2-one (3a, R1=styryl) (10.0 g, 28.3 mmol) is heated to dissolve in 30 mL of anhydrous toluene under $N_2$, add MeONa (1.99 g, 36.8 mmol) in one portion, stir at this temperature for 10 min, then add methyl benzoate dropwise, reflux overnight, cool to room temperature, quench with saturated $NH_4Cl$ aqueous solution, separate the organic phase, extract with toluene (15 mL*3), the combined organic extracts are washed with saturated $Na_2CO_3$ aqueous solution and brine, dry over anhydrous $Na_2SO_4$ and concentrate under vacuum. The residue is purified by silica gel column chromatography, eluting with 5:1 heptane/ethyl acetate to give (S)-3-Benzoyl-5-biphenyl-4-ylmethyl-1-((E)-styryl)-pyrrolidin-2-one (4a, R1=styryl, R4=phenyl), the ratio of (3S,5S) to (3R,5S) is 70:30 as determine by HPLC. Spectroscopic data as Example 8, Method 1.

Method 3

(S)-5-Biphenyl-4-ylmethyl-1-((E)-styryl)-pyrrolidin-2-one (3a, R1=styryl) (1.00 g, 2.8 mmol) is heated to dissolve in 3 mL of anhydrous toluene under $N_2$, add t-BuOK (0.43 g, 3.7 mmol) in one portion, stir at this temperature for 10 min, then add methyl benzoate dropwise, the reaction mixture reflux overnight, cool to room temperature, quench with saturated $NH_4Cl$ aqueous solution, separate the organic phase, extract with toluene (30 mL*3), the combined organic extracts are washed with saturated $Na_2CO_3$ aqueous solution and brine, dry over anhydrous $Na_2SO_4$ and concentrate under vacuum. The residue is purified by silica gel column chromatography, eluting with 5:1 heptane/ethyl acetate to obtain (S)-3-Benzoyl-5-biphenyl-4-ylmethyl-1-((E)-styryl)-pyrrolidin-2-one (4a, R1=styryl, R4=phenyl), the ratio of (3S,5S) to (3R,5S) is 70:30 as determine by HPLC. Spectroscopic data as Example 8, Method 1.

HPLC Method (Methods 1-3)

Column: Eclipse XDB-C18; 150×4.6 mm; 5 μm. Mobile Phase A (0.1% $H_3PO_4$) in water; Mobile Phase B (Acetonitrile). Gradient: 0 min (30% B); 8 min (95% B); 15 min (95% B). Flow rate: 1.0 ml min$^{-1}$. Wavelength: 210 nm. Temperature: 30° C.

Retention time:
10.7 min (3S,5S-4, R1=styryl, R4=phenyl)
11.0 min (3R,5S-4, R1=styryl, R4=phenyl)
12.3 min (3a, R1=styryl)

EXAMPLE 9

S)-3-Benzoyl-5-biphenyl-4-ylmethyl-1-((E)-but-1-enyl)-pyrrolidin-2-one (4a, R1=1-butenyl, R4=phenyl Sodium hydride (2.03 g, 46.4 mmol) is suspended in 40-mL of anhydrous toluene, heat to reflux under nitrogen atmosphere, add a mixture solution of (S)-5-Biphenyl-4-ylmethyl-1-((E)-but-1-enyl)-pyrrolidin-2-one (3a, R1=1-butenyl) (11.02 g, 35.67 mmol) and methyl benzoate (4.86 g, 35.67 mmol) in anhydrous toluene dropwise, the reaction mixture is refluxed for 4 h, cool to ambient temperature, quench with saturated $NH_4Cl$ aqueous solution, extracted with toluene, the combined organic extracts are washed with saturated $Na_2CO_3$ and brine, dry over anhydrous $Na_2SO_4$, concentrate under vacuum to obtain (S)-3-Benzoyl-5-biphenyl-4-ylmethyl-1-((E)-but-1-enyl)-pyrrolidin-2-one (4a, R1=1-butenyl, R4=benzyl), which is directly used in the next step. 1HNMR (400 MHz, $CDCl_3$): 1.07 (t, 3H, $CH_3H$), 2.12 (m, 2H, $CH_2H$), 2.20 (m, 2H, 3-$CH_2$), 2.95 (m, 1H, 5-$CH_2$), 3.13 (m, 1H, 5-$CH_2$), 3.82 (m, H, 2-$CH_2H$), 4.14 (m, 1H, 4-CH), 5.27 (m, 1H, CH=CH), 6.85 (d, 1H, HC=CH—N), 7.14~8.20 (14H, m, aromatic). the ratio of (3S,5S) to (3R,5S) is 60:40 as determined by HPLC.

HPLC Method

Column: Eclipse XDB-C18; 150×4.6 mm; 5 μm. Mobile Phase A (0.1% $H_3PO_4$) in water; Mobile Phase B (Acetonitrile). Gradient: 0 min (30% B); 8 min (95% B); 15 min (95% B). Flow rate: 1.0 ml $min^{-1}$. Wavelength: 210 nm. Temperature: 30° C.

Retention time:
10.5 min (3S,5S-4, R1=1-butenyl, R4=phenyl)
10.8 min (3R,5S-4, R1=1-butenyl, R4=phenyl).
9.5 min (3a, R1=1-butenyl)

EXAMPLE 10

R/S)-1,3-Dibenzoyl-(S)-5-biphenyl-4-ylmethyl-pyrrolidin-2-one (4a, R1=benzoyl, R4=phenyl

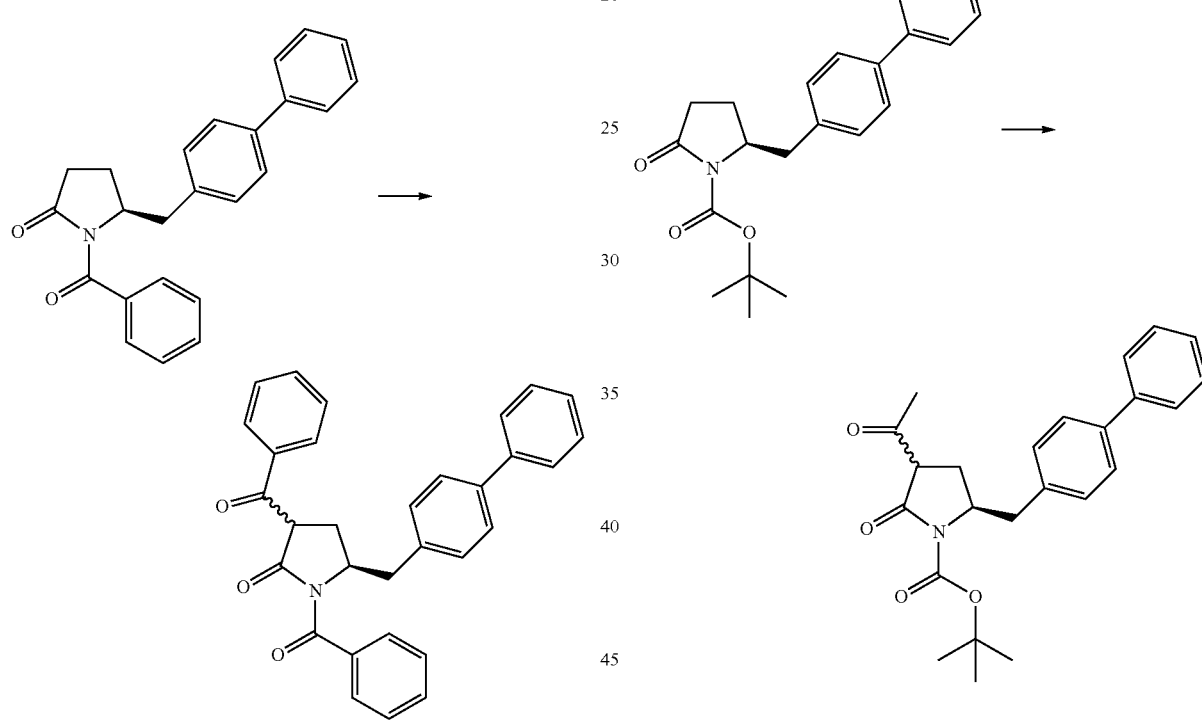

Under $N_2$, 1-benzoyl-(S)-5-biphenyl-4-ylmethyl-pyrrolidin-2-one (3a, R1=benzoyl) (1.34 g, 4 mmol) is dissolved in 4 mL toluene, and heated to reflux, sodium hydride (55% in mineral oil, 0.23 g, 5.2 mmol) is added, and stirred for 2 hours at reflux, then benzoyl chloride (0.62 g, 4.4 mmol) is added to the reaction mixture, the resulting mixture is then stirred for 2 hours at reflux. the reaction mixture is diluted with 5 mL saturated aqueous ammonium chloride solution and stirred for 15 min, stop stirring, and remove the lower aqueous layer. The organic phase is concentrated to dryness, the residue is purified by column chromatography (ethyl acetate/heptane=1/2) to yield (R/S)-1,3-Dibenzoyl-(S)-5-biphenyl-4-ylmethyl-pyrrolidin-2-one (4a, R1=benzoyl, R4=phenyl), the ratio of (3S,5S) to (3R,5S) is 30:70 as determined by HPLC. $^1$HNMR (400 MHz, $CDCl_3$): 2.09 (m, 1H, 3-CHH), 2.34 (m, 1H, 3-CHH), 2.71 (d, 1H, 5-CHH), 2.96 (d, 1H, 5-CHH), 3.73 (m, 1H, 2-CH), 4.38 (m, 1H, 4-CH), 7.20~8.10 (19H, m, aromatic).

HPLC Method

Column: Eclipse XDB-C18; 150×4.6 mm; 5 μm. Mobile Phase A (0.1% $H_3PO_4$) in water; Mobile Phase B (Acetonitrile). Gradient: 0 min (30% B); 8 min (95% B); 15 min (95% B). Flow rate: 1.0 ml $min^{-1}$. Wavelength: 210 nm. Temperature: 30° C.

Retention time:
11.0 min (3S,5S-4, R1=benzoyl, R4=phenyl)
11.1 min (3R,5S-4, R1=benzoyl, R4=phenyl)
9.3 min (3a, R1=benzoyl)

EXAMPLE 11

R/S)-3-Acetyl-(S)-5-biphenyl-4-ylmethyl-2-oxo-pyrrolidine-1-carboxylic acid tert-butyl ester (4a, R1=t-butoxycarbonyl, R4=methyl

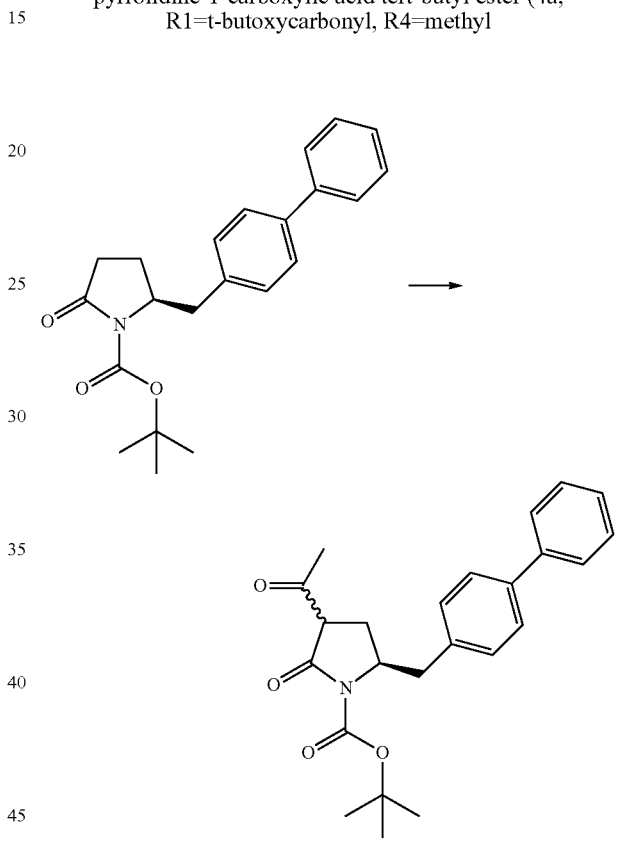

Under $N_2$, LHMDS (12.5 mL, 1.0 M in tetrahydrofuran, 12.5 mmol) is added to the mixture of (S)-2-biphenyl-4-ylmethyl-5-oxo-pyrrolidine-1-carboxylic acid tert-butyl ester (3a, R1=t-butoxycarbonyl) (1.76 g, 5 mmol) in 15 mL dry tetrahydrofuran is added to the reaction mixture at −10° C., the resulting mixture is then stirred for 30 min at −10° C. Acetyl chloride (0.47 g, 6 mmol) is added to the reaction mixture at −10° C., after about 1 hour at −10° C., the reaction mixture is diluted with 10 mL saturated aqueous ammonium chloride solution and stirred for 15 min, stop stirring, and remove the lower aqueous layer. the organic phase is then concentrated in vacuo. Ethyl acetate (20 mL) is added, filtered and the filtrate concentrated to give (R/S)-3-Acetyl-(S)-5-biphenyl-4-ylmethyl-2-oxo-pyrrolidine-1-carboxylic acid tert-butyl ester (3a, R1=t-butoxycarbonyl), the ratio of (3S, 5S) to (3R,5S) is 70:30 as determined by HPLC. $^1$HNMR (400 MHz, $CDCl_3$): 1.48 (s, 9H, $(CH_3)_3$), 2.17 (m, 1H, 3-CHH), 2.31 (s, 3H, $CH_3$), 2.42 (m, 1H, 3CHH), 2.67 (m, 1H, 5-CHH), 2.92 (m, 1H, 5-CHH), 3.09 (m, 1H, 2-CH), 4.38 (m, 1H, 4-CH), 7.10~7.80 (9H, m, aromatic).

HPLC Method

Column: Eclipse XDB-C18; 150×4.6 mm; 5 μm. Mobile Phase A (0.1% H3PO4) in water; Mobile Phase B (Acetonitrile). Gradient: 0 min (30% B); 8 min (95% B); 15 min (95% B). Flow rate: 1.0 ml min-1. Wavelength: 210 nm. Temperature: 30° C.

Retention time:
9.3 min (3S,5S-4, R1=t-butoxycarbonyl, R4=methyl)
9.5 min (3R,5S-4, R1=t-butoxycarbonyl, R4=methyl)
9.2 min (3a, R1=t-butoxycarbonyl)

EXAMPLE 12

R/S)-3-Isobutyryl-(S)-5-biphenyl-4-ylmethyl-2-oxo-pyrrolidine-1-carboxylic acid tert-butyl ester (4a, R1=t-butoxycarbonyl, R4=isopropyl

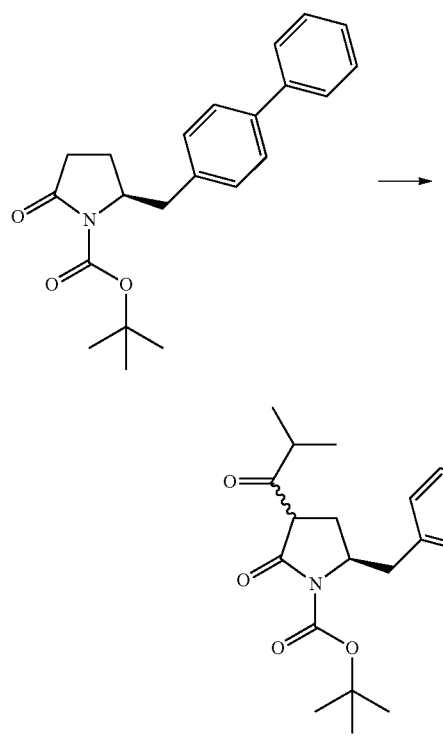

Under $N_2$, LHMDS (12.5 mL, 1.0 M in tetrahydrofuran, 12.5 mmol) is added to the mixture of (S)-2-Biphenyl-4-ylmethyl-5-oxo-pyrrolidine-1-carboxylic acid tert-butyl ester (3a, R1=t-butoxycarbonyl) (1.76 g, 5 mmol) in 15 mL dry tetrahydrofuran is added to the reaction mixture at −10° C., the resulting mixture is then stirred for 30 min at −10° C. Isobutyryl chloride (0.64 g, 6 mmol) is added to the reaction mixture at −10° C., after about 1 hour at −10° C., the reaction mixture is diluted with 10 mL saturated aqueous ammonium chloride solution and stirred for 15 min, stop stirring, and remove the lower aqueous layer. the organic phase is then concentrated in vacuo. ethyl acetate 20 mL is added, filtered and the filtrate concentrated to give (R/S)-3-Isobutyryl-(S)-5-biphenyl-4-ylmethyl-2-oxo-pyrrolidine-1-carboxylic acid tert-butyl ester (4a, R1=t-butoxycarbonyl, R4=isopropyl), the ration of (3S,5S) to (3R,5S) is 70:30 as determined by HPLC. 1HNMR (400 MHz, CDCl3): 1.03 (d, 3H, CH3), 1.05 (d, 3H, CH3), 1.43 (s, 9H, (CH3)3), 2.18 (m, 1H, 3-CHH), 2.43 (m, 1H, 3CHH), 2.70 (m, 1H, CH), 2.67 (m, 1H, 5-CHH), 2.92 (m, 1H, 5-CHH), 3.09 (m, 1H, 2-CH), 4.38 (m, 1H, 4-CH), 7.10~7.80 (9H, m, aromatic).

HPLC Method

Column: Eclipse XDB-C18; 150×4.6 mm; 5 μm. Mobile Phase A (0.1% $H_3PO_4$) in water; Mobile Phase B (Acetonitrile). Gradient: 0 min (30% B); 8 min (95% B); 15 min (95% B). Flow rate: 1.0 ml min$^{-1}$. Wavelength: 210 nm. Temperature: 30° C.

Retention time:
10.2 min (3S,5S-4, R1=t-butoxycarbonyl, R4=isopropyl)
10.5 min (3R,5S-4, R1=t-butoxycarbonyl, R4=isopropyl)
9.2 min (3a, R1=t-butoxycarbonyl)

EXAMPLE 13

R/S)-3-(2,2-dimethyl-propionyl)-(S)-5-biphenyl-4-ylmethyl-2-oxo-pyrrolidine-1-carboxylic acid tert-butyl ester (4a, R1=t-butoxycarbonyl, R4=t-butyl

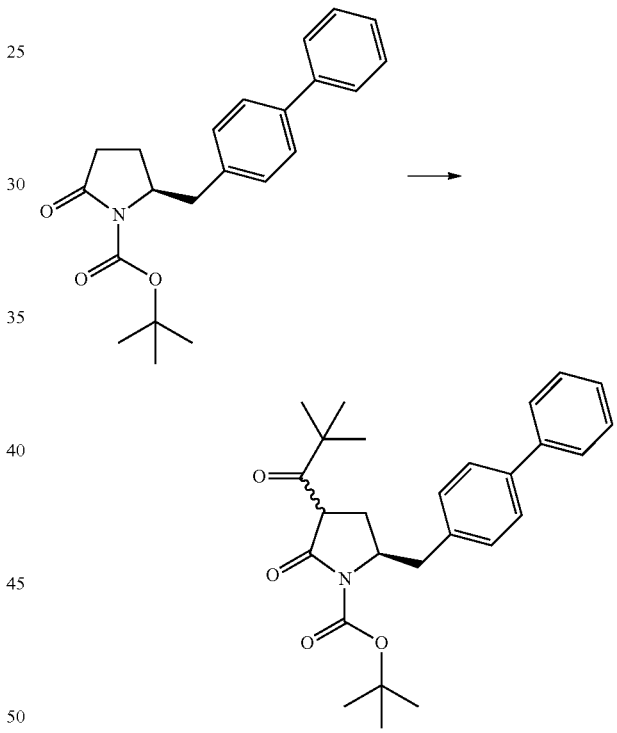

Under $N_2$, LHMDS (12.5 mL, 1.0 M in tetrahydrofuran, 12.5 mmol) is added to the mixture of (S)-2-Biphenyl-4-ylmethyl-5-oxo-pyrrolidine-1-carboxylic acid tert-butyl ester (3a, R1=t-butoxycarbonyl) (1.76 g, 5 mmol) in 15 mL dry tetrahydrofuran is added to the reaction mixture at −10° C., the resulting mixture is then stirred for 30 min at −10° C. 2,2-dimethyl-propionyl chloride (0.72 g, 6 mmol) is added to the reaction mixture at −10° C., after about 1 hour at −10° C., the reaction mixture is diluted with 10 mL saturated aqueous ammonium chloride solution and stirred for 15 min, stop stirring, and remove the lower aqueous layer. the organic phase is then concentrated in vacuo. Ethyl acetate 20 mL is added, filtered and the filtrate concentrated to give (R/S)-3-(2,2-dimethyl-propionyl)-(S)-5-biphenyl-4-ylmethyl-2-oxo-pyrrolidine-1-carboxylic acid tert-butyl ester (4a, R1=t-butoxycarbonyl, R4=isopropyl), the ration of (3S,5S) to (3R,5S) is 80:20 as determined by HPLC.

$^1$HNMR (400 MHz, CDCl$_3$): 0.98 (s, 9H, 3CH$_3$), 1.52 (s, 9H, (CH$_3$)$_3$), 2.19 (m, 1H, 3-CHH), 2.42 (m, 1H, 3CHH), 2.67 (m, 1H, 5-CHH), 2.92 (m, 1H, 5-CHH), 3.09 (m, 1H, 2-CH), 4.38 (m, 1H, 4-CH), 7.10~7.80 (9H, m, aromatic).

HPLC Method

Column: Eclipse XDB-C18; 150×4.6 mm; 5 μm. Mobile Phase A (0.1% H$_3$PO$_4$) in water; Mobile Phase B (Acetonitrile). Gradient: 0 min (30% B); 8 min (95% B); 15 min (95% B). Flow rate: 1.0 ml min$^{-1}$. Wavelength: 210 nm. Temperature: 30° C.

Retention time:
10.3 min (3S,5S-4, R1=t-butoxycarbonyl, R4=isopropyl)
10.5 min (3R,5S-4, R1=t-butoxycarbonyl, R4=isopropyl)
9.2 min (3a, R1=t-butoxycarbonyl)

EXAMPLE 14

S)-5-Biphenyl-4-ylmethyl-3-isobutyryl-1-((E)-styryl)-pyrrolidin-2-one (4a, R1=styryl, R4=isopropyl)

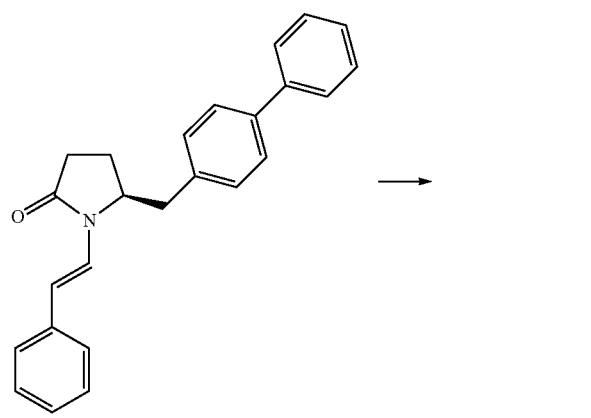

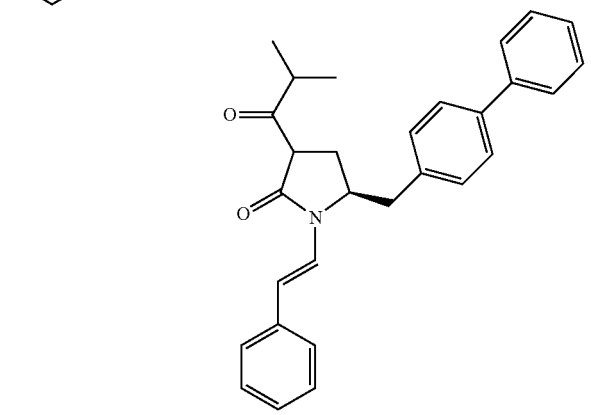

Method 1

(S)-5-Biphenyl-4-ylmethyl-1-((E)-styryl)-pyrrolidin-2-one (3a, R1=styryl) (5.0 g, 14.2 mmol) is heated to dissolve in 15 mL of anhydrous toluene, then add sodium hydride (0.8 g, 18.4 mmol) in portions, stir under nitrogen atmosphere for 30 min, then add methyl isobutyrate (1.7 g, 15.6 mmol, 98% purity) dropwise, the reaction mixture is refluxed under nitrogen overnight, cool to room temperature, quench with saturated NH$_4$Cl, extract with toluene, the combined extracts are washed with saturated Na$_2$CO$_3$ and brine, dry over anhydrous Na$_2$SO$_4$, evaporate the solvent under vacuum, the residue is purified by column chromatography to obtain (S)-5-Biphenyl-4-ylmethyl-3-isobutyryl-1-((E)-styryl)-pyrrolidin-2-one (4a, R1=styryl, R4=isopropyl). $^1$HNMR (400 MHz, CDCl$_3$): 1.02 (m, 6H, C(CH$_3$)$_2$), 2.05 (m, 1H, 3-CHH), 2.46 (m, 1H, 3-CHH), 2.97 (m, 1H, 5-CH$_2$H), 3.10 (m, 1H, CH(CH$_3$)$_2$)), 3.17 (m, 1H, 5-CH$_2$H), 3.22 (m, 1H, 2-CHH), 4.46 (m, 1H, 4-CH), 6.10 (d, 1H, C=CHH), 7.21~7.65 (15H, m, aromatic+C=CHH). The ratio of (3S,5S) to (3R,5S) is 70:30 as determined by HPLC.

Method 2

(S)-5-Biphenyl-4-ylmethyl-1-((E)-styryl)-pyrrolidin-2-one (3a, R1=styryl) (2.0 g, 5.7 mmol) is dissolved in 15 mL of anhydrous tetrahydrofuran, cool to −10~−15° C. by ice salt bath, add LiHMDS (14.2 mL, 14.2 mmol, 1 M in tetrahydrofuran) dropwise under nitrogen atmosphere, the result mixture is stirred at this temperature for 30 min, then add a solution of isobutyryl chloride (820 mg, 6.8 mmol) in 5 mL of anhydrous tetrahydrofuran dropwise, keep the temperature below −5° C., stir for 1 h, quench with saturated NH$_4$Cl aqueous solution, add 50 mL of ethyl acetate, separate the aqueous phase, wash with saturated Na$_2$CO$_3$ aqueous solution and brine, dry over anhydrous Na$_2$SO$_4$, evaporate the solvent under vacuum to obtain (S)-5-Biphenyl-4-ylmethyl-3-isobutyryl-1-((E)-styryl)-pyrrolidin-2-one (4a, R1=styryl, R4=isopropyl), which is direct used in next step. The ratio of (3S,5S) to (3R,5S) is 70:30 as determined by HPLC. Spectroscopic data as Example 14, Method 1.

HPLC Method (Methods 1 and 2)

Column: Eclipse XDB-C18; 150×4.6 mm; 5 μm. Mobile Phase A (0.1% H$_3$PO$_4$) in water; Mobile Phase B (Acetonitrile). Gradient: 0 min (30% B); 8 min (95% B); 15 min (95% B). Flow rate: 1.0 ml min$^{-1}$. Wavelength: 210 nm. Temperature: 30° C.

Retention time:
10.7 min (3S,5S-4, R1=styryl, R4=isopropyl)
11.1 min (3R,5S-4, R1=styryl, R4=isopropyl)
9.5 min (3a, R1=styryl)

EXAMPLE 15

S)-5-Biphenyl-4-ylmethyl-3-(2,2-dimethyl-propionyl)-1-((E)-styryl)-pyrrolidin-2-one (4a, R1=styryl, R4=t-butyl

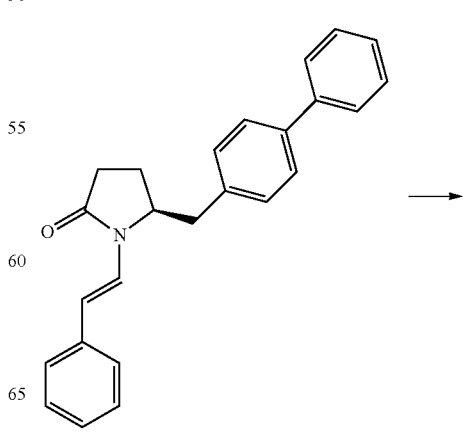

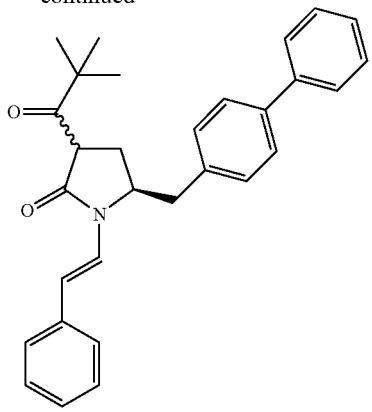

Method 1

(S)-5-biphenyl-4-ylmethyl-1-((E)-styryl)-pyrrolidin-2-one (3a, R1=styryl) (5.0 g, 14.2 mmol) is heated to dissolve in 15 mL of anhydrous toluene, then add sodium hydride (0.8 g, 18.4 mmol) in portions, stir under nitrogen atmosphere for 30 min, then add methyl trimethylacetate chloride (1.9 g, 15.6 mmol) dropwise, the reaction mixture is refluxed under nitrogen overnight, cool to r.t., quenched with saturated $NH_4Cl$, extracted with toluene, the combined extracts are washed with saturated $Na_2CO_3$ and brine, dry over anhydrous $Na_2SO_4$, evaporate the solvent under vacuum, the residue is purified by column chromatography to obtain (S)-5-Biphenyl-4-ylmethyl-3-(2,2-dimethyl-propionyl)-1-((E)-styryl)-pyrrolidin-2-one (4a, R1=styryl, R4=t-butyl). $^1$HNMR (400 MHz, $CDCl_3$): 1.02 (s, 9H, $C(CH_3)$), 2.05 (m, 1H, 3-CHH), 2.46 (m, 1H, 3-CHH), 2.97 (m, 1H, 5-$CH_2$H), 3.17 (m, 1H, 5-$CH_2$H), 3.22 (m, 1H, 2-CHH), 4.46 (m, 1H, 4-CH), 6.15 (d, 1H, C=CHH), 7.21~7.65 (15H, m, aromatic+C=CHH). The ratio of (3S,5S) to (3R,5S) is 82:18 as determined by HPLC.

Method 2

(S)-5-Biphenyl-4-ylmethyl-1-((E)styryl)-pyrrolidin-2-one (3a, R1=styryl) (2.0 g, 5.7 mmol) is dissolved in 15 mL of anhydrous tetrahydrofuran, cool to −10~−15° C. by ice salt bath, add LiHMDS (14.2 mL, 14.2 mmol, 1 M in tetrahydrofuran) dropwise under nitrogen atmosphere, the result mixture is stirred at this temperature for 30 min, then add isobutyryl chloride (820 mg, 6.8 mmol) as a solution in 5 mL of anhydrous tetrahydrofuran dropwise, keep the temperature below −5° C., stir for 1 h, quench with saturated $NH_4Cl$ aqueous solution, add 50 mL of ethyl acetate, separate the aqueous phase, wash with saturated $Na_2CO_3$ aqueous solution and brine, dry over anhydrous $Na_2SO_4$, evaporate the solvent under vacuum to obtain (S)-5-Biphenyl-4-ylmethyl-3-(2,2-dimethyl propionyl)-1-((E)-styryl)-pyrrolidin-2-one (4a, R1=styryl, R4=t-butyl), which is direct used in next step. The ratio of (3S,5S) to (3R,5S) is 80:20 as determined by HPLC. Spectroscopic data as Example 15, Method 1.

HPLC Method (Methods 1 and 2)

Column: Eclipse XDB-C18; 150×4.6 mm; 5 μm. Mobile Phase A (0.1% $H_3PO_4$) in water; Mobile Phase B (Acetonitrile). Gradient: 0 min (30% B); 8 min (95% B); 15 min (95% B). Flow rate: 1.0 ml min$^{-1}$. Wavelength: 210 nm. Temperature: 30° C.

Retention time:

10.7 min (3S,5S-4, R1=styryl, R4=t-butyl)
11.1 min (3R,5S-4, R1=styryl, R4=t-butyl)
9.5 min (3a, R1=styryl)

EXAMPLE 16

S)-5-Biphenyl-4-ylmethyl-2-oxo-pyrrolidine-1,3-dicarboxylic acid 1-tert-butyl ester (4a, R1=t-butoxycarbonyl, R4=hydroxyl

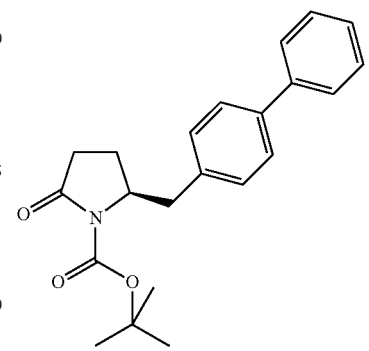

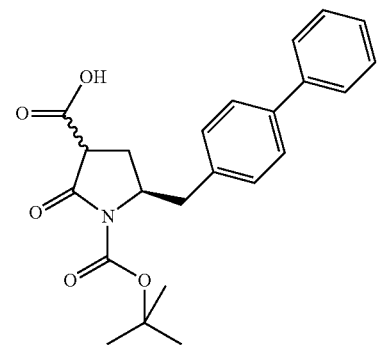

To a solution of diisopropyl amine (2.4 g, 24.0 mmol) in 20 mL of anhydrous tetrahydrofuran is added n-butyllithium (8.8 mL, 22.0 mmol, 2.5 M in hexane) dropwise under $N_2$ at −10~15° C., stir at this temperature for 1 h, add a solution of (S)-2-Biphenyl-4-ylmethyl-5-oxo-pyrrolidine-1-carboxylic acid tert-butyl ester (3a, R1=t-butoxycarbonyl) (7.0 g, 20.0 mmol) in 10 mL of anhydrous tetrahydrofuran dropwise, stir for 1 h, introduce $CO_2$ for 1 h, quench with saturated $NH_4Cl$ aqueous solution, extract with ethyl acetate, the combined organic phase is washed with brine, dry over anhydrous sodium sulfate, evaporate the solvent under vacuum, the residue is purified by column chromatography to obtain (S)-5-Biphenyl-4-ylmethyl-2-oxo-pyrrolidine-1,3-dicarboxylic acid 1-tert-butyl ester (4a, R1=t-butoxycarbonyl, R4=hydroxyl) 1HNMR (400 MHz, $CDCl_3$): 1.59 (s, 1H, Boc), 1.85 (m, 1H, 3CHH), 2.36 (m, 1H, 3CHH), 2.48 (m, 1H, 5-$CH_2$), 2.83 (m, 1H, 5-$CH_2$), 3.09 (m, 1H, 2-CH), 4.40 (m, 1H, 4-CH), 6.10 (d, 1H, C=CHH), 7.23~7.56 (9H, m, aromatic). The ratio of (3S,5S) to (3R,5S) is 36:64 as determined by HPLC.

HPLC Method

Column: Eclipse XDB-C18; 150×4.6 mm; 5 μm. Mobile Phase A (0.1% $H_3PO_4$) in water; Mobile Phase B (Acetonitrile). Gradient: 0 min (30% B); 8 min (95% B); 15 min (95% B). Flow rate: 1.0 ml min$^{-1}$. Wavelength: 210 nm. Temperature: 30° C.

Retention time:

8.0 min (3S,5S-4, R1=t-butoxycarbonyl, R4=hydroxyl)
8.1 min (3R,5S-4, R1=t-butoxycarbonyl, R4=hydroxyl).
9.2 min (3a, R1=t-butoxycarbonyl)

EXAMPLE 17

5R)-Biphenyl-4-ylmethyl-1-(4-methoxy-benzyl)-3-methylene-pyrrolidin-2-one (1a, R1=p-methoxybenzyl

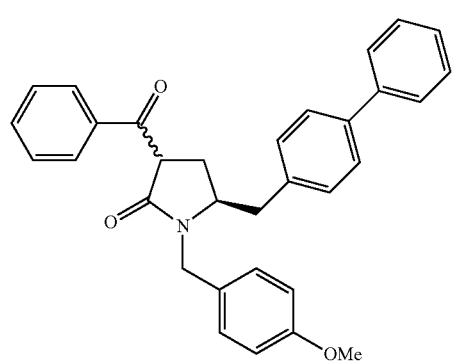

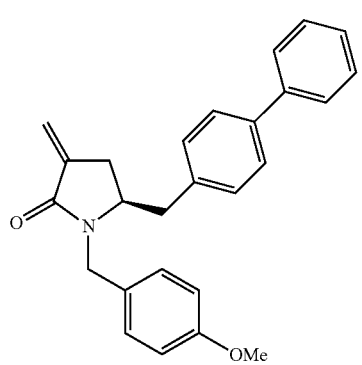

(3R/S)-benzoyl-(5S)-biphenyl-4-ylmethyl-1-(4-methoxybenzyl)pyrrolidin-2-one (4a, R1=p-methoxybenzyl, R4=phenyl) as a mixture of cis and trans diastereomers (700 mg, 1.47 mmol) is dissolved in tetrahydrofuran (5 mL), then sodium hydride (60 mg, 1.47 mmol, 55% in mineral oil) is added at 0° C. After stirring for 15 min, paraformadehyde (66 mg, 2.2 mmol) is added, the reaction mixture is refluxed for 30 min and allowed to cool to room temperature. After addition of NH$_4$Cl (sat. aq), the organic layer is separated, washed with brine, dried and concentrated to give (5R)-Biphenyl-4-ylmethyl-1-(4-methoxy-benzyl)-3-methylene-pyrrolidin-2-one (1a, R1=p-methoxybenzyl). $^1$H NMR (400 MHz, CDCl$_3$): 2.46-2.52 (m, 2H), 2.61-2.67 (m, 1H), 3.13-3.16 (m, 1H), 3.67-3.71 (m, 1H), 3.81 (s, 3H), 4.09 (d, J=14.8 Hz, 1H), 5.15 (d, J=14.8 Hz, 1H), 5.30 (1H, m), 6.02 (1H, m), 7.20~7.58 (13H, m, aromatic). MS (ESI, m/e) 384 (MH$^+$).

HPLC Method

Column: Eclipse XDB-C18; 150×4.6 mm; 5 μm. Mobile Phase A (0.1% H$_3$PO$_4$) in water; Mobile Phase B (Acetonitrile). Gradient: 0 min (30% B); 8 min (95% B); 15 min (95% B). Flow rate: 1.0 ml min$^{-1}$. Wavelength: 210 nm. Temperature: 30° C.

Retention time:

9.3 min (1a, R1=p-methoxybenzyl)

EXAMPLE 18

R)-5-Biphenyl-4-ylmethyl-3-methylene-2-oxo-pyrrolidine-1-carboxylic acid tert-butylester (1a, R1=t-butoxycarbonyl

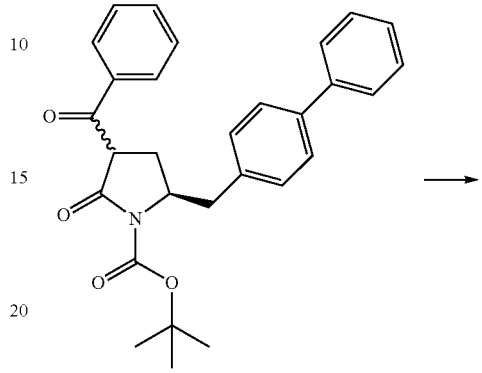

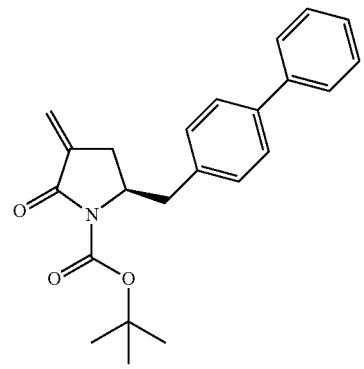

Method 1

Under N$_2$, (R/S)-3-Benzoyl-(S)-5-biphenyl-4-ylmethyl-2-oxo-pyrrolidine-1-carboxylic acid tert-butyl ester (4a, R1=t-butoxycarbonyl, R4=phenyl) (1.82 g, 4 mmol) in 5 mL toluene is added to the mixture of sodium hydride (55% in mineral oil, 0.23 g, 5.2 mmol) in 15 mL toluene at 0° C., and then heated to reflux, Paraformaldehyde (0.25 g, 8 mmol) is added in portions, and reflux for 2 hours. Then the reaction mixture is diluted with 10 mL saturated aqueous ammonium chloride solution and stirred for 15 min, stop stirring, and remove the lower aqueous layer. the organic phase is then concentrated in vacuo. ethyl acetate 20 mL is added, filtered and the filtrate concentrated and purified by column chromatography eluting with 5:1 heptane/ethyl acetate to afford (R)-5-Biphenyl-4-ylmethyl-3-methylene-2-oxo-pyrrolidine-1-carboxylic acid tert-butylester (1a, R1=t-butoxycarbonyl). Spectroscopic data as reported in WO2009/090251 (Example 23, Method 1).

Method 2

The mixture of (R/S)-3-Benzoyl-(S)-5-biphenyl-4-ylmethyl-2-oxo-pyrrolidine-1-carboxylic acid tert-butyl ester (4a, R1=t-butoxycarbonyl, R4=phenyl) (0.455 g, 1 mmol), paraformaldehyde (60 mg, 2 mmol), lithium chloride (85 mg, 2 mmol) and diisopropylethylamine (0.168 g, 1.3 mmol) in 5 mL dry tetrahydrofuran was heated to reflux for 2 hours. Then the reaction mixture is diluted with 5 mL saturated aqueous ammonium chloride solution and stirred for 15 min, stop stirring, and remove the lower aqueous layer. the organic phase is then concentrated in vacuo. ethyl acetate 10 mL is added, filtered and the filtrate concentrated and purified by column chromatography eluting with 5:1 heptane/ethyl acetate to afford (R)-5-Biphenyl-4-ylmethyl-3-methylene-2-oxo-pyrrolidine-1-carboxylic acid tert-butylester (1a, R1=t-butoxycarbonyl). Spectroscopic data as reported in WO2009/090251 (Example 23, Method 1).

Method 3

The mixture of (R/S)-3-Benzoyl-(S)-5-biphenyl-4-ylmethyl-2-oxo-pyrrolidine-1-carboxylic acid tert-butyl ester (4a, R1=t-butoxycarbonyl, R4=phenyl) (0.455 g, 1 mmol), paraformaldehyde (60 mg, 2 mmol) and KO'Bu (0.148 g, 1.3 mmol) in 5 mL dry tetrahydrofuran was heated to reflux for 2 hours. Then the reaction mixture is diluted with 5 mL saturated aqueous ammonium chloride solution and stirred for 15 min, stop stirring, and remove the lower aqueous layer. the organic phase is then concentrated in vacuo. ethyl acetate 10 mL is added, filtered and the filtrate concentrated and purified by column chromatography eluting with 5:1 heptane/ethyl acetate to afford (R)-5-Biphenyl-4-ylmethyl-3-methylene-2-oxo-pyrrolidine-1-carboxylic acid tert-butylester (1a, R1=t-butoxycarbonyl). Spectroscopic data as reported in WO2009/090251 (Example 23, Method 1).

Method 4

The mixture of (R/S)-3-Benzoyl-(S)-5-biphenyl-4-ylmethyl-2-oxo-pyrrolidine-1-carboxylic acid tert-butyl ester (4a, R1=t-butoxycarbonyl, R4=phenyl) (0.455 g, 1 mmol), paraformaldehyde (60 mg, 2 mmol), LiCl (85 mg, 2 mmol) and DBU (0.2 g, 1.3 mmol) in 5 mL dry tetrahydrofuran was heated to reflux for 2 hours. Then the reaction mixture is diluted with 5 mL saturated aqueous ammonium chloride solution and stirred for 15 min, stop stirring, and remove the lower aqueous layer. the organic phase is then concentrated in vacuo. ethyl acetate 10 mL is added, filtered and the filtrate concentrated and purified by column chromatography eluting with 5:1 heptane/ethyl acetate to afford (R)-5-Biphenyl-4-ylmethyl-3-methylene-2-oxo-pyrrolidine-1-carboxylic acid tert-butylester (1a, R1=t-butoxycarbonyl). Spectroscopic data as reported in WO2009/090251 (Example 23, Method 1).

Method 5

The mixture of (R/S)-3-Benzoyl-(S)-5-biphenyl-4-ylmethyl-2-oxo-pyrrolidine-1-carboxylic acid tert-butyl ester (4a, R1=t-butoxycarbonyl, R4=phenyl) (0.455 g, 1 mmol), formaldehyde (37% in water, 0.24 g, 3 mmol), tetrabutyl ammonium hydroxide (6.5 mg, 0.01 mmol) and K₂CO₃ (0.28 g, 1.3 mmol, dissolved in 1 mL water) in 5 mL dry tetrahydrofuran was heated to 50° C. and stirred for 2 hours. Then the reaction mixture is diluted with 5 mL brine and stirred for 15 min, stop stirring, and remove the lower aqueous layer. the organic phase is then concentrated in vacuo. ethyl acetate 10 mL is added, filtered and the filtrate concentrated and purified by column chromatography eluting with 5:1 heptane/ethyl acetate to afford (R)-5-Biphenyl-4-ylmethyl-3-methylene-2-oxo-pyrrolidine-1-carboxylic acid tert-butylester (1a, R1=t-butoxycarbonyl). Spectroscopic data as reported in WO2009/090251 (Example 23, Method 1).

Method 6

The mixture of (R/S)-3-Benzoyl-(S)-5-biphenyl-4-ylmethyl-2-oxo-pyrrolidine-1-carboxylic acid tert-butyl ester (4a, R1=t-butoxycarbonyl, R4=phenyl) (0.455 g, 1 mmol), paraformaldehyde (60 mg, 2 mmol) and potassium-tert-butoxide (0.148 g, 1.3 mmol) in 5 mL dry DME is stirred for 2 hours at 20° C. Then the reaction mixture is diluted with 5 mL saturated aqueous ammonium chloride solution and stirred for 15 min, stop stirring, and remove the lower aqueous layer. the organic phase is then concentrated in vacuo. ethyl acetate 10 mL is added, filtered and the filtrate concentrated and purified by column chromatography eluting with 5:1 heptane/ethyl acetate to afford (R)-5-Biphenyl-4-ylmethyl-3-methylene-2-oxo-pyrrolidine-1-carboxylic acid tert-butylester (1a, R1=t-butoxycarbonyl). Spectroscopic data as reported in WO2009/090251 (Example 23, Method 1).

EXAMPLE 19

R)-5-Biphenyl-4-ylmethyl-3-methylene-2-oxo-pyrrolidine-1-carboxylic acid tert-butylester (1a, R1=t-butoxycarbonyl

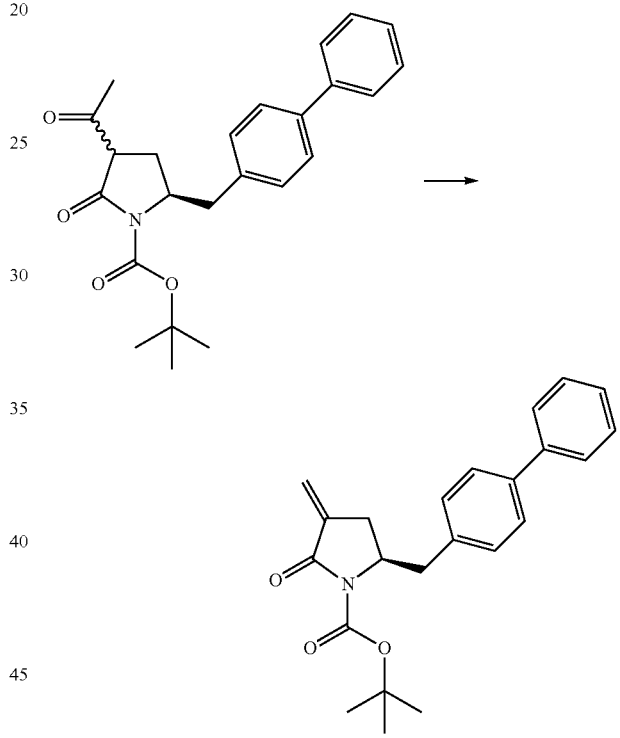

The mixture of (R/S)-3-Acetyl-(S)-5-biphenyl-4-ylmethyl-2-oxo-pyrrolidine-1-carboxylic acid tert-butyl ester (4a, R1=t-butoxycarbonyl, R4=methyl) (0.79 g, 2 mmol), formaldehyde (37% in water, 0.49 g, 6 mmol), tetrabutyl ammonium hydroxide (26 mg, 0.1 mmol) and K₂CO₃ (0.55 g, 1.3 mmol, dissolved in 2 mL water) in 10 mL dry tetrahydrofuran was heated to 50° C. and stirred for 2 hours. Then the reaction mixture is diluted with 10 mL brine and stirred for 15 min, stop stirring, and remove the lower aqueous layer. the organic phase is then concentrated in vacuo. ethyl acetate 20 mL is added, filtered and the filtrate concentrated and purified by column chromatography eluting with 5:1 heptane/ethyl acetate to afford (R)-5-Biphenyl-4-ylmethyl-3-methylene-2-oxo-pyrrolidine-1-carboxylic acid tert-butylester (1a, R1=t-butoxycarbonyl). Spectroscopic data as reported in WO2009/090251 (Example 23, Method 1).

EXAMPLE 20

R)-5-Biphenyl-4-ylmethyl-3-methylene-2-oxo-pyrrolidine-1-carboxylic acid tert-butylester (1a, R1=t-butoxycarbonyl

EXAMPLE 21

R)-5-Biphenyl-4-ylmethyl-3-methylene-2-oxo-pyrrolidine-1-carboxylic acid tert-butylester (1a, R1=t-butoxycarbonyl

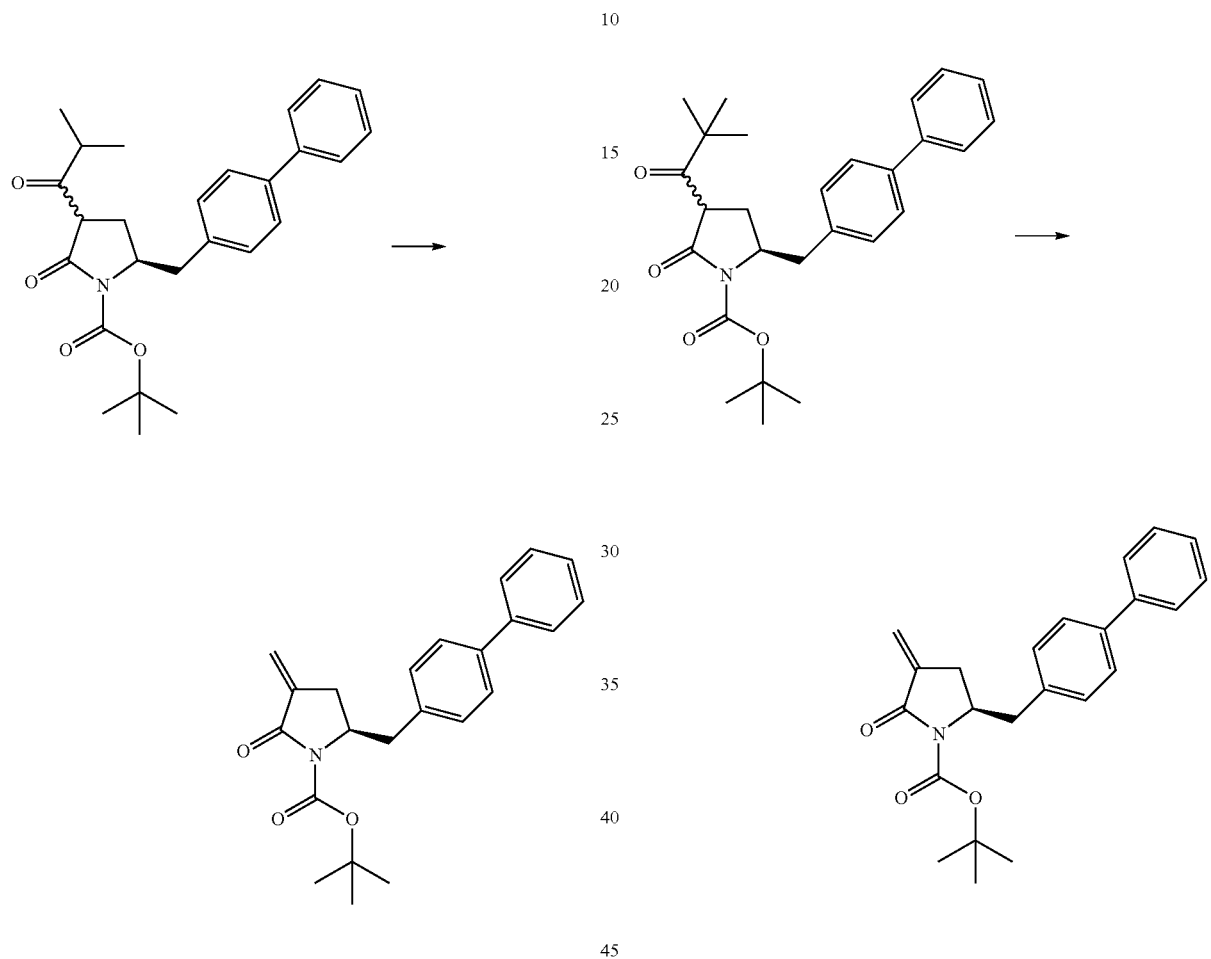

The mixture of (R/S)-3-Isobutyryl-(S)-5-biphenyl-4-ylmethyl-2-oxo-pyrrolidine-1-carboxylic acid tert-butyl ester (4a, R1=t-butoxycarbonyl, R4=isopropyl) (0.84 g, 2 mmol), formaldehyde (37% in water, 0.49 g, 6 mmol), tetrabutyl ammonium hydroxide (26 mg, 0.1 mmol) and K$_2$CO$_3$ (0.55 g, 1.3 mmol, dissolved in 2 mL water) in 10 mL dry tetrahydrofuran was heated to 50° C. and stirred for 2 hours. Then the reaction mixture is diluted with 10 mL brine and stirred for 15 min, stop stirring, and remove the lower aqueous layer. the organic phase is then concentrated in vacuo. ethyl acetate 20 mL is added, filtered and the filtrate concentrated and purified by column chromatography eluting with 5:1 heptane/ethyl acetate to afford (R)-5-Biphenyl-4-ylmethyl-3-methylene-2-oxo-pyrrolidine-1-carboxylic acid tert-butylester (1a, R1=t-butoxycarbonyl). Spectroscopic data as reported in WO2009/090251 (Example 23, Method 1).

The mixture of (R/S)-3-(2,2-dimethyl-propionyl)-(S)-5-biphenyl-4-ylmethyl-2-oxo-pyrrolidine-1-carboxylic acid tert-butyl ester 4a, R1=t-butoxycarbonyl, R4=t-butyl) (0.87 g, 2 mmol), formaldehyde (37% in water, 0.49 g, 6 mmol), tetrabutyl ammonium hydroxide (26 mg, 0.1 mmol) and K$_2$CO$_3$ (0.55 g, 1.3 mmol, dissolved in 2 mL water) in 10 mL dry tetrahydrofuran was heated to 50° C. and stirred for 2 hours. Then the reaction mixture is diluted with 10 mL brine and stirred for 15 min, stop stirring, and remove the lower aqueous layer. the organic phase is then concentrated in vacuo. ethyl acetate 20 mL is added, filtered and the filtrate concentrated and purified by column chromatography eluting with 5:1 heptane/ethyl acetate to afford (R)-5-Biphenyl-4-ylmethyl-3-methylene-2-oxo-pyrrolidine-1-carboxylic acid tert-butylester (1a, R1=t-butoxycarbonyl). Spectroscopic data as reported in WO2009/090251 (Example 23, Method 1).

EXAMPLE 22

R)-5-Biphenyl-4-ylmethyl-3-methylene-1-pyrrolidin-1-ylmethyl-pyrrolidin-2-one (1a, R1=pyrrolidinylmethyl)

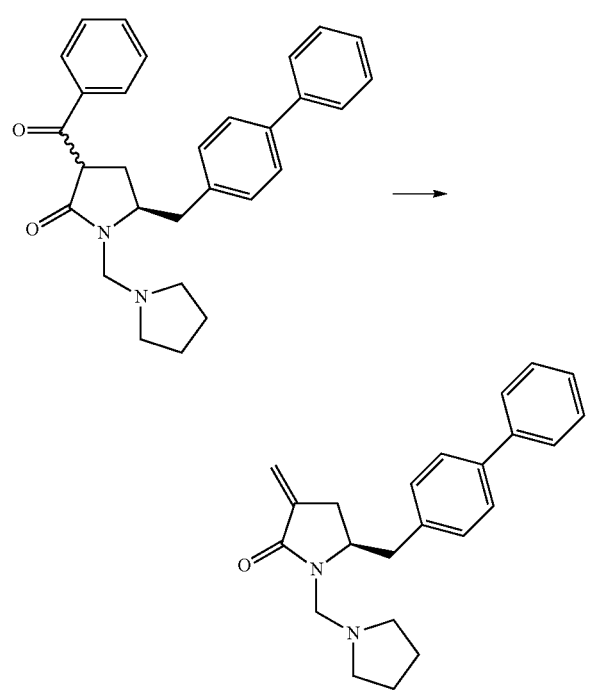

The mixture of (R/S)-3-Benzoyl-(S)-5-biphenyl-4-ylmethyl-1-pyrrolidin-1-ylmethyl-pyrrolidin-2-one (4a, R1=pyrrolidinylmethyl, R4=phenyl) (0.44 g, 1 mmol), formaldehyde (37% in water, 0.24 g, 3 mmol), TBAH (6.5 mg, 0.01 mmol) and K$_2$CO$_3$ (0.28 g, 1.3 mmol, dissolved in 1 mL water) in 5 mL dry tetrahydrofuran was heated to 50° C. and stirred for 2 hours. Then the reaction mixture is diluted with 5 mL brine and stirred for 15 min, stop stirring, and remove the lower aqueous layer. the organic phase is then concentrated in vacuo. ethyl acetate 10 mL is added, filtered and the filtrate concentrated and purified by column chromatography eluting with 5:1 heptane/ethyl acetate to afford (R)-5-Biphenyl-4-ylmethyl-3-methylene-1-pyrrolidin-1-ylmethyl-pyrrolidin-2-one (1a, R1=pyrrolidinylmethyl).

$^1$HNMR (400 MHz, CDCl$_3$): 1.68 (m, 4H, 2×CH$_2$CH$_2$), 2.06 (m, 1H, 3-CHH), 2.31 (m, 1H, 3-CHH), 2.51 (m, 4H, 2×NCH$_2$), 2.67 (d, 1H, 5-CHH), 2.65 (dd, 1H, N—CHH), 3.15 (dd, 1H, N—CHH), 2.92 (d, 1H, 5-CHH), 4.01 (m, 1H, 4-CH), 5.54 (d, 1H, =CHH), 6.02 (d, 1H, =CHH), 7.20-7.80 (14H, m, aromatic).

HPLC Method

Column: Eclipse XDB-C18; 150×4.6 mm; 5 μm. Mobile Phase A (0.1% H$_3$PO$_4$) in water; Mobile Phase B (Acetonitrile). Gradient: 0 min (90% B); 10 min (95% B); 15 min (95% B). Flow rate: 0.7 ml min$^{-1}$. Wavelength: 210 nm. Temperature: 30° C.

Retention time:

8.1 min (1a, R1=pyrrolidinylmethyl)

EXAMPLE 23

R)-5-Biphenyl-4-ylmethyl-3-methylene-1-((E)-styryl)-pyrrolidin-2-one (1a, R1=styryl Method 1

(S)-3-Benzoyl-5-biphenyl-4-ylmethyl-1-((E)-styryl)-pyrrolidin-2-one (4a, R1=styryl, R4=phenyl) (0.50 g, 1.1 mmol) is dissolved in 2 mL of anhydrous toluene, add sodium hydride (65 mg, 1.5 mmol) in portions then paraformaldehyde (66 mg, 2.2 mmol) in one portion, the result mixture is heat to reflux for 4 h under nitrogen atmosphere. The reaction mixture is cooled to room temperature, then quench with saturated NH$_4$Cl aqueous solution, extract with toluene, the organic extracts are washed with saturated Na$_2$CO$_3$ aqueous solution and brine, dry over anhydrous Na$_2$SO$_4$, evaporate the solvent under vacuum to obtain (R)-5-biphenyl-4-ylmethyl-3-methylene-1-((E)-styryl)-pyrrolidin-2-one (1a, R1=styryl) which could be used in next step directly. 1HNMR (400 MHz, CDCl$_3$): 2.68 (m, 2H, 3-CHH+5-CH$_2$H), 2.81 (m, 1H, 3-CHH), 3.28 (m, 1H, 5-CH$_2$H), 4.32 (m, 1H, 4-CH), 5.35 (s, 1H, C=CHH), 6.04 (s, 1H, C=CHH), 6.23 (d, 1H, C=CHH), 7.21~7.72 (m, 15H, aromatic+C=CHH).

Method 2

(S)-3-Benzoyl-5-biphenyl-4-ylmethyl-1-((E)-styryl)-pyrrolidin-2-one (4a, R1=styryl, R4=phenyl) (0.50 g, 1.1 mmol) is dissolved in 2 mL of anhydrous tetrahydrofuran, add potassium tert-butoxide (161 mg, 1.4 mmol) and paraformaldehyde (66 mg, 2.2 mmol) in one portion, the result mixture is heated to reflux for 2 h under nitrogen atmosphere. The reaction mixture is cooled to room temperature, add 15 mL of water, extract with toluene, the organic extracts are washed with saturated $Na_2CO_3$ aqueous solution and brine, dry over anhydrous $Na_2SO_4$, evaporate the solvent under vacuum to obtain the crude product which is purified by column chromatography to obtain (R)-5-Biphenyl-4-ylmethyl-3-methylene-1-((E)-styryl)-pyrrolidin-2-one (1a, R1=styryl). Spectroscopic data as Example 23, Method 1.

Method 3

(S)-3-Benzoyl-5-biphenyl-4-ylmethyl-1-((E)-styryl)-pyrrolidin-2-one (4a, R1=styryl, R4=phenyl) (0.50 g, 1.1 mmol) is dissolved in 2 mL of anhydrous tetrahydrofuran, add potassium tert-butoxide (161 mg, 1.4 mmol) and paraformaldehyde (66 mg, 2.2 mmol) in one portion, the result mixture is stirred at room temperature overnight under nitrogen atmosphere. The reaction mixture is added 15 mL of water, extract with toluene, the organic extracts are washed with saturated $Na_2CO_3$ aqueous solution and brine, dry over anhydrous $Na_2SO_4$, evaporate the solvent under vacuum, the residue is purified by column chromatography to get (R)-5-Biphenyl-4-ylmethyl-3-methylene-1-((E)-styryl)-pyrrolidin-2-one (1a, R1=styryl). Spectroscopic data as Example 23, Method 1.

Method 4

(S)-3-Benzoyl-5-biphenyl-4-ylmethyl-1-((E)-styryl)-pyrrolidin-2-one (4a, R1=styryl, R4=phenyl) (0.50 g, 1.1 mmol) is dissolved in 2 mL of methanol, add morpholine (125 mg, 1.4 mmol) and paraformaldehyde (66 mg, 2.2 mmol) in one portion, reflux for 2 h under nitrogen atmosphere. The reaction mixture is added 10 mL of 5% $HCl_{(aq)}$, extract with toluene, the organic extracts are washed with saturated $Na_2CO_3$ aqueous solution and brine, dry over anhydrous $Na_2SO_4$, evaporate the solvent under vacuum, the residue is purified by column chromatography to obtain (R)-5-Biphenyl-4-ylmethyl-3-methylene-1-((E)-styryl)-pyrrolidin-2-one (1a, R1=styryl). Spectroscopic data as Example 23, Method 1.

Method 5

(S)-3-Benzoyl-5-biphenyl-4-ylmethyl-1-((E)-styryl)-pyrrolidin-2-one (4a, R1=styryl, R4=phenyl) (54.3 g, 118.8 mmol) is dissolved in 120 mL of anhydrous tetrahydrofuran, add paraformaldehyde (4.28 g, 142.6 mmol), $iPr_2NEt$ (20.0 g, 154.5 mmol) and anhydrous Lithium chloride (2.56 g, 59.4 mmol), reflux for 2 h under nitrogen atmosphere. The reaction mixture is cooled to room temperature, add 200 mL of toluene, wash with 5% $HCl_{(aq)}$, saturated $Na_2CO_3$ and brine, dry over anhydrous $Na_2SO_4$, evaporate the solvent under vacuum to give (R)-5-Biphenyl-4-ylmethyl-3-methylene-1-((E)-styryl)-pyrrolidin-2-one (1a, R1=styryl). Spectroscopic data as Example 23, Method 1.

Method 6

(S)-3-Benzoyl-5-biphenyl-4-ylmethyl-1-((E)-styryl)-pyrrolidin-2-one (4a, R1=styryl, R4=phenyl) (1.0 g, 2.2 mmol) is dissolved in 5 mL of anhydrous tetrahydrofuran, add paraformaldehyde (80 mg, 2.6 mmol), triethyl amine (288 mg, 2.8 mmol) and anhydrous Lithium chloride (186 mg, 4.4 mmol), reflux overnight under nitrogen atmosphere. The reaction mixture is cooled to room temperature, add 20 mL of toluene, wash with 5% $HCl_{(aq)}$, saturated $Na_2CO_3$ and brine, dry over anhydrous $Na_2SO_4$, evaporate the solvent under vacuum to give (R)-5-Biphenyl-4-ylmethyl-3-methylene-1-((E)-styryl)-pyrrolidin-2-one (1a, R1=styryl). Spectroscopic data as Example 23, Method 1.

Method 7

(S)-3-Benzoyl-5-biphenyl-4-ylmethyl-1-((E)-styryl)-pyrrolidin-2-one (4a, R1=styryl, R4=phenyl) (1.0 g, 2.2 mmol) is dissolved in 5 mL of anhydrous tetrahydrofuran, add paraformaldehyde (80 mg, 2.6 mmol), DBU (434 mg, 2.8 mmol) and anhydrous Lithium chloride (186 mg, 4.4 mmol), reflux overnight under nitrogen atmosphere. The reaction mixture is cooled to room temperature, add 20 mL of toluene, wash with 5% $HCl_{(aq)}$, saturated $Na_2CO_3$ and brine, dry over anhydrous $Na_2SO_4$, evaporate the solvent under vacuum to give (R)-5-Biphenyl-4-ylmethyl-3-methylene-1-((E)-styryl)-pyrrolidin-2-one (1a, R1=styryl). Spectroscopic data as Example 23, Method 1.

Method 8

(S)-3-Benzoyl-5-biphenyl-4-ylmethyl-1-((E)-styryl)-pyrrolidin-2-one (4a, R1=styryl, R4=phenyl) (1.0 g, 2.2 mmol) is dissolved in 5 mL of anhydrous tetrahydrofuran, add 37% formaldehyde aqueous solution (0.36 mL, 4.4 mmol), 1 M $K_2CO_3$ aqueous solution (4.4 mL, 4.4 mmol) and $n-Bu_4NOH$ (12 mg, 0.05 mmol), heat to 40° C. for 2 h. The reaction mixture is cooled to room temperature, extract with ethyl acetate, the extracts are washed with saturated $Na_2CO_3$ aqueous solution and brine, dry over anhydrous $Na_2SO_4$ and concentrate under vacuum, the residue is purified by column chromatography to obtain (R)-5-Biphenyl-4-ylmethyl-3-methylene-1-((E)-styryl)-pyrrolidin-2-one (1a, R1=styryl). Spectroscopic data as Example 23, Method 1.

Method 9

(S)-3-Benzoyl-5-biphenyl-4-ylmethyl-1-((E)-styryl)-pyrrolidin-2-one (4a, R1=styryl, R4=phenyl) (1.0 g, 2.2 mmol) is dissolved in 5 mL of anhydrous tetrahydrofuran, add $iPr_2NEt$ (370 mg, 2.8 mmol) anhydrous Lithium chloride (49 mg, 1.1 mmol) and anhydrous $Na_2SO_4$ (260 mg, 2.2 mmol), reflux for 30 min under nitrogen atmosphere, then add paraformaldehyde (80 mg, 2.7 mmol), reflux for 2 h under nitrogen atmosphere. The reaction mixture is cooled to room temperature, add 20 mL of toluene and 10 mL of 5% $HCl_{(aq)}$, separate the aqueous phase, wash with saturated sodium hydrogen carbonate aqueous solution and brine, dry over anhydrous sodium sulfate and concentrate under vacuum to obtain (R)-5-Biphenyl-4-ylmethyl-3-methylene-1-((E)-styryl)-pyrrolidin-2-one (1a, R1=styryl). Spectroscopic data as Example 23, Method 1.

Method 10

(S)-3-Benzoyl-5-biphenyl-4-ylmethyl-1-((E)-styryl)-pyrrolidin-2-one (4a, R1=styryl, R4=phenyl) (1.0 g, 2.2 mmol) is dissolved in 5 mL of anhydrous tetrahydrofuran, add $iPr_2NEt$ (370 mg, 2.8 mmol) anhydrous Lithium chloride (49 mg, 1.1 mmol) and anhydrous $MgSO_4$ (260 mg, 2.2 mmol), reflux for 30 min under nitrogen atmosphere, then add paraformaldehyde (80 mg, 2.7 mmol), reflux for 2 h under nitrogen atmosphere. The reaction mixture is cooled to room temperature, add 20 mL of toluene and 10 mL of 5% $HCl_{(aq)}$, separate the aqueous phase, wash with saturated sodium hydrogen carbonate aqueous solution and brine, dry over anhydrous sodium sulfate and concentrate under vacuum to obtain (R)-5-Biphenyl-4-ylmethyl-3-methylene-1-((E)-styryl)-pyrrolidin-2-one (1a, R1=styryl).

Method 11

(S)-3-Benzoyl-5-biphenyl-4-ylmethyl-1-((E)-styryl)-pyrrolidin-2-one (4a, R1=styryl, R4=phenyl) (10.0 g, 21.9 mmol) is dissolved in 50 mL of anhydrous tetrahydrofuran, add $iPr_2NEt$ (3.7 g, 28.5 mmol) anhydrous Lithium chloride (490 mg, 11.0 mmol) and molecular sieves (2.0 g), refluxed for 30 min under nitrogen atmosphere, then add paraformaldehyde (790 mg, 26.3 mmol), reflux for 2 h under nitrogen atmosphere. The reaction mixture is cooled to room temperature, add 100 mL of toluene, filter to remove the molecular sieves, the filtration is washed with 5% $HCl_{(aq)}$(50 mL*2), saturated $Na_2CO_3$ and brine, dry over anhydrous $Na_2SO_4$ and concentrate under vacuum to obtain (R)-5-Biphenyl-4-ylmethyl-3-methylene-1-((E)-styryl)-pyrrolidin-2-one (1a, R1=styryl), which is direct used in next step. Spectroscopic data as Example 23, Method 1.

HPLC Method (Methods 1-11)

Column: Eclipse XDB-C18; 150×4.6 mm; 5 μm. Mobile Phase A (0.1% $H_3PO_4$) in water; Mobile Phase B (Acetonitrile). Gradient: 0 min (30% B); 8 min (95% B); 15 min (95% B). Flow rate: 1.0 ml min$^{-1}$. Wavelength: 210 nm. Temperature: 30° C.

Retention time:
10.2 min (1a, R1=styryl)

EXAMPLE 24

R)-5-Biphenyl-4-ylmethyl-1-((E)-but-1-enyl)-3-methylene-pyrrolidin-2-one (1a, R1=1-butenyl

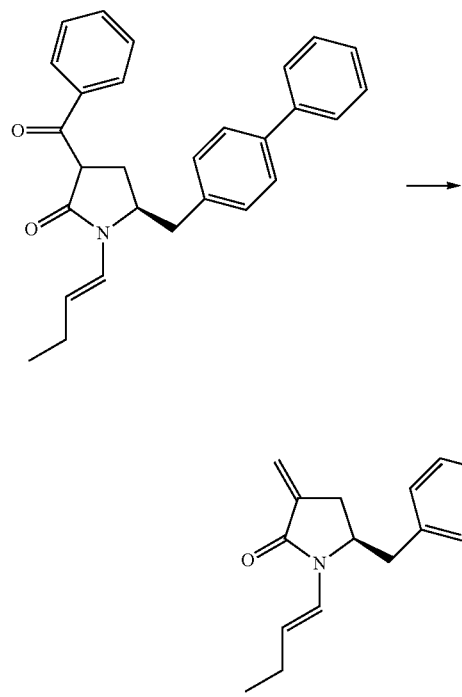

Method 1

To a suspension of sodium hydride (2.03 g, 46.3 mmol) in 40 mL of anhydrous toluene is cooled to 0° C. by ice bath, add a solution of (S)-3-Benzoyl-5-biphenyl-4-ylmethyl-1-((E)-but-1-enyl)-pyrrolidin-2-one (4a, R1=1-butenyl, R4=phenyl) (14.7 g, 35.7 mmol) in anhydrous toluene dropwise, stir for 30 min, then add paraformaldehyde (2.2 g, 71.4 mmol) in portions, heat to reflux under nitrogen atmosphere for 4 h, cool to room temperature, quench with saturated $NH_4Cl$ aqueous solution, extract with toluene, the combined organic extracts are washed with saturated $Na_2CO_3$ aqueous solution and brine, dry over anhydrous $Na_2SO_4$ and concentrate to obtain (R)-5-Biphenyl-4-ylmethyl-1-((E)-but-1-enyl)-3-methylene-pyrrolidin-2-one (1a, R1=1-butenyl). $^1$HNMR (400 MHz, $CDCl_3$): 1.07 (t, 3H, $CH_3H$), 2.12 (m, 2H, $CH_2H$), 2.57 (m, 2H, 3-$CH_2$), 2.65 (m, 1H, 5-$CH_2$), 3.16 (m, 1H, 5-$CH_2$), 4.14 (m, 1H, 4-CH), 5.22 (s, 1H, C=CHH), 5.27 (m, 1H, CH=CH), 5.91 (d, 1H, HC=CHH), 6.85 (d, 1H, HC=CH—N), 7.14~7.51 (9H, m, aromatic).

Method 2

To a solution of (S)-3-Benzoyl-5-biphenyl-4-ylmethyl-1-((E)-but-1-enyl)-pyrrolidin-2-one (4a, R1=1-butenyl, R4=phenyl) (5.5 g, 13.2 mmol) in 25 mL of tetrahydrofuran is added 1 M $K_2CO_3$ aqueous solution (26.4 mL, 26.4 mmol), 37% $CH_2O$ aqueous solution (2.2 mL, 26.4 mmol) and n-$Bu_4NOH$ (0.4 mL, 0.7 mmol), heat to 45° C. under $N_2$ for 2 h, cool to room temperature, extract with toluene, the combined organic layer are washed with 5% $HCl_{(aq)}$, saturated $Na_2CO_3$ aqueous solution and brine, dry over anhydrous $Na_2SO_4$, evaporate the solvent, the residue is purified by column chromatography to obtain (R)-5-Biphenyl-4-ylmethyl-1-((E)-but-1-enyl)-3-methylene-pyrrolidin-2-one (1a, R1=1-butenyl). Spectroscopic data as Example 24, Method 1.

HPLC Method (Methods 1 and 2)

Column: Eclipse XDB-C18; 150×4.6 mm; 5 μm. Mobile Phase A (0.1% $H_3PO_4$) in water; Mobile Phase B (Acetonitrile). Gradient: 0 min (30% B); 8 min (95% B); 15 min (95% B). Flow rate: 1.0 ml min$^{-1}$. Wavelength: 210 nm. Temperature: 30° C.

Retention time:
9.9 min (1a, R1=1-butenyl).

EXAMPLE 25

R)-5-Biphenyl-4-ylmethyl-3-methylene-1-((E)-styryl)-pyrrolidin-2-one (1a, R1=styryl

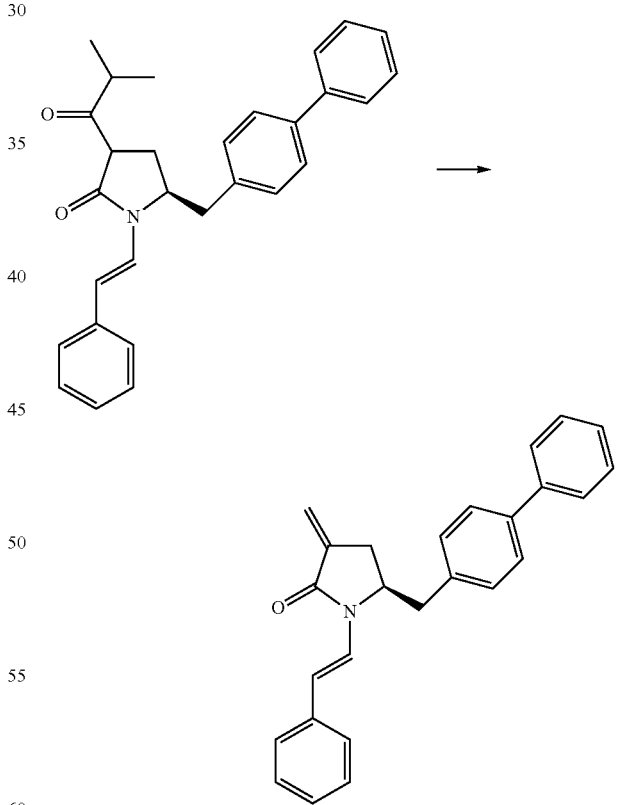

(S)-5-Biphenyl-4-ylmethyl-3-isobutyryl-1-((E)-styryl)-pyrrolidin-2-one (4a, R1=t-butoxycarbonyl, R4=isopropyl) (2.5 g, 6.2 mmol) is dissolved in 10 mL of anhydrous tetrahydrofuran, add iPr$_2$NEt (1.1 g, 8.2 mmol), anhydrous LiCl (140 mg, 3.2 mmol) and molecular sieves (0.5 g), the mixture is refluxed under nitrogen atmosphere for 30 min, then add paraformaldehyde (230 mg, 7.6 mmol) in one portion, reflux for 2 h, cool to room temperature, add 50 mL of toluene, filter, the filtration is washed with 10% HCl$_{(aq)}$, saturated Na$_2$CO$_3$ and brine, dry over anhydrous NaSO$_4$, evaporate under vacuum, the residue is purified by column chromatography to obtain (R)-5-Biphenyl-4-ylmethyl-3-methylene-1-((E)-styryl)-pyrrolidin-2-one (1a, R1=styryl). Stepectroscopic data as Example 23, Method 1.

EXAMPLE 26

R)-5-Biphenyl-4-ylmethyl-3-methylene-1-((E)-styryl)-pyrrolidin-2-one (1a, R1=styryl

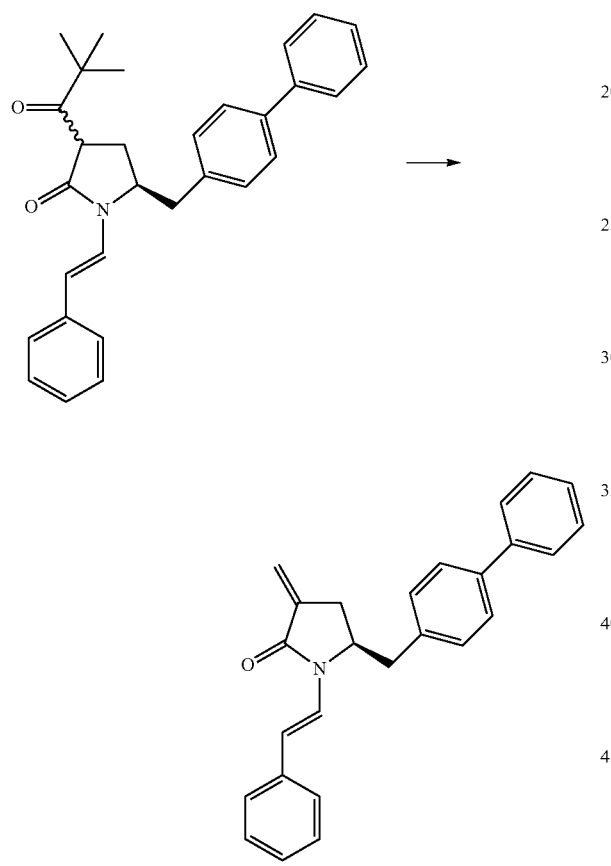

(S)-5-Biphenyl-4-ylmethyl-3-(2,2-dimethyl-propionyl)-1-((E)-styryl)-pyrrolidin-2-one (4a, R1=t-butoxycarbonyl, R4=t-butyl) (2.7 g, 6.2 mmol) is dissolved in 10 mL of anhydrous tetrahydrofuran, add iPr$_2$NEt (1.1 g, 8.2 mmol), anhydrous LiCl (140 mg, 3.2 mmol) and molecular sieves (0.5 g), the mixture is refluxed under nitrogen atmosphere for 30 min, then add paraformaldehyde (230 mg, 7.6 mmol) in one portion, reflux for 2 h, cool to room temperature, add 50 mL of toluene, filtere, the filtration is washed with 10% HCl$_{(aq)}$, saturated Na$_2$CO$_3$ and brine, dry over anhydrous NaSO$_4$, evaporate under vacuum, the residue is purified by column chromatography to obtain (R)-5-Biphenyl-4-ylmethyl-3-methylene-1-((E)-styryl)-pyrrolidin-2-one (1a, R1=styryl). Stepectroscopic data as Example 23, Method 1.

EXAMPLE 27

R)-5-Biphenyl-4-ylmethyl-3-methylene-2-oxo-pyrrolidine-1-carboxylic acid tert-butyl ester (1a, R1=t-butoxycarbonyl

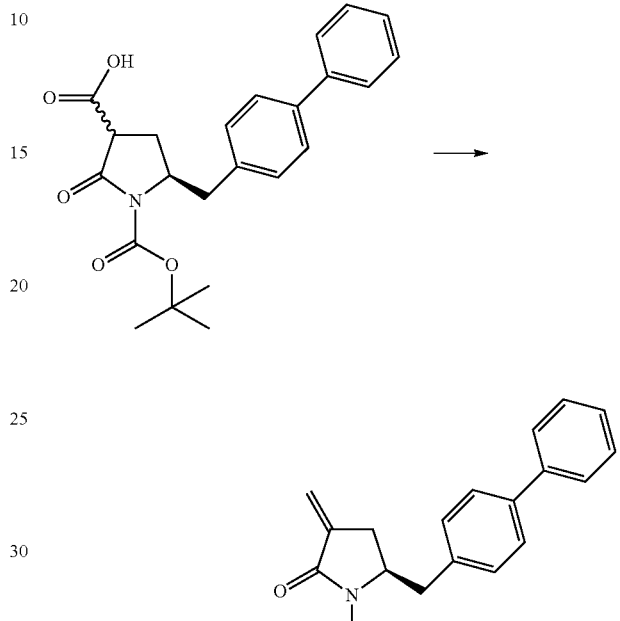

Biphenyl-4-ylmethyl-2-oxo-pyrrolidine-1,3-dicarboxylic acid 1-tert-butyl ester (4a, R1=t-butoxycarbonyl, R4=hydroxyl) (3.95 g, 10.0 mmol) is dissolved in 10 mL of methanol, add paraformaldehyde (0.60 g, 20.0 mmol) and morpholine (1.05 g, 12.0 mmol), the mixture is heated to refluxed for 2 h under nitrogen atmosphere, cool to room temperature, evaporate the solvent under vacuum, the residue is dissolved in 50 mL of ethyl acetate, ish with 1% HCl$_{(aq)}$, 10% sodium hydrogen carbonate$_{(aq)}$ and brine, dry over anhydrous sodium sulfate and concentrate under vacuum to obtain (R)-5-Biphenyl-4-ylmethyl-3-methylene-2-oxo-pyrrolidine-1-carboxylic acid tert-butyl ester (1a, R1=t-butoxycarbonyl).

$^1$HNMR (400 MHz, CDCl$_3$): 1.62 (s, 9H, (CH$_3$)$_3$), 2.56 (m, 1H, 3-CHH), 2.60 (m, 1H, 3CHH), 2.70 (d, 1H, 5-CHH), 3.26 (d, 1H, 5-CHH), 4.43 (m, 1H, 4-CH), 5.45 (d, 1H, C=CHH), 6.17 (d, 1H, C=CHH), 7.20~7.60 (9H, m, aromatic); m/z (+ESI) 381 ([MNa]$^+$, 7%), 364 ([MH]$^+$, 12), 308(100), 264 (10).

HPLC Method

Column: Eclipse XDB-C18; 150×4.6 mm; 5 μm. Mobile Phase A (0.1% H$_3$PO$_4$) in water; Mobile Phase B (Acetonitrile). Gradient: 0 min (30% B); 8 min (95% B); 15 min (95% B). Flow rate: 1.0 ml min$^{-1}$. Wavelength: 210 nm. Temperature: 30° C.

Retention time: 9.7 min (1a, R1=t-butoxycarbonyl)

EXAMPLE 28

R)-5-Biphenyl-4-ylmethyl-3-methylene-2-oxo-pyrrolidine-1-carboxylic acid tert-butylester (1a, R1=t-butoxycarbonyl

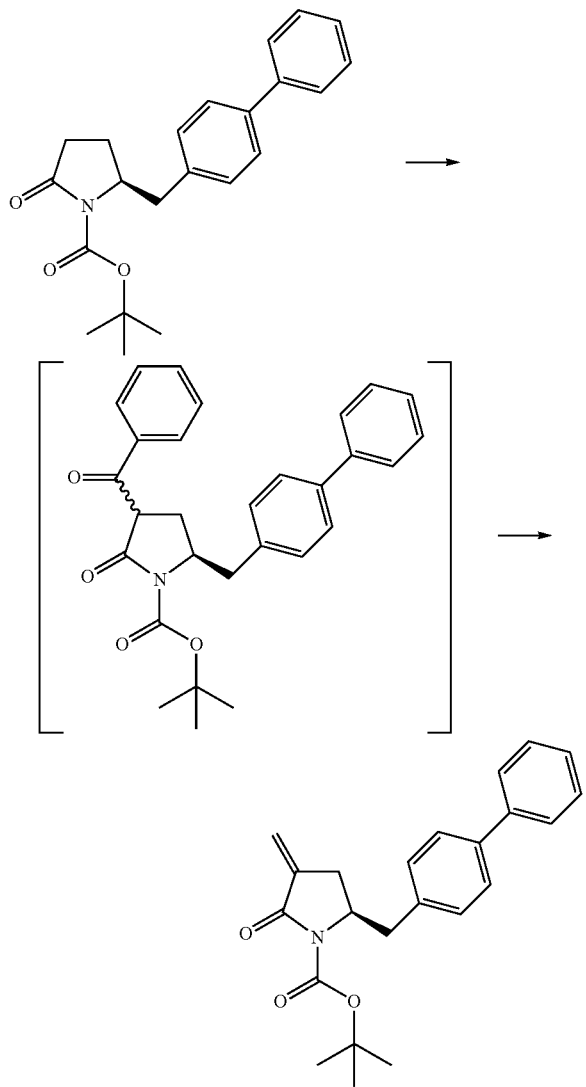

Method 1

Under $N_2$, n-butyllithium (56 mL, 2.5 M in hexane, 0.14 mol) is added to the mixture of HMDS (24.2 g, 0.15 mol) in 300 mL dry tetrahydrofuran at −10° C., the resulting mixture is then stirred for 30 min at −10° C. A mixture of (S)-2-biphenyl-4-ylmethyl-5-oxo-pyrrolidine-1-carboxylic acid tert-butyl ester (3a, R1=t-butoxycarbonyl) (35.1 g, 0.1 mol) in 50 mL dry tetrahydrofuran is added to the reaction mixture at −10° C., after about 30 min, n-butyllithium (40 mL, 2.5 M in hexane, 0.1 mol) is added to the reaction mixture at −10° C., the resulting mixture is then stirred for 30 min at −10° C. benzoyl chloride (15.5 g, 0.11 mol) is added to the reaction mixture at −10° C., after about 1 hour at −10° C., the reaction mixture is diluted with 100 mL saturated aqueous ammonium chloride solution and stirred for 15 min, stop stirring, and remove the lower aqueous layer. Formaldehyde (37% in water, 24.3 g, 0.3 mol), $K_2CO_3$ aqueous solution (27.6 g in 100 mL water, 0.2 mol) and tetrabutyl-ammonium-hydroxide solution (40% in water, 1.3 g, 5 mmol) are added to the remaining organic phase, and heated to 50° C., and stirred for 2 hours. Then the reaction mixture is diluted with 100 mL brine and stirred for 15 min, stop stirring, and remove the lower aqueous layer. the organic phase is then concentrated in vacuo. ethyl acetate 200 mL is added, filtered and the filtrate concentrated to give (R)-5-Biphenyl-4-ylmethyl-3-methylene-2-oxo-pyrrolidine-1-carboxylic acid tert-butylester (1a, R1=t-butoxycarbonyl). Crude (R)-5-Biphenyl-4-ylmethyl-3-methylene-2-oxo-pyrrolidine-1-carboxylic acid tert-butylester (1a, R1=t-butoxycarbonyl) is purified by column chromatography eluting with 3:1 heptane/ethyl acetate. $^1$HNMR (400 MHz, $CDCl_3$): 1.62 (s, 9H, $(CH_3)_3$), 2.56 (m, 1H, 3-CHH), 2.60 (m, 1H, 3CHH), 2.70 (d, 1H, 5-CHH), 3.26 (d, 1H, 5-CHH), 4.43 (m, 1H, 4-CH), 5.45 (d, 1H, C=CHH), 6.17 (d, 1H, C=CHH), 7.20–7.60 (9H, m, aromatic).; m/z (+ESI) 381 ($[MNa]^+$, 7%), 364 ($[MH]^+$, 12), 308(100), 264 (10). the ratio of intermediate (3S,5S-4, R1=t-butoxycarbonyl, R4=phenyl) to (3R,5S-4, R1=t-butoxycarbonyl, R4=phenyl) is 70:30 as determined by HPLC.

Method 2

Under $N_2$, n-butyllithium (56 mL, 2.5 M in hexane, 0.14 mol) is added to the mixture of Diisopropylamine (14.2 g, 0.15 mol) in 300 mL dry tetrahydrofuran at −10° C., the resulting mixture is then stirred for 30 min at −10° C. a mixture of (S)-2-Biphenyl-4-ylmethyl-5-oxo-pyrrolidine-1-carboxylic acid tert-butyl ester (3a, R1=t-butoxycarbonyl) (35.1 g, 0.1 mol) in 50 mL dry tetrahydrofuran is added to the reaction mixture at −10° C., after about 30 min, n-butyllithium (40 mL, 2.5 M in hexane, 0.1 mol) is added to the reaction mixture at −10° C., the resulting mixture is then stirred for 30 min at −10° C. benzoyl chloride (15.5 g, 0.11 mol) is added to the reaction mixture at −10° C., after about 1 hour at −10° C., the reaction mixture is diluted with 100 mL saturated aqueous ammonium chloride solution and stirred for 15 min, stop stirring, and remove the lower aqueous layer. Formaldehyde (37% in water, 24.3 g, 0.3 mol), $K_2CO_3$ aqueous solution (27.6 g in 100 mL water, 0.2 mol) and tetrabutyl-ammonium-hydroxide solution (40% in water, 1.3 g, 5 mmol) are added to the remaining organic phase, and heated to 50° C., and stirred for 2 hours. Then the reaction mixture is diluted with 100 mL brine and stirred for 15 min, stop stirring, and remove the lower aqueous layer. the organic phase is then concentrated in vacuo. ethyl acetate 200 mL is added, filtered and the filtrate concentrated to give (R)-5-Biphenyl-4-ylmethyl-3-methylene-2-oxo-pyrrolidine-1-carboxylic acid tert-butylester (1a, R1=t-butoxycarbonyl). Crude (R)-5-Biphenyl-4-ylmethyl-3-methylene-2-oxo-pyrrolidine-1-carboxylic acid tert-butylester (1a, R1=t-butoxycarbonyl) can be purified by column chromatography eluting with 3:1 heptane/ethyl acetate. The ratio of intermediate (3S,5S-4, R1=t-butoxycarbonyl, R4=phenyl) to (3R,5S-4, R1=t-butoxycarbonyl, R4=phenyl) is 70:30 as determined by HPLC. Spectroscopic data as Example 28, Method 1.

Method 3

Under $N_2$, LHMDS (25 mL, 1.0 M in tetrahydrofuran, 25 mmol) is added to the mixture of (S)-2-Biphenyl-4-ylmethyl-5-oxo-pyrrolidine-1-carboxylic acid tert-butyl ester (3a, R1=t-butoxycarbonyl) (3.51 g, 10 mmol) in 20 mL dry tetrahydrofuran is added to the reaction mixture at −10° C., the resulting mixture is then stirred for 30 min at −10° C. benzoyl chloride (1.55 g, 11 mmol) is added to the reaction mixture at −10° C., after about 1 hour at −10° C., the reaction mixture is diluted with 15 mL saturated aqueous ammonium chloride solution and stirred for 15 min, stop stirring, and remove the lower aqueous layer. Formaldehyde (37% in water, 2.43 g, 0.03 mol), $K_2CO_3$ aqueous solution (2.76 g in 10 mL water, 0.02 mol) and tetrabutyl-ammonium-hydroxide solution (40% in water, 0.13 g, 0.5 mmol) are added to the remaining organic phase, and heated to 50° C., and stirred for 2 hours. Then the reaction mixture is diluted with 15 mL brine and stirred for 15 min, stop stirring, and remove the lower aqueous layer. the organic phase is then concentrated in vacuo. ethyl acetate 20 mL is added, filtered and the filtrate concentrated to give (R)-5-Biphenyl-4-ylmethyl-3-methylene-2-oxo-pyrrolidine-1-carboxylic acid tert-butylester (1a, R1=t-butoxycarbonyl). Crude (R)-5-Biphenyl-4-ylmethyl-3-methylene-2-oxo-pyrrolidine-1-carboxylic acid tert-butylester (1a, R1=t-butoxycarbonyl) can be purified by column chromatography eluting with 3:1 heptane/ethyl acetate. The ratio of intermediate (3S,5S-4-a, R1=t-butoxycarbonyl, R4=benzyl) to (3R,5S-4, R1=t-butoxycarbonyl, R4=phenyl) is 70:30 as determined by HPLC. Spectroscopic data as Example 28, Method 1.

Method 4

Under $N_2$, LDA (25 mL, 1.0 M in tetrahydrofuran, 25 mmol) is added to the mixture of (S)-2-Biphenyl-4-ylmethyl-5-oxo-pyrrolidine-1-carboxylic acid tert-butyl ester (3a, R1=t-butoxycarbonyl) (3.51 g, 10 mmol) in 20 mL dry tetrahydrofuran is added to the reaction mixture at −10° C., the resulting mixture is then stirred for 30 min at −10° C. benzoyl chloride (1.55 g, 11 mmol) is added to the reaction mixture at −10° C., after about 1 hour at −10° C., the reaction mixture is diluted with 15 mL saturated aqueous ammonium chloride solution and stirred for 15 min, stop stirring, and remove the lower aqueous layer. Formaldehyde (37% in water, 2.43 g, 0.03 mol), $K_2CO_3$ aqueous solution (2.76 g in 10 mL water, 0.02 mol) and tetrabutyl-ammonium-hydroxide solution (40% in water, 0.13 g, 0.5 mmol) are added to the remaining organic phase, and heated to 50° C., and stirred for 2 hours. Then the reaction mixture is diluted with 15 mL brine and stirred for 15 min, stop stirring, and remove the lower aqueous layer. the organic phase is then concentrated in vacuo. ethyl acetate 20 mL is added, filtered and the filtrate concentrated to give (R)-5-Biphenyl-4-ylmethyl-3-methylene-2-oxo-pyrrolidine-1-carboxylic acid tert-butylester (1a, R1=t-butoxycarbonyl). Crude (R)-5-Biphenyl-4-ylmethyl-3-methylene-2-oxo-pyrrolidine-1-carboxylic acid tert-butylester (1a, R1=t-butoxycarbonyl) can be purified by column chromatography eluting with 3:1 heptane/ethyl acetate. The ratio of intermediate (3S,5S-4, R1=t-butoxycarbonyl, R4=phenyl) to (3R,5S-4, R1=t-butoxycarbonyl, R4=phenyl) is 70:30 as determined by HPLC. Spectroscopic data as Example 28, Method 1.

HPLC Method (Methods 1-4)

Column: Eclipse XDB-C18; 150×4.6 mm; 5 µm. Mobile Phase A (0.1% $H_3PO_4$) in water; Mobile Phase B (Acetonitrile). Gradient: 0 min (30% B); 8 min (95% B); 15 min (95% B). Flow rate: 1.0 ml min$^{-1}$. Wavelength: 210 nm. Temperature: 30° C.

Retention time:

9.7 min (1a, R1=t-butoxycarbonyl)

EXAMPLE 29

R)-5-Biphenyl-4-ylmethyl-3-methylene-2-oxo-pyrrolidine-1-carboxylic acid tert-butylester (1a, R1=t-butoxycarbonyl

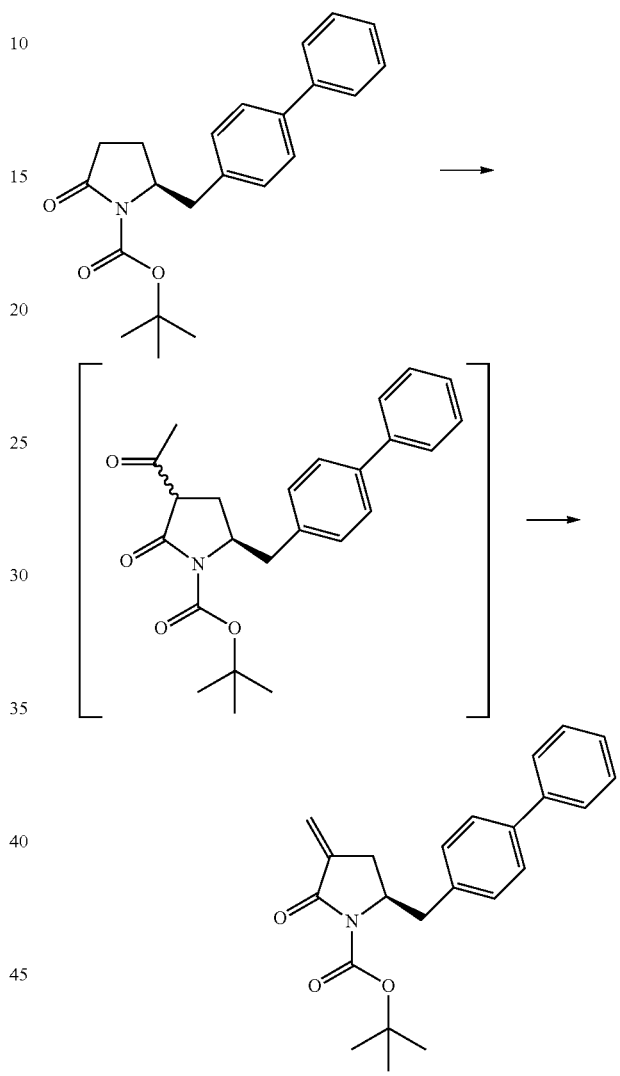

Under $N_2$, LHMDS (12.5 mL, 1.0 M in tetrahydrofuran, 12.5 mmol) is added to the mixture of (S)-2-Biphenyl-4-ylmethyl-5-oxo-pyrrolidine-1-carboxylic acid tert-butyl ester (3a, R1=t-butoxycarbonyl) (1.76 g, 5 mmol) in 15 mL dry tetrahydrofuran is added to the reaction mixture at −10° C., the resulting mixture is then stirred for 30 min at −10° C. acetyl chloride (0.47 g, 6 mmol) is added to the reaction mixture at −10° C., after about 1 hour at −10° C., the reaction mixture is diluted with 10 mL saturated aqueous ammonium chloride solution and stirred for 15 min, stop stirring, and remove the lower aqueous layer. Formaldehyde (37% in water, 1.2 g, 15 mmol), $K_2CO_3$ aqueous solution (1.4 g in 5 mL water, 0.01 mol) and tetrabutyl-ammonium-hydroxide solution (40% in water, 0.06 g, 0.25 mmol) are added to the remaining organic phase, and heated to 50° C., and stirred for 2 hours. Then the reaction mixture is diluted with 10 mL brine and stirred for 15 min, stop stirring, and remove the lower aqueous layer. the organic phase is then concentrated in vacuo. ethyl acetate 20 mL is added, filtered and the filtrate concentrated to give (R)-5-Biphenyl-4-ylmethyl-3-methylene-2-oxo-pyrrolidine-1-carboxylic acid tert-butylester (1a, R1=t-butoxycarbonyl). Crude (R)-5-biphenyl-4-ylmethyl-3-methylene-2-oxo-pyrrolidine-1-carboxylic acid tert-butylester (1a, R1=t-butoxycarbonyl) can be purified by column chromatography eluting with 3:1 heptane/ethyl acetate. The ratio of intermediate (3S,5S-4, R1=t-butoxycarbonyl, R4=methyl) to (3R,5S-4, R1=t-butoxycarbonyl, R4=methyl) is 70:30 as determined by HPLC. Spectroscopic data as Example 28, Method 1.

EXAMPLE 30

R)-5-Biphenyl-4-ylmethyl-3-methylene-2-oxo-pyrrolidine-1-carboxylic acid tert-butylester (1a, R1=t-butoxycarbonyl

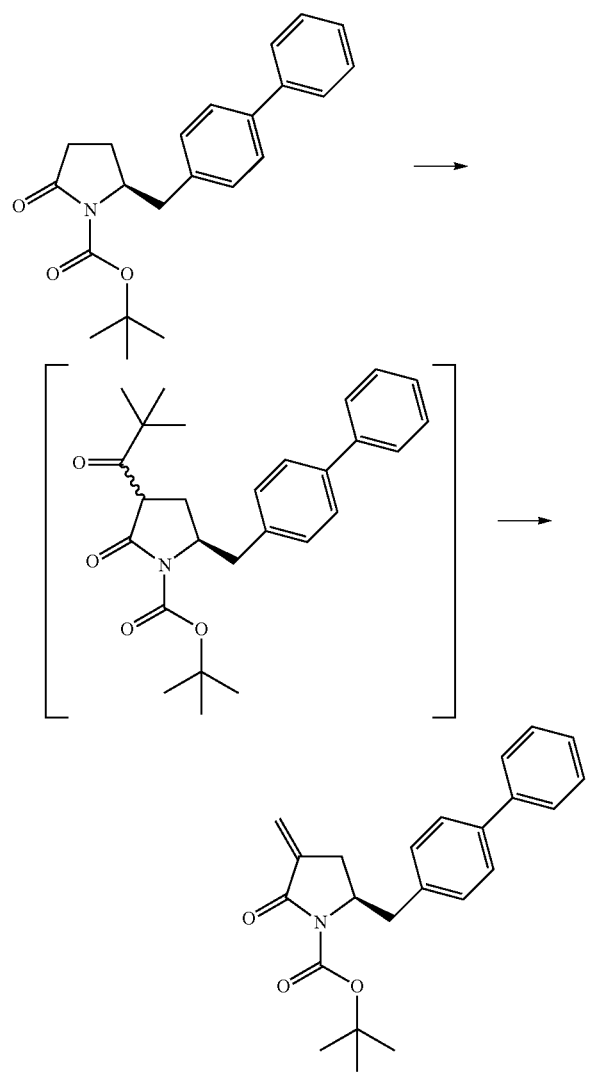

Under $N_2$, LHMDS (12.5 mL, 1.0 M in tetrahydrofuran, 12.5 mmol) is added to the mixture of (S)-2-Biphenyl-4-ylmethyl-5-oxo-pyrrolidine-1-carboxylic acid tert-butyl ester (3a, R1=t-butoxycarbonyl) (1.76 g, 5 mmol) in 15 mL dry tetrahydrofuran is added to the reaction mixture at −10° C., the resulting mixture is then stirred for 30 min at −10° C. 2,2-Dimethyl-propionyl chloride (0.72 g, 6 mmol) is added to the reaction mixture at −10° C., after about 1 hour at −10° C., the reaction mixture is diluted with 10 mL saturated aqueous ammonium chloride solution and stirred for 15 min, stop stirring, and remove the lower aqueous layer. Formaldehyde (37% in water, 1.2 g, 15 mmol), $K_2CO_3$ aqueous solution (1.4 g in 5 mL water, 0.01 mol) and tetrabutyl-ammonium-hydroxide solution (40% in water, 0.06 g, 0.25 mmol) are added to the remaining organic phase, and heated to 50° C., and stirred for 2 hours. Then the reaction mixture is diluted with 10 mL brine and stirred for 15 min, stop stirring, and remove the lower aqueous layer. the organic phase is then concentrated in vacuo. ethyl acetate 20 mL is added, filtered and the filtrate concentrated to give (R)-5-Biphenyl-4-ylmethyl-3-methylene-2-oxo-pyrrolidine-1-carboxylic acid tert-butylester (1a, R1=t-butoxycarbonyl). Crude (R)-5-Biphenyl-4-ylmethyl-3-methylene-2-oxo-pyrrolidine-1-carboxylic acid tert-butylester (1a, R1=t-butoxycarbonyl) can be purified by column chromatography eluting with 3:1 heptane/ethyl acetate. The ratio of intermediate (3S,5S-4, R1=t-butoxycarbonyl, R4=t-butyl) to (3R,5S-4, R1=t-butoxycarbonyl, R4=t-butyl) is 80:20 as determined by HPLC. Spectroscopic data as Example 28, Method 1.

EXAMPLE 31

R)-5-Biphenyl-4-ylmethyl-3-methylene-2-oxo-pyrrolidine-1-carboxylic acid tert-butylester (1a, R1=t-butoxycarbonyl

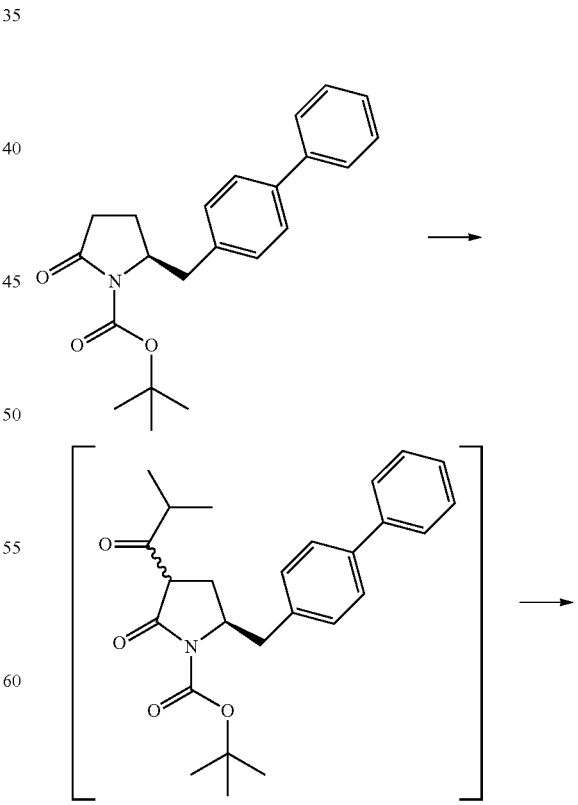

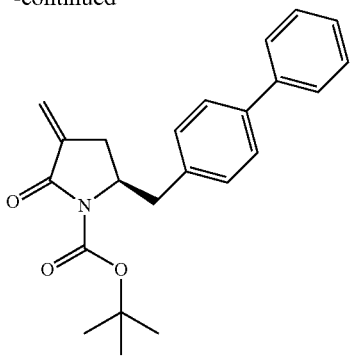

Under N₂, LHMDS (12.5 mL, 1.0 M in tetrahydrofuran, 12.5 mmol) is added to the mixture of (S)-2-Biphenyl-4-ylmethyl-5-oxo-pyrrolidine-1-carboxylic acid tert-butyl ester (3a, R1=t-butoxycarbonyl) (1.76 g, 5 mmol) in 15 mL dry tetrahydrofuran is added to the reaction mixture at −10° C., the resulting mixture is then stirred for 30 min at −10° C. Isobutyryl chloride (0.64 g, 6 mmol) is added to the reaction mixture at −10° C., after about 1 hour at −10° C., the reaction mixture is diluted with 10 mL saturated aqueous ammonium chloride solution and stirred for 15 min, stop stirring, and remove the lower aqueous layer. Formaldehyde (37% in water, 1.2 g, 15 mmol), K₂CO₃ aqueous solution (1.4 g in 5 mL water, 0.01 mol) and tetrabutyl-ammonium-hydroxide solution (40% in water, 0.06 g, 0.25 mmol) are added to the remaining organic phase, and heated to 50° C., and stirred for 2 hours. Then the reaction mixture is diluted with 10 mL brine and stirred for 15 min, stop stirring, and remove the lower aqueous layer. the organic phase is then concentrated in vacuo. ethyl acetate 20 mL is added, filtered and the filtrate concentrated to give (R)-5-Biphenyl-4-ylmethyl-3-methylene-2-oxo-pyrrolidine-1-carboxylic acid tert-butylester (1a, R1=t-butoxycarbonyl). Crude (R)-5-Biphenyl-4-ylmethyl-3-methylene-2-oxo-pyrrolidine-1-carboxylic acid tert-butylester (1a, R1=t-butoxycarbonyl) can be purified by column chromatography eluting with 3:1 heptane/ethyl acetate. The ratio of intermediate (3S,5S-4, R1=t-butoxycarbonyl, R4=isopropyl) to (3R,5S-4, R1=t-butoxycarbonyl, R4=isopropyl) is 70:30 as determined by HPLC. Spectroscopic data as Example 28, Method 1.

EXAMPLE 32

R)-5-Biphenyl-4-ylmethyl-3-methylene-pyrrolidin-2-one (1a, R1=H

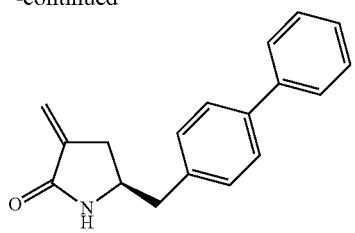

(R)-5-Biphenyl-4-ylmethyl-3-methylene-1-pyrrolidin-1-ylmethyl-pyrrolidin-2-one (1a, R1=pyrrolidinylmethyl) (0.35 g, 1 mmol) is mixed with a mixture of acetic acid and concentrated hydrochloric acid (10 mL ratio 1:1) and stirred under reflux for about 3 hours. The solution was then concentrated under vacuum and the residue is purified by column chromatography eluting with 1:1 heptane/ethyl acetate to give (R)-5-biphenyl-4-ylmethyl-3-methylene-pyrrolidin-2-one (1a, R1=H). ¹HNMR (400 MHz, CDCl₃): 2.58 (m, 1H, 3-CHH), 2.76 (m, 1H, 3CHH), 2.90 (dd, 1H, 5-CHH), 2.99 (dd, 1H, 5-CHH), 3.92 (m, 1H, 4-CH), 5.37 (d, 1H, C=CHH), 6.01 (d, 1H, C=CHH), 7.20~7.60 (9H, m, aromatic).

HPLC Method

Column: Eclipse XDB-C18; 150×4.6 mm; 5 μm. Mobile Phase A (0.1% H₃PO₄) in water; Mobile Phase B (Acetonitrile). Gradient: 0 min (30% B); 8 min (95% B); 15 min (95% B). Flow rate: 1.0 ml min⁻¹. Wavelength: 210 nm. Temperature: 30° C.

Retention time:
6.7 min (1a, R1=H)

EXAMPLE 33

R)-5-Biphenyl-4-ylmethyl-1-((E)-but-1-enyl)-3-methylene-pyrrolidin-2-one (1a, R1=H (R)-5-Biphenyl-4-ylmethyl-1-((E)-but-1-enyl)-3-methylene-pyrrolidin-2-one (1a, R1=1-butenyl) (11.5 g, 35.6 mmol) is dissolved in 100 mL of toluene, add 35 mL of concentrated HCl, refluxed under N₂ for 5 h, cooled to room temperature, separate the aqueous phase, washed with sodium hydrogen carbonate aqueous solution and brine, dry over anhydrous Na$_2$SO$_4$ and concentrate under vacuum, the residue is recrystallized from toluene/tert-butylmethylether=1:3~1:4 to give (R)-5-Biphenyl-4-ylmethyl-1-((E)-but-1-enyl)-3-methylene-pyrrolidin-2-one (1a, R1=H). Spectroscopic data as Example 32.

EXAMPLE 34

R)-5-Biphenyl-4-ylmethyl-3-methylene-pyrrolidin-2-one (1a, R1=H

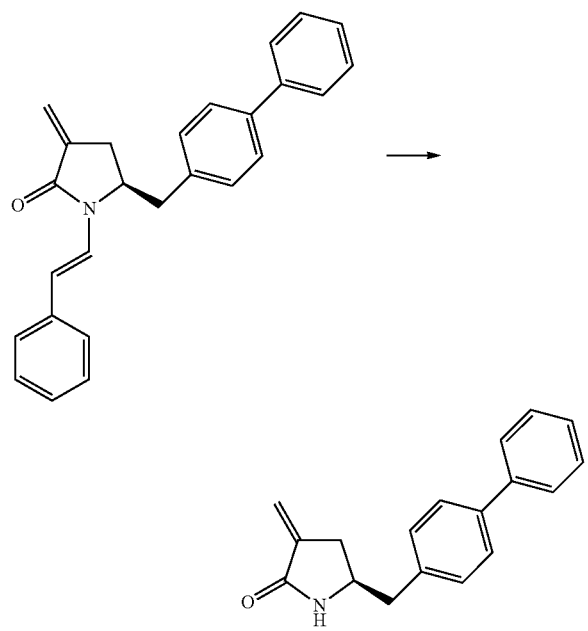

Method 1

(R)-5-Biphenyl-4-ylmethyl-3-methylene-1-((E)-styryl)-pyrrolidin-2-one (1a, R1=styryl) (1.0 g, 2.7 mmol) is dissolved in 10 mL of ethanol, add concentrated HCl (5 mL), reflux under nitrogen atmosphere overnight. The reaction mixture is cooled to room temperature, concentrate under vacuum, the residue is extracted with toluene, the organic phase is washed with saturated Na$_2$SO$_3$ aqueous solution, Na$_2$CO$_3$ aqueous solution and brine, dry over anhydrous Na$_2$SO$_4$ and evaporate the solvent under vacuum to obtain the crude product which recrystallized from Toulene/tert-butylmethylether=1:3~1:4 to give (R)-5-Biphenyl-4-ylmethyl-3-methylene-pyrrolidin-2-one (1a, R1=H). $^1$HNMR (400 MHz, CDCl$_3$): 2.56 (m, 1H, 3-CHH), 2.77 (m, 1H, 5-CHH), 2.89 (m, 1H, 5-CHH), 3.03 (m, 1H, 3-CHH), 3.92 (m, 1H, 4-CH), 5.36 (s, 1H, C=CHH), 6.01 (s, 1H, C=CHH), 6.32 (s, 1H, NHH), 7.24~7.58 (m, 9H, aromatic).

Method 2

(R)-5-Biphenyl-4-ylmethyl-3-methylene-1-((E)-styryl)-pyrrolidin-2-one (1a, R1=styryl) (1.0 g, 2.7 mmol) is dissolved in 10 mL of toluene, add concentrated HCl (5 mL), reflux under nitrogen atmosphere overnight. The reaction mixture is cooled to room temperature, concentrate under vacuum, the residue is extracted with toluene, the organic phase is washed with saturated Na$_2$SO$_3$ aqueous solution, Na$_2$CO$_3$ aqueous solution and brine, dry over anhydrous Na$_2$SO$_4$ and evaporate the solvent under vacuum, the residue is purified by column chromatography to obtain (R)-5-Biphenyl-4-ylmethyl-3-methylene-pyrrolidin-2-one (1a, R1=H). Spectroscopic data as Example 34, Method 1.

Method 3

(R)-5-Biphenyl-4-ylmethyl-3-methylene-1-((E)-styryl)-pyrrolidin-2-one (1a, R1=styryl) (1.0 g, 2.7 mmol) is dissolved in 10 mL of ethanol, add concentrated H$_2$SO$_4$ (1 mL), reflux under nitrogen atmosphere overnight. The reaction mixture is cooled to room temperature, concentrate under vacuum, the residue is dissolved in 20 mL of toluene, the organic phase ish with saturated Na$_2$SO$_3$ aqueous solution, Na$_2$CO$_3$ aqueous solution and brine, dry over anhydrous Na$_2$SO$_4$ and evaporate the solvent under vacuum, the residue is purified by column chromatography to obtain (R)-5-Biphenyl-4-ylmethyl-3-methylene-pyrrolidin-2-one (1a, R1=H). Spectroscopic data as Example 34, Method 1.

Method 4

(R)-5-Biphenyl-4-ylmethyl-3-methylene-1-((E)-styryl)-pyrrolidin-2-one (1a, R1=styryl) (1.0 g, 2.7 mmol) is dissolved in 10 mL of acetic acid, add 1 mL of water, reflux under nitrogen atmosphere overnight. The reaction mixture is cooled to room temperature, concentrate under vacuum, the residue is dissolved in 20 mL of toluene, wash with saturated Na$_2$SO$_3$ aqueous solution, Na$_2$CO$_3$ aqueous solution and brine, dry over anhydrous Na$_2$SO$_4$ and evaporate the solvent under vacuum, the residue is purified by column chromatography to obtain (R)-5-Biphenyl-4-ylmethyl-3-methylene-pyrrolidin-2-one (1a, R1=H). Spectroscopic data as Example 34, Method 1.

Method 5

(R)-5-Biphenyl-4-ylmethyl-3-methylene-1-((E)-styryl)-pyrrolidin-2-one (1a, R1=styryl) (1.0 g, 2.7 mmol) is dissolved in 10 mL of TFA, add 1 mL of water, reflux under nitrogen atmosphere overnight. The reaction mixture is cooled to room temperature, concentrate under vacuum, the residue is dissolved in 20 mL of toluene, wash with saturated Na$_2$SO$_3$ aqueous solution, Na$_2$CO$_3$ aqueous solution and brine, dry over anhydrous Na$_2$SO$_4$ and evaporate the solvent under vacuum, the residue is purified by column chromatography to obtain (R)-5-Biphenyl-4-ylmethyl-3-methylene-pyrrolidin-2-one (1a, R1=H). Spectroscopic data as Example 34, Method 1.

Method 5

(R)-5-Biphenyl-4-ylmethyl-3-methylene-1-((E)-styryl)-pyrrolidin-2-one (1a, R1=styryl) (1.0 g, 2.7 mmol) is dissolved in 10 mL of TFA, add 1 mL of water, reflux under nitrogen atmosphere overnight. The reaction mixture is cooled to room temperature, concentrate under vacuum, the residue is dissolved in 20 mL of toluene, wash with saturated Na$_2$SO$_3$ aqueous solution, Na$_2$CO$_3$ aqueous solution and brine, dry over anhydrous Na$_2$SO$_4$ and evaporate the solvent under vacuum, the residue is purified by column chromatography to obtain (R)-5-Biphenyl-4-ylmethyl-3-methylene-pyrrolidin-2-one (1a, R1=H). Spectroscopic data as Example 34, Method 1.

Method 6

To a solution of (R)-5-Biphenyl-4-ylmethyl-3-methylene-1-((E)-styryl)-pyrrolidin-2-one (1a, R1=styryl) (1.0 g, 2.7 mmol) in 10 mL of tetrahydrofuran is added 1 mL of Methanesulfonic acid and 1 mL of water, reflux under nitrogen atmosphere overnight. The reaction mixture is cooled to room temperature, concentrate under vacuum, the residue is dissolved in 20 mL of toluene, wash with saturated Na$_2$SO$_3$ aqueous solution, Na$_2$CO$_3$ aqueous solution and brine, dry over anhydrous Na$_2$SO$_4$ and evaporate the solvent under vacuum, the residue is purified by column chromatography to obtain (R)-5-Biphenyl-4-ylmethyl-3-methylene-pyrrolidin-2-one (1a, R1=H). Spectroscopic data as Example 34, Method 1.

Method 7

(R)-5-Biphenyl-4-ylmethyl-3-methylene-1-((E)-styryl)-pyrrolidin-2-one (1a, R1=styryl) (10.0 g, 27 mmol) is dissolved in 30 mL of anhydrous toluene, add TsOH*H$_2$O (6.2 g, 32.4 mmol), reflux under nitrogen atmosphere overnight. The reaction mixture is cooled to room temperature, add 100 mL of toluene, the organic phase wash with saturated Na$_2$SO$_3$ aqueous solution, Na$_2$CO$_3$ aqueous solution and brine, dry over anhydrous Na$_2$SO$_4$ and evaporate the solvent under vacuum to obtain the crude product which recrystallize from toluene/tert-butylmethylether=1:3~1:4 to give (R)-5-Biphenyl-4-ylmethyl-3-methylene-pyrrolidin-2-one (1a, R1=H). Spectroscopic data as Example 34, Method 1.

HPLC Method (Methods 1-7)

Column: Eclipse XDB-C18; 150×4.6 mm; 5 μm. Mobile Phase A (0.1% H$_3$PO$_4$) in water; Mobile Phase B (Acetonitrile). Gradient: 0 min (30% B); 8 min (95% B); 15 min (95% B). Flow rate: 1.0 ml min$^{-1}$. Wavelength: 210 nm. Temperature: 30° C.

Retention time:

6.7 min (1a, R1=H).

EXAMPLE 35

(R)-5-Biphenyl-4-yl-4-tert-butoxycarbonylamino-2-methylenepentanoic acid

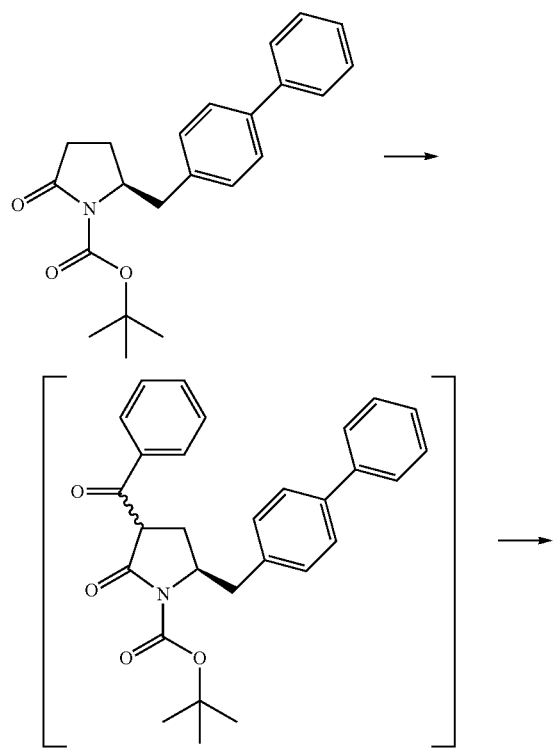

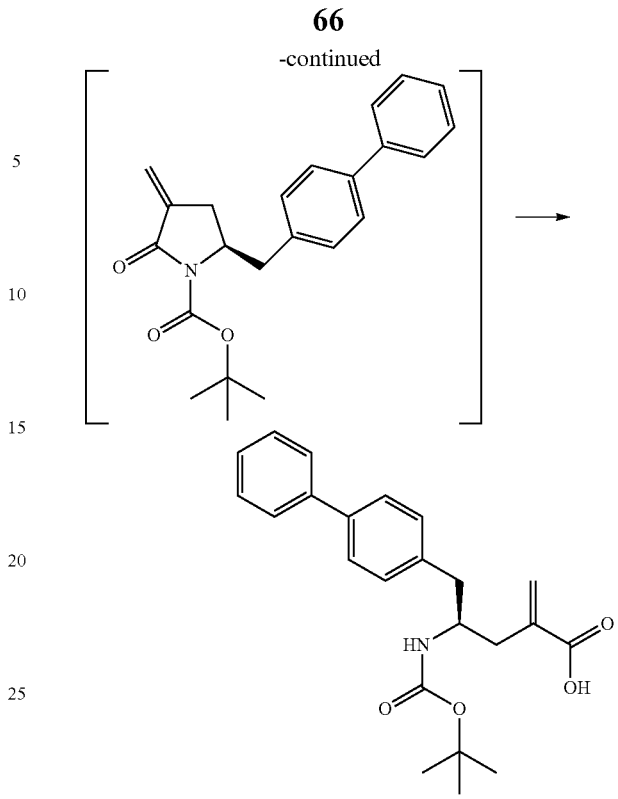

Method 1

Under N$_2$, n-butyllithium (56 mL, 2.5 M in hexane, 0.14 mol) is added to the mixture of HMDS (24.2 g, 0.15 mol) in 300 mL dry tetrahydrofuran at –10° C., the resulting mixture is then stirred for 30 min at –10° C. A mixture of (S)-2-Biphenyl-4-ylmethyl-5-oxo-pyrrolidine-1-carboxylic acid tert-butyl ester (3a, R1=t-butoxycarbonyl) (35.1 g, 0.1 mol) in 50 mL dry tetrahydrofuran is added to the reaction mixture at –10° C., after about 30 min, n-butyllithium (40 mL, 2.5 M in hexane, 0.1 mol) is added to the reaction mixture at –10° C., the resulting mixture is then stirred for 30 min at –10° C. benzoyl chloride (15.5 g, 0.11 mol) is added to the reaction mixture at –10° C., after about 1 hour at –10° C., the reaction mixture is diluted with 100 mL saturated aqueous ammonium chloride solution and stirred for 15 min, stop stirring, and remove the lower aqueous layer. Formaldehyde (37% in water, 24.3 g, 0.3 mol), K$_2$CO$_3$ aqueous solution (27.6 g in 100 mL water, 0.2 mol) and tetrabutyl-ammonium-hydroxide solution (40% in water, 1.3 g, 5 mmol) are added to the remaining organic phase, and heated to 50° C., and stirred for 2 hours. Then the reaction mixture is diluted with 100 mL brine and stirred for 15 min, stop stirring, and remove the lower aqueous layer. Lithium hydroxide monohydrate solution (15 g in 100 mL water, 0.36 mol) and tetrabutylammonium bromide (0.32 g, 1 mmol) are added to the remaining organic phase, stirred at r.t. for 2 hours. Then, about 50 g of phosphoric acid 85% is added in order to set the pH to 3.0-4.0. Then 100 mL toluene and 100 mL brine is added. After phase separation and concentrated under vacuo. The residue is dissolved in 200 mL acetonitrile at 80° C., filtered hot (80° C.) to remove inorganic salt and cooled to 0° C., whereas crystallization occurs and standing for 3 hours, crystals are collected by filtration, washed with 50 mL acetonitrile and died under vacuum at 50° C. to afford (R)-5-Biphenyl-4-yl-4-tert-butoxycarbonylamino-2-methylenepentanoic acid. 1HNMR (400 MHz, DMSO): 1.27 (s, 9H, (CH$_3$)$_3$), 2.26 (m, 1H, 3-CHH), 2.49 (m, 1H, 3CHH), 2.71 (d, 1H, 5-CH$_2$), 3.85 (m, 1H, 4-CH), 5.60 (s, 1H, C═CHH), 6.05 (s, 1H, C═CHH), 6.65 (d, 1H, NH), 7.20~7.70 (9H, m, aromatic), 12.34 (s, 1H, COOH). The ratio of intermediate (3S,5S-4, R1═t-butoxycarbonyl, R4═phenyl) to (3R,5S-4, R1═t-butoxycarbonyl, R4═phenyl) is 70:30 as determined by HPLC. Spectroscopic data as Example 35, Method 1.

Method 2

Under N$_2$, n-butyllithium (56 mL, 2.5 M in hexane, 0.14 mol) is added to the mixture of Diisopropylamine (14.2 g, 0.15 mol) in 300 mL dry tetrahydrofuran at −10° C., the resulting mixture is then stirred for 30 min at −10° C. a mixture of (S)-2-Biphenyl-4-ylmethyl-5-oxo-pyrrolidine-1-carboxylic acid tert-butyl ester (3a, R1═t-butoxycarbonyl) (35.1 g, 0.1 mol) in 50 mL dry tetrahydrofuran is added to the reaction mixture at −10° C., after about 30 min, n-butyllithium (40 mL, 2.5 M in hexane, 0.1 mol) is added to the reaction mixture at −10° C., the resulting mixture is then stirred for 30 min at −10° C. benzoyl chloride (15.5 g, 0.11 mol) is added to the reaction mixture at −10° C., after about 1 hour at −10° C., the reaction mixture is diluted with 100 mL saturated aqueous ammonium chloride solution and stirred for 15 min, stop stirring, and remove the lower aqueous layer. Formaldehyde (37% in water, 24.3 g, 0.3 mol), K$_2$CO$_3$ aqueous solution (27.6 g in 100 mL water, 0.2 mol) and tetrabutyl-ammonium-hydroxide solution (40% in water, 1.3 g, 5 mmol) are added to the remaining organic phase, and heated to 50° C., and stirred for 2 hours. Then the reaction mixture is diluted with 100 mL brine and stirred for 15 min, stop stirring, and remove the lower aqueous layer. Lithium hydroxide monohydrate solution (15 g in 100 mL water, 0.36 mol) and tetrabutylammonium bromide (0.32 g, 1 mmol) are added to the remaining organic phase, stirred at r.t. for 2 hours. Then, about 50 g of phosphoric acid 85% is added in order to set the pH to 3.0-4.0. then 100 mL toluene and 100 mL brine is added. After phase separation and concentrated under vacuo. The residue is dissolved in 200 mL acetonitrile at 80° C., filtered hot (80° C.) to remove inorganic salt and cooled to 0° C., whereas crystallization occurs and standing for 3 hours, crystals are collected by filtration, washed with 50 mL acetonitrile and died under vacuum at 50° C. to afford (R)-5-Biphenyl-4-yl-4-tert-butoxycarbonylamino-2-methylenepentanoic acid. The ratio of intermediate (3S,5S-4, R1═t-butoxycarbonyl, R4═phenyl) to (3R,5S-4, R1═t-butoxycarbonyl, R4═phenyl) is 70:30 as determined by HPLC. Spectroscopic data as Example 35, Method 1.

Method 3

Under N$_2$, LHMDS (25 mL, 1.0 M in tetrahydrofuran, 25 mmol) is added to the mixture of (S)-2-Biphenyl-4-ylmethyl-5-oxo-pyrrolidine-1-carboxylic acid tert-butyl ester (3a, R1═t-butoxycarbonyl) (3.51 g, 10 mmol) in 20 mL dry tetrahydrofuran is added to the reaction mixture at −10° C., the resulting mixture is then stirred for 30 min at −10° C. benzoyl chloride (1.55 g, 11 mmol) is added to the reaction mixture at −10° C., after about 1 hour at −10° C., the reaction mixture is diluted with 15 mL saturated aqueous ammonium chloride solution and stirred for 15 min, stop stirring, and remove the lower aqueous layer. Formaldehyde (37% in water, 2.43 g, 0.03 mol), K$_2$CO$_3$ aqueous solution (2.76 g in 10 mL water, 0.02 mol) and tetrabutyl-ammonium-hydroxide solution (40% in water, 0.13 g, 0.5 mmol) are added to the remaining organic phase, and heated to 50° C., and stirred for 2 hours. Then the reaction mixture is diluted with 15 mL brine and stirred for 15 min, stop stirring, and remove the lower aqueous layer. Lithium hydroxide monohydrate solution (1.5 g in 10 mL water, 0.036 mol) and tetrabutylammonium bromide (32 mg, 0.1 mmol) are added to the remaining organic phase, stirred at r.t. for 2 hours. Then, about 5 g of phosphoric acid 85% is added in order to set the pH to 3.0-4.0. then 15 mL toluene and 15 mL brine is added. After phase separation and concentrated under vacuo. The residue is dissolved in 20 mL acetonitrile at 80° C., filtered hot (80° C.) to remove inorganic salt and cooled to 0° C., whereas crystallization occurs and standing for 3 hours, crystals are collected by filtration, washed with 5 mL acetonitrile and died under vacuum at 50° C. to afford (R)-5-Biphenyl-4-yl-4-tert-butoxycarbonylamino-2-methylenepentanoic acid. The ratio of intermediate (3S,5S-4, R1═t-butoxycarbonyl, R4═phenyl) to (3R,5S-4, R1═t-butoxycarbonyl, R4═phenyl) is 70:30 as determined by HPLC. Spectroscopic data as Example 35, Method 1.

Method 4

Under N$_2$, LDA (25 mL, 1.0 M in tetrahydrofuran, 25 mmol) is added to the mixture of (S)-2-Biphenyl-4-ylmethyl-5-oxo-pyrrolidine-1-carboxylic acid tert-butyl ester (3a, R1═t-butoxycarbonyl) (3.51 g, 10 mmol) in 20 mL dry tetrahydrofuran is added to the reaction mixture at −10° C., the resulting mixture is then stirred for 30 min at −10° C. benzoyl chloride (1.55 g, 11 mmol) is added to the reaction mixture at −10° C., after about 1 hour at −10° C., the reaction mixture is diluted with 15 mL saturated aqueous ammonium chloride solution and stirred for 15 min, stop stirring, and remove the lower aqueous layer. Formaldehyde (37% in water, 2.43 g, 0.03 mol), K$_2$CO$_3$ aqueous solution (2.76 g in 10 mL water, 0.02 mol) and tetrabutyl-ammonium-hydroxide solution (40% in water, 0.13 g, 0.5 mmol) are added to the remaining organic phase, and heated to 50° C., and stirred for 2 hours. Then the reaction mixture is diluted with 15 mL brine and stirred for 15 min, stop stirring, and remove the lower aqueous layer. Lithium hydroxide monohydrate solution (1.5 g in 10 mL water, 0.036 mol) and tetrabutylammonium bromide (32 mg, 0.1 mmol) are added to the remaining organic phase, stirred at r.t. for 2 hours. Then, about 5 g of phosphoric acid 85% is added in order to set the pH to 3.0-4.0. then 15 mL toluene and 15 mL brine is added. After phase separation and concentrated under vacuo. The residue is dissolved in 20 mL acetonitrile at 80° C., filtered hot (80° C.) to remove inorganic salt and cooled to 0° C., whereas crystallization occurs and standing for 3 hours, crystals are collected by filtration, washed with 5 mL acetonitrile and died under vacuum at 50° C. to afford (R)-5-biphenyl-4-yl-4-tert-butoxycarbonylamino-2-methylenepentanoic acid. The ratio of intermediate (3S,5S-4, R1═t-butoxycarbonyl, R4═phenyl) to (3R,5S-4, R1═t-butoxycarbonyl, R4═phenyl) is 70:30 as determined by HPLC. Spectroscopic data as Example 35, Method 1.

Method 5

Under N$_2$, to a 1-L of flask is added (S)-2-Biphenyl-4-ylmethyl-5-oxo-pyrrolidine-1-carboxylic acid tert-butyl ester (3a, R1═t-butoxycarbonyl) (40 g, 159 mmol) and DMAP (2.43 g, 20 mmol), followed by 500 mL of toluene and triethylamine (26.1 g, 258 mmol). The mixture is warmed up to 65° C., di-tert-butyl dicarbonate (48.6 g, 223 mmol) is added over 30 min, then stirred for 2 hours. The reaction mixture is cooled to 25° C., washed with 200 mL of water three times, then concentrated. The residue is dissolved in 400 mL of THF, MgCl$_2$ (18.0 g, 159 mm) and triethylamine (26.1 g, 258 mmol) are added. The reaction mixture is cooled to 5° C., benzoyl chloride (36.4 g, 259 mmol) is added dropwise slowly, after addition, the mixture is stirred at 5° C. for 1 h, then warm to 10° C. and stirred for 15 h. 100 mL of water are added, followed by a solution of H$_3$PO$_4$ (57.4 g, 510 mol) in water (100 mL). After 10 min, the aqueous phase is removed and the organic phase is washed with brine (200 mL) twice. To the organic extracts are added potassium carbonate solution (65.4 g, in 200 mL of water), N-methylimidazole (32.6 g, 398 mmol), tetrabutyl-ammonium-hydroxide solution (3.68 g, 40% w/w, 5.7 mmol) and formaldehyde solution in water (48.4 g, 37% w/w, 613 mmol). This mixture is warmed to 55° C., and stirred for 20 h. After this time, the reaction temperature is cooled to 25° C. and the aqueous phase is removed. The organic phase is washed with saturated sodium chloride (200 mL) twice. Lithium hydroxide monohydrate solution (29.3 g in 200 mL of water, 698 mmol) and tetrabutyl ammonium bromide (0.65 g, 2 mmol) is added. The mixture is stirred at 25° C. for 4 h. Then phosphoric acid (97.6 g, 85% w/w) is added to the reaction mixture, pH is adjusted to 4-5 at 10-20° C. The aqueous phase is removed and a saturated sodium chloride solution in water (200 mL) is added. The organic phase is separated and concentrated. The residue is dissolved in ethyl acetate (500 mL) and then removed under vacuum. Ethyl acetate (1000 mL) and water (400 mL) is added. The organic phase is separated, washed with water (400 mL) three times, and concentrated. To the resulting residue is added toluene (400 mL) and then removed under vacuum. Acetonitrile is added (400 mL). The reaction mixture is refluxed and cooled down in about 2 h to 4° C. The resulting solid is separated by filtration. The filter cake is washed with cold acetonitrile (50 mL), followed by heptane (100 mL) and dried to give (R)-5-biphenyl-4-yl-4-tert-butoxycarbonylamino-2-methylenepentanoic acid as a white solid. The ratio of intermediate (3S,5S-4, R1=t-butoxycarbonyl, R4=phenyl) to (3R, 5S-4, R1=t-butoxycarbonyl, R4=phenyl) is 70:30 as determined by HPLC. Spectroscopic data as Example 35, Method 1.

HPLC Method (Methods 1-5)

Column: Eclipse XDB-C18; 150×4.6 mm; 5 μm. Mobile Phase A (0.1% H3PO4) in water; Mobile Phase B (Acetonitrile). Gradient: 0 min (30% B); 8 min (95% B); 15 min (95% B). Flow rate: 1.0 ml min-1. Wavelength: 210 nm. Temperature: 30° C.

Retention time:
8.0 min (R)-5-biphenyl-4-yl-4-tert-butoxycarbonylamino-2-methylenepentanoic acid

The invention claimed is:

1. A process for preparing a compound of formula (4), or salt thereof,

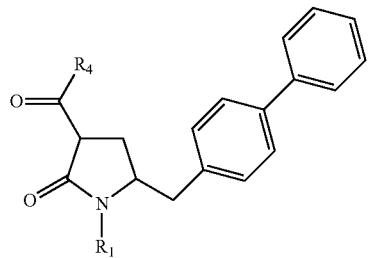

(4)

wherein
R1 is hydrogen or a nitrogen protecting group; and
R4 is selected from hydroxyl, alkyl, aryl and arylalkyl;
said process comprising
reacting a compound of formula (3), or salt thereof,

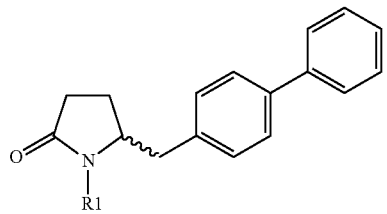

(3)

wherein R1 is hydrogen or a nitrogen protecting group;
first with a base and then with a compound of the formula CO$_2$ or R4COY, wherein Y is halogen or —OR' and wherein R4 and R' are independently selected from alkyl, aryl and arylalkyl, to obtain the compound of formula (4), or salt thereof.

2. The process according to claim 1, wherein R4 is hydroxyl and wherein the compound of formula (3) is reacted first with a base and then with a compound of the formula CO$_2$.

3. The process according to claim 1, wherein R4 is selected from alkyl, aryl and arylalkyl and wherein the compound of formula (3) is reacted first with a base and then with a compound of the formula R4COY, wherein Y is halogen or —OR' and wherein R4 and R' are independently selected from alkyl, aryl and arylalkyl.

4. The process according to claim 1, wherein the base is selected from
a metal hydride;
an alkali metal alkoxide;
an amine, optionally in the presence of an additive selected from an alkaline earth metal halide;
a base of the formula MRa, wherein M is an alkali metal and Ra is alkyl or aryl;
a base of the formula RcRdNM, wherein Rc and Rd are independently selected from alkyl, cycloalkyl, heterocyclyl and silyl and M is an alkali metal; and
mixtures thereof.

5. A process for preparing a compound of formula (1), or salt thereof,

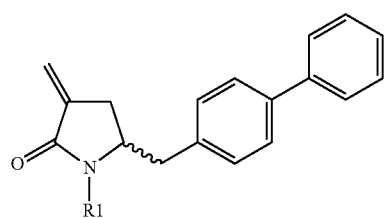

(1)

wherein R1 is hydrogen or a nitrogen protecting group;
said process comprising
reacting a compound of formula (4), or salt thereof,

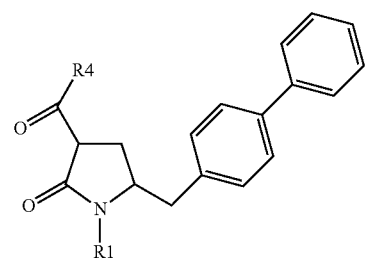

(4)

wherein
R1 is hydrogen or a nitrogen protecting group; and
R4 is selected from hydroxyl, alkyl, aryl and arylalkyl;
with a base and formaldehyde, optionally in the presence of a phase transfer catalyst, to obtain the compound of formula (1), or salt thereof.

6. The process according to claim 5, wherein the base is selected from
a metal hydride;
an amine;
an inorganic base;
a base of the formula MRa, wherein M is an alkali metal and Ra is alkyl or aryl;

a base of the formula RcRdNM, wherein Rc and Rd are independently selected from alkyl, cycloalkyl, heterocyclyl and silyl and M is an alkali metal; and mixtures thereof.

7. The process according to claim 5 wherein the reaction further comprises adding an alkali metal salt and optionally a drying agent.

8. A process for preparing a compound of formula (1), or salt thereof,

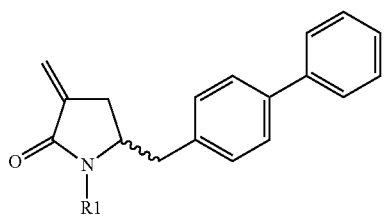
(1)

wherein R1 is hydrogen or a nitrogen protecting group;

said process comprising the steps of (i) preparing a compound of formula (4), or salt thereof,

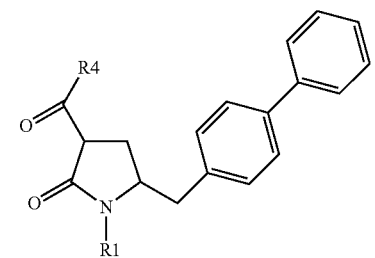
(4)

wherein

R1 is hydrogen or a nitrogen protecting group; and

R4 is selected from hydroxyl, alkyl, aryl and arylalkyl;

by reacting a compound of formula (3), or salt thereof,

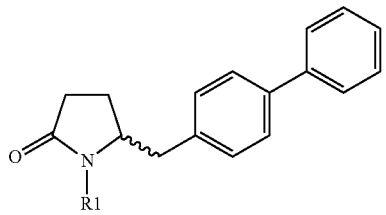
(3)

wherein R1 is hydrogen or a nitrogen protecting group;

(i) first with a base and then with a compound of the formula $CO_2$ or R4COY, wherein Y is halogen or —OR' and wherein R4 and R' are independently selected from alkyl, aryl and arylalkyl, to obtain the compound of formula (4), or salt thereof; and (ii) reacting the compound of formula (4), or salt thereof,

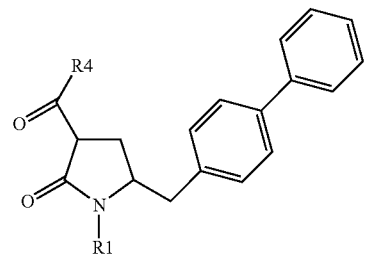
(4)

wherein

R1 is hydrogen or a nitrogen protecting group; and

R4 is selected from hydroxyl, alkyl, aryl and arylalkyl;

with a base and formaldehyde, optionally in the presence of a phase transfer catalyst, to obtain the compound of formula (1), or salt thereof.

9. The process according to claim 8 wherein the base used in step i) is selected from a metal hydride;

an alkali metal alkoxide;

an amine, optionally in the presence of an additive selected from an alkaline earth metal halide;

a base of the formula MRa, wherein M is an alkali metal and Ra is alkyl or aryl;

a base of the formula RcRdNM, wherein Rc and Rd are independently selected from alkyl, cycloalkyl, heterocyclyl and silyl and M is an alkali metal; and mixtures thereof and the base used in step ii) is selected from a metal hydride;

an amine;

an inorganic base;

a base of the formula MRa, wherein M is an alkali metal and Ra is alkyl or aryl;

a base of the formula RcRdNM, wherein Rc and Rd are independently selected from alkyl, cycloalkyl, heterocyclyl and or silyl and M is an alkali metal; and mixtures thereof.

10. The process according to claim 8, wherein steps i) and ii) take place via one-pot.

11. The process according to claim 1 wherein

R1 is selected from t-butoxycarbonyl, benzoyl, styryl, 1-butenyl, benzyl, p-methoxybenzyl and pyrrolidinylmethyl; and R4 is selected from t-butyl, methyl, isopropyl, phenyl and hydroxyl.

12. A compound of formula (4), or salt thereof,

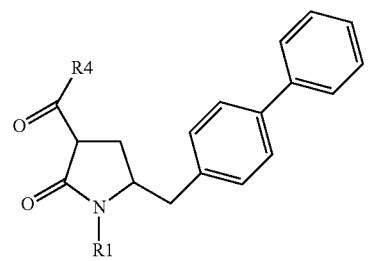
(4)

wherein

R1 is hydrogen or a nitrogen protecting group; and

R4 is selected from hydroxyl, alkyl, aryl and arylalkyl.

13. The compound according to claim 12 wherein
R1 is selected from t-butoxycarbonyl, benzoyl, styryl, 1-butenyl, benzyl, p-methoxybenzyl and pyrrolidinylmethyl; and
R4 is selected from t-butyl, methyl, isopropyl, phenyl and hydroxyl.

14. A process according to claim 1, wherein the compound of formula (4) is of the formula (4a)

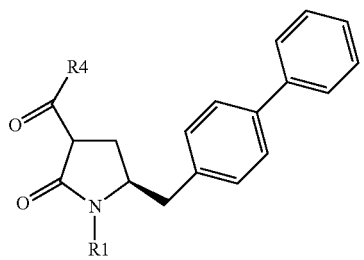

(4a)

wherein R1 and R4 are as defined for the compound of formula (4); and
wherein the compound of formula (3) is of the formula (3a)

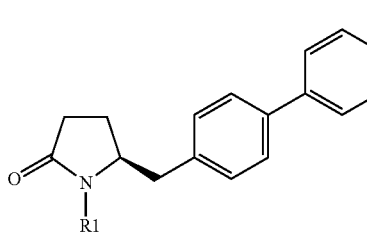

(3a)

wherein R1 is as defined for the compound of formula (3).

15. A process according to claim 5, wherein the compound of formula (1) is of the formula (1a)

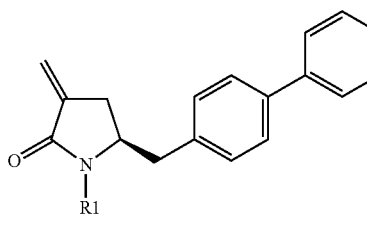

(1a)

wherein R1 is as defined for the compound of formula (1); and
wherein the compound of formula (4) is of the formula (4a)

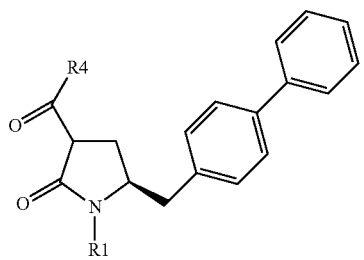

(4a)

wherein R1 and R4 are as defined for the compound of formula (4).

16. A process according to claim 8 wherein the compound of formula (1) is of the formula (1a)

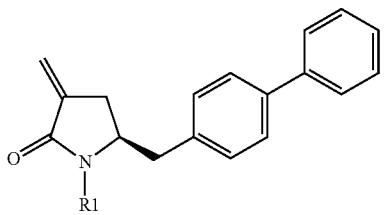

(1a)

wherein R1 is as defined for the compound of formula (1); and
wherein the compound of formula (4) is of the formula (4a)

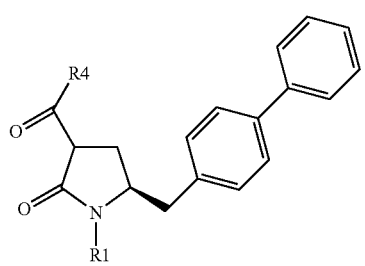

(4a)

wherein R1 and R4 are as defined for the compound of formula (4); and
wherein the compound of formula (3) is of the formula (3a)

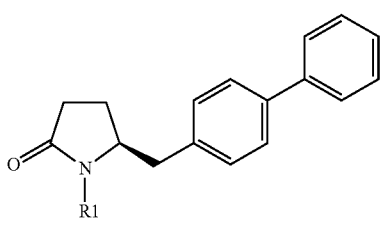

(3a)

wherein R1 is as defined for the compound of formula (3).

17. A process according to claim 12 wherein the compound of formula (4) is of the formula (4a)

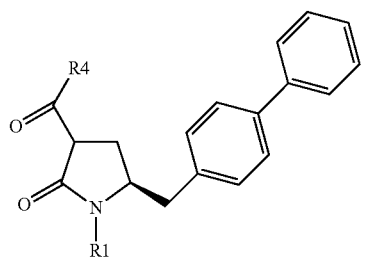

(4a)

wherein R1 and R4 are as defined for the compound of formula (4).

* * * * *